US006444870B1

(12) United States Patent
Zhang et al.

(10) Patent No.: US 6,444,870 B1
(45) Date of Patent: Sep. 3, 2002

(54) METHODS FOR ASSESSING THE ROLE OF CALCINEURIN IMMUNOSUPPRESSION AND NEUROTOXICITY

(75) Inventors: Wei Zhang, Stanford, CA (US); Jonathan G. Seidman, Milton, MA (US); Usamah S. Kagyali, Somerville, MA (US); Huntington Potter, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/212,868

(22) Filed: Dec. 16, 1998

Related U.S. Application Data

(63) Continuation of application No. 08/433,162, filed on May 3, 1995, now abandoned.

(51) Int. Cl.[7] .................... A01K 67/027; G01N 33/00; C12N 15/00; C12N 15/63; C12N 15/85

(52) U.S. Cl. ............................... 800/3; 800/18; 800/25; 435/455; 435/463; 435/320.1; 435/325

(58) Field of Search ................................ 800/3, 14, 18, 800/21, 22, 25, 12; 435/455, 463, 320.1, 325, 69.1

(56) References Cited

U.S. PATENT DOCUMENTS 5,387,742 A    2/1995    Cordell .......................... 800/2

FOREIGN PATENT DOCUMENTS

| EP | 0 544 942 A1 | 6/1993 | ........... C12N/15/12 |
| WO | WO 93/03177 | 2/1993 | ............. C12Q/1/02 |
| WO | WO 95/05466 | 2/1995 | ........... C12N/15/54 |
| WO | WO 95/19178 | 7/1995 | ........... A61K/33/32 |

OTHER PUBLICATIONS

Moreadith et al., Journal of Molecular Medicine, vol. 75 pp. 208–216, 1997.*
Moens et al., Development, vol. 119, pp. 485–499, 1993.*
Seamark, Reproduction, Fertility and Development, vol. 6, No. 5, pp. 653–657, 1994.*
Mullins et al., Journal of Clinical Investigations, vol. 998, No. 11, pp. S37–S40, 1996.*
Hammer et al., Journal of Animal Science, vol. 63 pp. 269–278, 1986.*
Ebert et al., Molecular Endocrinology, vol. 2, pp. 277–283, 1988.*
Wall, Theriogenology, vol. 45, pp. 57–68, 1996.*
Kappel et al., Current Opinion in Biotechnology, vol. 3, pp. 548–553, 1992.*
Strojek & Wagner, Genetic Engineering: Principles and Methods, vol. 10, pp. 211–246, 1988.*

Pearson, B.E. and Choi, T.K., "Expression of the human β–amyloid precursor protein gene from a yeast artificial chromosome in transgenic mice," *Proc. Natl. Acad. Sci., USA,* 90:10578–10582 (1993).
Yamaguchi, F., et al., "Transgenic mice for the amyloid precursor protein 695 isoform have impaired spatial memory", *NeuroReport,* 2:781–784 (1991).
Kammesheidt, A., et al., "Deposition of β/A4 immunoreactivity and neuronal pathology in transgenic mice expressing the carboxyl–terminal fragment of the Alzheimer amyloid precursor in the brain", *Proc. Natl. Acad. Sci., USA,* 89:10857–10861 (1992).
Aguzzi, A., et al., "Transgenic and Knock–Out Mice: Models of Neurological Disease", *Brain Pathology,* 4:3–20 (1994).
Kawabata, S., et al., "Amyloid plaques, neurofibrillary tangles and neuronal loss in brains of transgenic mice overexpressing a C–terminal fragment of human amyloid precursor protein", *Nature,* 354:476–478 (1991).
Delacourte, A., et al., "Towards the development of an in vitro study model of Alzheimer–type neurofibrillary degeneration", *Press Méd.,* 19:170–173 (1990).
Kawabata, S., et al., "Alzheimer's retraction", *Nature,* 356:23 (1992).
Quon, D., et al., "Formation of β–amyloid protein deposits in brains of transgenic mice", *Nature,* 352:239–241 (1991).
Lamb, B.T., et al., "Introduction and expression of the 400 kilobase precursor amyloid protein gene in transgenic mice", *Nature Genetics,* 5:22–30 (1993).
Billingsley, M.L., et al., "Calcineurin Immunoreactivity in Alzheimer's Disease", *Exper. Neur.* 126:178–184 (1994).
Hashimoto, Y. and Soderling, T.R., "Regulation of Calcineurin by Phosphorylation". *J. of Biol. Chem.,* 264(28):16524–16529 (1998).

(List continued on next page.)

Primary Examiner—Scott D. Priebe
Assistant Examiner—Peter Paras, JR.
(74) Attorney, Agent, or Firm—Hamilton, Brook, Smith & Reynolds, P.C.

(57) ABSTRACT

The present invention relates to a method of identifying drugs or agents which have immuno-suppressive effects through or as a result of their effect on calcineurin, including drugs which affect the calcineurin Aα (CNAα) subunit or the calcineurin Aβ (CNAβ) subunit. In addition, the present invention relates to a method of identifying drugs which reduce (partially or totally) phosphorylation of the microtubule-associated protein tau, in the nervous system of a mammal; a method of identifying drugs which reduce (partially or totally) paired helical filament formation in the nervous system of a mammal; and a method of identifying drugs which reduce (partially or totally) formation of paired helical filaments, amyloid deposits or both. The present invention also relates to transgenic non-human mammals, such as rodents and particularly mice, which lack a functional calcineurin gene and, thus, have disrupted calcineurin expression.

5 Claims, No Drawings

OTHER PUBLICATIONS

Ferreira, A., et al., "Calcineurin Is Associated with the Cytoaskeleton of Cultured Neurons and Has a role in the Acquisition of Polarity", *Mol. Biol. Cell,* 4:1225–1238 (1993).

Schorderet, M., "Alzheimer's disease: fundamental and therapeutic aspects", *Experientia,* 51:99–105 Birkhäuser Verlag, CH–4010 Base/Switzerland (1995).

Drewes, G., et al., "Dephosphorylation of tau protein and Alzheimer paired helical filaments by calcineurin and phosphatase–2A", *FEBS Letters,* 336(3):425–432 (1993).

Goto, S., et al., "Dephosphorylation of Microtubule–Associated Protein 2, τ Factor, and Tubulin by Calcineurin," *J. Neurochem.,* 45(1):276–283 (1985).

Gong, C.–X., et al., "Alzheimer's Disease Abnormally Phosphorylated τ Is Deophosphorylated by Protein Phosphatase–2B (Calcineurin)", *J. Neurochem.,* 62(2):803–806 (1994).

Martensen, T.M., et al., "Identification of the Site on Calcineurin Phosphorylated by $Ca^{2+}$/CaM–Dependent Kinase II: Modification of the CaM–Binding Domain", *Biochemistry,* 28(24):9243–9247 (1989).

Kuno, T., et al., "Distinct Cellular Expression of Calcineurin Aα and Aβ in Rat Brain", *J. Neurochem.,* 58(5):1643–1651 (1992).

Sandhu, F.A. et al., "Expression of the human B–amyloid protein of Alzheimer's disease specifically in the brains of transgenic mice", *J. Biol. Chem.,* 266(32):21331–21334 (1991).

Gong, C.–X. et al., "Dephosphorylation of Alzheimer's disease abnormally phosphorylated tau by protein phosphatase–2A", *Neurosci.* (Oxford), 61(4):765–72 (1994).

Kincaid, R.L., et al., "Cloning and Characterization of Molecular Isoforms of the Catalytic Subunit of Calcineurin Using Nonisotopic Methods", *J. Biol. Chem,,* 265(19):11312–11319 (1990).

Games, D., et al., "Alzheimer–type neuropathology in transgenic mice overexpressing V717F β–amyloid precursor protein", *Nature,* 373:523.

Bradley, A., et al., "Modifying the Mouse: Design and Desire", *Biotech.,* 10:534–539 (1992).

Capecchi, M.R., "Targeted Gene Replacement", *Scientific Amer.* 270(3):34–41 (1994).

Götz, J., et al., "Somatodendritic localization and hyperphosphorylation of tau protein in transgenic mice expressing the longest human brain tau isoform", *EMBO J.,* 14(7):1304–1313 (1995).

Kincaid, R.L., "Calcineurin as a pivotal Ca2+–sensitive switching element in biological responses: Implications for the regulation of tau phosphorylation in Alzheimer's disease." in *Alzheimer's Disease: Lessons from Cell Biology,* Kosik et al., eds. (Berlin: Springer–Verlag), pp. 88–102 (1995).

* cited by examiner

METHODS FOR ASSESSING THE ROLE OF CALCINEURIN IMMUNOSUPPRESSION AND NEUROTOXICITY

RELATED APPLICATION(S)

This application is a Continuation of U.S. application No. 08/433,162, entitled "Methods of Assessing the Role of Calcineurin in Immunosuppression and Neurotoxicity", by Wei Zhang et al., filed on May 3, 1995, now abandon, the entire teachings of which are incorporated herein by reference.

BACKGROUND

Calcineurin, also known as protein phosphatase 2B, was first identified in the bovine brain. It represents a small family of calcium and calmodulin dependent serine/threonine protein phosphatases. It is expressed in all mammalian tissues examined, and is most abundant in the brain. In lymphocytes, calcineurin is the major soluble calmodulin-binding protein. Calcineurin is a heterodimer consisting of a catalytic subunit (A; 61 kD) and a regulatory subunit (B; 19 kD). The A subunit contains a catalytic domain, a carboxyl-terminal inhibitory domain, a B subunit binding site, and a camodulin binding site. The phosphatase activity of the A subunit is regulated by $CA^{2+}$ through both calmodulin and the B subunit. The B subunit has only a $Ca^{2+}$ dependent regulatory activity and does not have any phosphatase activity. There are two genes encoding closely related (about 80% identical) A subunit isoforms, A$\alpha$ and A$\beta$, in the mouse, human, and rat genomes. The $\alpha$ isoform is the predominant isoform found in brain, thymus, and T cells. The A$\alpha$ and A$\beta$ isoforms have distinct cellular distribution in the brain, with A$\alpha$ most abundant in the hippocampus, cerebral cortex, cerebellum, and striatum. The differential distributions of the two isozymes suggest they may each have specific functions in modulating neuronal activities. The physiologic functions of the different calcineurin A isoforms are not yet defined.

SUMMARY OF THE INVENTION

The present invention relates to a method of identifying drugs or agents which have immuno-suppressive effects through or as a result of their effect on calcineurin, including drugs which affect the calcineurin A$\alpha$ (CNA$\alpha$) subunit or the calcineurin A$\beta$ (CNA$\beta$) subunit. It particularly relates to methods of identifying drugs which inhibit the phosphatase activity of calcineurin. The present invention further relates to a method of identifying drugs which overcome, prevent or reduce (partially or totally) the neurotoxic or other adverse effects of immuno-suppressant drugs, such as cyclosporin A (CsA) and FK506, which exert their effects by inhibiting calcineurin phosphatase activity.

In addition, the present invention relates to a method of identifying drugs which reduce (partially or totally) phosphorylation of the microtubule-associated protein tau, in the nervous system of a mammal; a method of identifying drugs which reduce (partially or totally) paired helical filament formation in the nervous system of a mammal; and a method of identifying drugs which reduce (partially or totally) formation of paired helical filaments, amyloid deposits or both. Such drugs are useful in reducing the extent to which Alzheimer's disease occurs, reducing the rate at which Alzheimer's disease progresses or preventing its occurrence.

The present invention also relates to transgenic non-human mammals, such as rodents and particularly mice, which lack a functional calcineurin gene and, thus, have disrupted calcineurin expression. In one embodiment, transgenic non-human mammals of the present invention lack a functional calcineurin A$\alpha$ (CNA$\alpha$) subunit gene, a functional calcineurin A$\beta$ (CNA$\beta$) subunit gene or both CNA$\alpha$ and CNA$\beta$ subunit genes. In a further embodiment, transgenic non-human mammals (e.g., rodents such as mice and rats) lack a functional calcineurin gene (e.g., calcineurin subunit A$\alpha$ gene, calcineurin subunit A$\beta$ gene) and express human tau protein. In such transgenic mammals, hyperphosphorylation of human tau protein is expressed and polymerizes, resulting in formation of paired helical filaments that make up neurofibrillary tangles in the brain. A third type of transgenic non-human mammal (e.g., rodents, such as mice and rats) lacks a functional calcineurin gene, expresses human tau protein and overexpresses human amyloid precursor protein and human Alzheimer A$\beta$ protein. Such transgenic mammals exhibit both of the pathological lesions of Alzheimer's disease—amyloid deposits and paired helical filaments (which make up the neurofibrillary tangles that accumulate in brain neurons in Alzheimer's disease)—and serve as an improved model for Alzheimer's disease in which to identify drugs or agents which will reduce (partially or totally) the pathological lesions.

DETAILED DESCRIPTION OF THE INVENTION

As described herein, a transgenic non-human mammal which lacks a functional calcineurin (CN) gene produces greatly increased amounts of hyperphosphorylated tau protein. The transgenic non-human mammal of the present invention can be used to identify drugs or agents which have immuno-suppressive effects through or as a result of their effect on CN, including drugs or agents which affect the calcineurin A$\alpha$ (CNA$\alpha$) subunit or the calcineurin A$\beta$ (CNA$\beta$) subunit. In addition, further transgenic mammals of the present invention, described herein, can be used to identify agents which are useful in reducing phosphorylation of tau protein and production of pathological lesions characteristic of Alzheimer's Disease.

In one embodiment, the present invention relates to a method of identifying an agent that reduces the phosphorylation of tau protein in the nervous system of a mammal, comprising the steps of a) administering to a transgenic non-human mammal which lacks a functional CN gene, an agent to be assessed for its ability to reduce phosphorylation of tau protein; b) determining the extent to which phosphorylation of tau protein occurs in the nervous system of the transgenic non-human mammal to which the agent is administered; and c) comparing the extent determined in b) to the extent to which phosphorylation occurs in the nervous system of an appropriate control. If phosphorylation occurs to a lesser extent in the nervous system of the transgenic non-human mammal to which the agent is administered than in the nervous system of the control, the agent reduces phosphorylation of tau protein.

In another embodiment, the present invention relates to a method of identifying an agent which reduces paired helical filament (PHF) formation in the nervous system of a mammal, comprising the steps of: a) administering to a transgenic non-human mammal which lacks a functional CN gene and expresses human tau protein, an agent to be assessed for its ability to reduce PHF formation; b) determining the extent to which PHF formation occurs in the nervous system of the transgenic non-human mammal to which the agent is administered; and c) comparing the extent determined in b) to the extent to which PHF formation occurs in the nervous system of an appropriate control, wherein if PHF formation occurs to a lesser extent in the nervous system of the transgenic non-human mammal to which the agent is administered than in the nervous system of the control, the agent reduces PHF formation. In another embodiment, the present invention relates to a method of identifying an agent which reduces a lesion characteristic of Alzheimer's disease in the nervous system of a mammal comprising the steps of: a) administering to a transgenic non-human mammal which lacks a functional CN gene, expresses a human tau protein, and overexpresses the human amyloid precursor protein and the human Alzheimer Aβ protein, an agent to be assessed for its ability to reduce a lesion characteristic of Alzheimer's disease; b) determining the extent to which the lesion occurs in the nervous system of the transgenic non-human mammal to which the agent is administered; and c) comparing the extent determined in b) to the extent to which the lesion occurs in the nervous system of an appropriate control; wherein if the lesion occurs to a lesser extent in the nervous system of the transgenic non-human mammal to which the agent is administered than in the nervous system of the control, the agent reduces a lesion characteristic of Alzheimer's disease.

The pathological lesions characteristic of Alzheimer's Disease which can be reduced in a mammal using agents identified by the method of the present invention include paired helical filament (PHF) formation and amyloid deposits. In addition, the phosphorylation of tau protein associated with Alzheimer's disease can be reduced using agents identified by the methods of the present invention.

The present invention further relates to a method of identifying an agent that reduces the phosphatase activity of calcineurin AP subunit gene in the nervous system of a mammal, comprising the steps of: a) administering to a transgenic non-human mammal which lacks a functional calcineurin Aβ subunit gene, an agent to be assessed for its ability to reduce the phosphatase activity of calcineurin Aβ subunit; b) determining the calcineurin Aβ subunit phosphatase activity present in cells in the nervous system of the transgenic non-human mammal to which the agent is administered; and c) comparing the calcineurin Aβ phosphatase activity determined in b) to the calcineurin Aβ phosphatase activity in cells in the nervous system of an appropriate control, wherein if calcineurin Aβ phosphatase activity is present to a lesser extent in the nervous system of the transgenic non-human mammal to which the agent is administered than in the nervous system of the control, the agent reduces phosphatase activity of calcineurin Aβ subunit.

The transgenic non-human mammal which lacks a functional CN gene includes mammals in which the CN gene is not present in the genome and mammals in which the structural or functional activity of the CN gene present in the genome of the mammal has been disrupted (both types are referred to as calcineurin knockout mammals). The CNAα subunit gene and/or the CNAβ subunit gene can be removed or functionally disrupted for use in the present invention. For example, as described in Example 1, the genome of a non-human mammal can be recombined with a sequence which becomes inserted into the exon encoding the CNAα gene of the animal, resulting in disruption of CNAα expression. Other methods of producing a CN knockout mammal for use in the present invention can be determined by one of skill in the art using routine experimentation.

A suitable mammal for use in the present invention is a mammal, which upon removal of the CN gene or disruption of the function of the CN gene, produces increased amounts of hyperphosphorylated tau protein. Transgenic non-human mammals of the present invention include rodents, (e.g., rats, mice) and primates.

In the method of the present invention, determination of the ability of an agent to reduce the lesions associated with Alzheimer's Disease is detected in the nervous system of the transgenic mammal. In particular, the effect of the agent to be assessed can be determined in the central nervous system of the transgenic mammal. For example, the effect of the agent to be assessed can be determined in the brain of the transgenic mammal.

The methods used to determine the ability of an agent or drug to reduce a lesion characteristic of Alzheimer's disease, which includes phosphorylation of tau protein, are routine methods known to those of skill in the art. For example, as described in Example 1, determination of the extent to which phosphorylation of the tau protein occurs in the transgenic non-human mammal of the present invention can be determined using anti-PHF antibodies. Anti-PHF antibodies can also be used to determine the extent to which PHF formation occurs. Assessing reduction of amyloid deposits can be determined using anti-β protein, thioflavin S or Congo Red. In addition, behavioral observations of the transgenic mammal to which an agent has been administered can be used to determine the ability of the agent to reduce lesions characteristic of Alzheimer's disease, including phosphorylation of tau protein.

A suitable control is a transgenic non-human mammal which has the same characteristics as the transgenic animal to which an agent being assessed is administered (i.e., the test transgenic non-human mammal). The test and control non-human mammals are maintained under the same conditions; they differ only in the presence (test animal) or absence (control animal) of the agent being assessed. For example, a suitable control used to compare the results achieved with the agent or drug to be assessed, is a transgenic non-human mammal which lacks a functional CN gene, a transgenic non-human mammal which lacks a functional CN gene and expresses a human tau protein or a transgenic non-human mammal which lacks a functional CN gene, expresses a human tau protein and overexpresses the human APP and the human Alzheimer Aβ proteins in the absence of the agent being assessed. For example, in the embodiment for identifying an agent that reduces the phosphorylation of tau protein in the nervous system of a mammal, a suitable control is a transgenic non-human mammal which lacks a functional CN gene. The amount of phosphorylation of tau protein in the control transgenic non-human mammal is determined in the absence of the agent being assessed. Other appropriate controls can be a corresponding wildtype mammal or other control determined by those of skill in the art using no more than routine experimentation.

The present invention further relates to a transgenic non-human mammal which lacks a functional calcineurin gene. In addition, the present invention relates to a transgenic non-human mammal which lacks a functional calcineurin gene and expresses the human tau protein. Further, the present invention relates to a transgenic non-human mammal which lacks a functional calcineurin gene, expresses the human tau protein and overexpresses the human amyloid precursor protein (APP) and the human Alzheimer Aβ protein.

Pathological lesions that characterize the Alzheimer's disease brain and cause the neurodegeneration that leads to dementia include the extracellular amyloid deposits and the intracellular neurofibrillary tangles which are composed of bundles of paired helical filaments as seen in the electron microscope. The amyloid deposits are composed primarily of an approximately 42 amino acid peptide termed Aβ that is derived from the larger precursor protein termed amyloid precursor protein, or APP. The paired helical filaments are composed primarily of the microtubule-associated protein tau that has become abnormally modified with extra phosphate groups (hyperphosphorylated). The relative contribution of these two lesions to the neuronal cell death is not yet known, but both are believed to be important. The correlation with neuronal cell death and dementia is highest with the appearance of the neurofibrillary tangles containing paired helical filaments in neurons. It is, therefore, accepted as axiomatic in the field that a successful treatment for Alzheimer's disease will need to prevent or reduce the formation of paired helical filaments or remove filaments already formed.

At the present time, no rodent model exists that generates paired helical filaments or accumulates hyperphosphorylated tau protein. The Exemplar/Athena transgenic mouse model for Alzheimer's disease overexpresses a mutant form of the APP gene (associated with familial Alzheimer's disease) and shows some synaptic loss and the accumulation of amyloid, but it does not produce paired helical filaments and does not show clear learning disorders (Games, D., et al., Nature, 373:523–527 (1995). It is therefore of importance to develop a mouse model in which paired helical filaments can form. Such a model would serve as a target for testing potential Alzheimer's therapeutic agents designed to reduce or prevent the formation of paired helical filaments. In addition, an animal model, preferably rodent, that shows both amyloid deposits and paired helical filaments would most closely resemble human Alzheimer's disease and would allow the testing of therapeutic agents directed at reducing both of the pathological legions of Alzheimer's disease.

On the basis of the discovery that the calcineurin knockout mouse produces greatly increased amounts of hyperphosphorylated tau protein, the mouse model for Alzheimer's disease in which a hyperphosphorylated form of the human tau protein is expressed, hyperphosphorylated human tau protein and the accumulation of paired helical filaments is exhibited and the Alzheimer amyloid deposits of β protein and the paired helical filaments of hyperphosphorylated tau protein is expressed is generated as described below.

The calcineurin knockout mice is mated to a mouse line homozygous for the expression of a human tau protein. These latter mice have been generated by standard transgenic technology in which the human tau protein is injected into fertilized mouse oocytes in a construct that allows its expression under the control of the human thy 1 promoter. In these animals, the transgenic human tau protein is present in nerve cell bodies, axons, and dendrites and is partially hyperphosphorylated at the appropriate sites for producing paired helical filaments, but not to the degree in the mouse tau protein in the calcineurin knockout mouse line. Mating of these two animals will generate progeny, all of whom will carry a knocked out calcineurin gene on one chromosome, a normal calcineurin gene on the homologous chromosome, and half of whom will carry the human tau transgene.

The genotype of the progeny is determined by removing a small section of the tail, preparing DNA, and carrying out either a Southern Blot or PCR analysis to determine that they all carry one knocked out calcineurin gene and that 50% carry the human tau transgene. The progeny carrying the human tau sequence are grown to adulthood and inter-mated to generate a new set of progeny, 25% of whom are, by Mendelian laws, homozygous for the knocked out calcineurin gene and either homozygous or heterozygous for the human tau transgene. The genotypes of these animals is determined as before by analysis of tail DNA. Animals carrying the knocked out calcineurin gene in homozygous state plus the human tau transgene in either the heterozygous or homozygous state are further analyzed. Animals whose genotypes have been confirmed by the analysis of tail DNA are allowed to reach maturity and inter-mated to generate a line of animals that continues to have the correct genotypes. Mice at different ages are perfused with fixative and subjected to immunocytochemistry and electron microscopy to confirm that they express human tau protein and do not express the calcineurin protein.

Phosphorylation-sensitive antibodies are used as described for the calcineurin knockout mouse to confirm that the human tau protein is hyperphosphorylated due to the lack of calcineurin in its environment. Particular focus is placed on the hippocampus which has previously been shown to be an area of high calcineurin expression and the largest increase in hyperphosphorylation of tau due to the calcineurin knockout mutation. Neurofibrillary tangles are identified by modified Bielchowsky silver stain and by anti-PHF antibodies and are confirmed by electron microscopic identification. The protein expression studies are complemented by northern blot analysis to confirm that the calcineurin gene in these animals is not expressed.

Once a mouse line has been generated, it expresses hyperphosphorylated human tau protein and preferably paired helical filaments in the neurons of the hippocampus. The mice can be used in several ways. First, they can be used directly to screen for therapeutic agents that reduce the hyperphosphorylation of tau and the production of paired helical filaments. They can also be used to test putative therapeutic agents for their efficacy in preventing the hyperphosphorylation of tau and the formation of paired helical filaments. these mice can also be used to determine the ideal dose of a putative therapeutic agent for Alzheimer's disease.

The mice can also be used to generate a further improved animal model for Alzheimer's disease. For this use, homozygous mice which lack a functional calcineurin gene (mice homozygous for the knocked out calcineurin gene) and which express the human tau gene so that hyperphosphorylated human tau protein, and preferably PHF, is produced in the brain are mated to the Exemplar/Athena APP transgenic mouse that overexpresses the APP protein and the Alzheimer Aβ protein and, as a consequence, produces amyloid deposits. The purpose of this cross is to generate progeny that have all of the characteristics of Alzheimer's disease, namely hyperphosphorylated tau, paired helical filaments, and amyloid deposits. The progeny of this cross are analyzed as before using tail DNA to confirm their genotype. For example, two heterozygous animals are crossed, one expressing the human tau transgene and one expressing a human APP transgene. Tail DNA analysis is carried out to determine which of the progeny carry both transgenes. If, on the other hand, the mating is between a homozygous version of the APP transgenic mouse and a homozygous version of the human tau transgenic mouse (of course already combined with the homozygous calcineurin knocked mutation), then technically the tail DNA analysis should not be necessary but is carried out nonetheless in case the germ line of any of the mice has lot any of the transgenes. The progeny of this cross thus carry two human transgenes, one for APP and one for tau under different promoters but both expressed in the nervous system, plus a homozygous knockout mutation in the calcineurin gene.

These mice will produce amyloid deposits and hyperphosphorylated tau/paired helical filaments, thus satisfying the two major criteria for an Alzhemer's animal model. The mice can be used to screen for the test putative therapeutic agents for Alzheimer's disease. They can also, as will the mice mentioned above, be used to test putative diagnostic tests for Alzheimer's disease including, but not limited to, analysis of the tropicamide hypersensitivity of the pupil, the presence of key protein such as antichymotrypsin, APP, A$\beta$, and hyperphosphorylated tau in the serum and/or cerebrospinal fluid.

The invention is illustrated in the following examples which are not intended to be limiting.

EXEMPLIFICATION

Methods and Materials

The following methods and materials were used in the examples described herein. References cited in Examples 1–3 are those included in the subject application which immediately follow Example 3.

Construction of Targeting Vectors

The targeting construct used to disrupt the CNA$\alpha$ gene was designed for implementing the double-selection technique previously described (Mansour, 1988; Mortensen, 1992). Murine CNA$\alpha$ cDNA was cloned by PCR amplification from mouse brain total mRNA using primers corresponding to CNA$\alpha$ cDNA sequence (Kincaid, 1990; accession number J05479) using standard procedures (Ausubel, 1994). A bacteriophage clone encoding part of the calcineurin Ac$\alpha$ catalytic domain (Kincaid, 1990), designated MCAL-1, was obtained by screening a 129/Svj liver genomic library (Strategene) with murine CNA$\alpha$ cDNA. A 13 kb EcoRI fragment from clone MCAL-1 was subcloned into Bluescript-tk using standard procedures (Ausubel, 1994). The intron-exon boundaries of the murine calcineurin A$\alpha$ gene were defined by restriction enzyme site mapping and nucleotide sequence analysis (Ausubel, 1994). The neo gene was inserted into an MluI site in the middle of the exon encoding nucleotides 572–717 of the mouse CNA$\alpha$ mRNA sequence (accession number J05479; Kincaid, 1990). Both neo and tk were driven by the phosphoglycerate kinase promoter.

Transfection and Selection of Mutant ES Cells

J1 ES cells were grown on feeder layers of 7-irradiated embryonic fibroblast (EP) cells as described (Li, 1992). 1.5–2×10$^7$ J1 cells at passage 9–10 were trypsinized and resuspended in 1 ml of electroporation buffer (Thomas and Capecchi, 1987), except that the NaCl concentration was 137 mM. 50 $\mu$g of construct DNA introduced into J1 ES cells by electroporation and grown in G418 and FIAU as described previously (Li, 1992). Surviving clones were picked 8–10 days after selection and DNA was extracted for Southern blot analysis.

Generation of Germline Chimeras

Heterozygous ES cells were injected into C57Bl/6J blastocysts and reimplanted into the uteri of Black Swiss pseudopregnant female mice as described (Bradley, 1987). Agouti male offspring (derived from the 129 ES cells) were mated to Black Swiss or C57Bl/6J females. Tail DNA from the agouti F1 offspring was analyzed by Southern blot analysis for germline transmission of the mutated allele of the CNA$\alpha$ gene. Homozygous mutant mice were obtained by mating the heterozygous mutant mice. The mice used in the experiments presented here were 8–10 weeks old, of either Black Swiss/129 background or of B6/129 background, as noted.

Generation of Double-knockout ES Cells and RAG-2 Chimeras

Homozygous mutant ES cells were generated from heterozygous CNA$\alpha^{+/-}$ES cells as described (Mortensen, 1992) with the following modification. 1–2×10$^6$ heterozygous knockout ES cells from a single clone were plated onto each 10 cm plate on G418-resistant EF cells in LIF- supplemented (1000 U/ml) media. After 12 hours 1.5 mg dry powder G418 was added per ml of culture. After 4–6 days of G418 selection, surviving colonies were picked and the structure of the calcineurin Ac$\alpha$ gene was assessed by Southern blot analysis.

Double knockout ES cells were injected into RAG-2$^{-/-}$ blastocysts (Shinkai , 1992) of either B6/129 or FvB background to generate somatic chimeras (Chen , 1993). The ES cell contribution to the chimera was assessed by coat color (for FvB background only) and by measuring the number of CD4$^+$ and CD8$^+$ lymphocytes in the peripheral blood. The chimeras used in the experiments presented here were 10 weeks old.

Cytofluorometric Analyses

Thymus, lymph nodes, and spleen were isolated from B6/129 wild type and mutant mice and dispersed into single cell suspension. The red blood cells were removed by lysis with Tris/NH$_4$Cl solution for 5 min at room temperature. The cell suspension were filtered with a nylon mesh and washed twice with staining medium, which was HBSS with reduced phenol red, sodium azide, BSA, and EDTA. 0.5×10$^6$ cells/25 $\mu$l/staining were incubated with 1 $\mu$g/10 $\mu$l/staining of PE- or FITC-labeled antibodies (PharMingen, San Diego, Calif.) for 15 minutes on ice, washed once and fixed with 0.5% formamide in staining medium. Flow cytometry was carried out using an Cytofluorograf IIs flow cytometer and cell sorter (Becton-Dickinson, San Jose, Calif.). A total of 20,000 cells was recorded in each staining.

In vivo Immunization and in vitro T Cell Proliferation and Cytokine Production Assays Eight to ten weeks old wild type and homozygous mutant mice of Black Swiss/129 background were immunized with 150 5 $\mu$g of trinitrophenyl (TNP) coupled to keyhole limpet hemocyanin (KLH), or with 300 5 $\mu$g of TNP coupled to ovalbumin (OVA) in complete Freund's adjuvant via foot pad injection (Coligan , 1994). Both the wild type and mutant mice had at least one H-2$^b$ allele in their genome, as detected by PCR, using primers which amplified an l-Ee$^-$b derived fragment (Mathis , 1983); Dr. Leslie Berg, personal communications).

Ten days after immunization, the lymph node cells were harvested. 2×10$^5$ lymph node cells/well were restimulated in 96-well plates with OVA alone; or with OVA plus 4×10$^4$ T-cell-depleted and irradiated C57BL/6 spleen cells as exogenous antigen presenting cells; or with OVA plus 10 units/ml exogenous IL-2. At 60 hours of stimulation, the culture was pulsed with 1 $\mu$Ci/well $^3$H-thymidine for 6 hours. Experiments were done in triplicate.

T-cell production of cytokines was measured using standard procedures. Lymph node cells from immunized mice were harvested and restimulated with 1 mg/ml OVA in vitro. Supernatants from 2×10$^5$ cells/200 $\mu$l/96-well were harvested after 24 hours. The IL-2 activity in the supernatants was measured by proliferation of HT-2 cells in the presence of IL-4 antibody (11B11). At 24 hours, the HT-2 culture was pulsed with 1 µCi/well of $^3$H-thymidine for 6 hours. Supernatants from 6×10$^5$ cells/2005 µl/96-well were harvested after 60 hours. The amounts of IFNγ in the supernatants were measured by ELISA.

Preparation of T cell Extracts

Spleen and lymph nodes were harvested from wild type and mutant mice and were dispersed into single cell suspension. Red blood cells were removed by lysis. The final concentrations were adjusted to 1.5–2.0×10$^8$ cells suspended in 2 ml of PBS containing 5% fetal calf serum and 4 mM EDTA. The cell suspensions were enriched for T cells using Mouse T Cell Enrichment Column (R&D Systems). T cells were then lysed with lysis buffer containing 50 mM Tris-HCl, pH 7.5, 15% glycerol, 0.1 mM EGTA, 1 mM EDTA, 0.5 mM DTT, 50 5 µg/ml PMSF, 50 µg/ml soybean trypsin inhibitor, 5 µg/ml aprotinin, 5 µg/ml leupeptin. Aliquots of 8×10$^6$ cells per 50 µl of lysis buffer were frozen until further analysis.

Preparation of Brain Extracts

Using a scinterred-glass tissue grinder, a single mouse brain was homogenized in 1 ml buffer containing 50 mM Tris pH7.5, 15% glycerol, 0.1 mM EGTA, 1 mM EDTA, 0.5 mM DTT, 50 µg/ml PMSF, 50 5 µg/ml soybean trypsin inhibitor, 5 µg/ml aprotinin, 5 µg/ml leupeptin, and 0.05% (v/v) NP-40. The extract was subjected to centrifugation (10,000 ×g) and the supernatant was saved at −80° C. until it was assayed. Protein was measured using the Bio-Rad assay and concentrations were typically between 15 and 20 mg/ml.

The amount of calcineurin Aα in T cell extracts was assessed by Western blotting using standard procedures. Twenty micrograms of T cell extract or brain homogenates were fractionated by SDS-PAGE on a 16% Tris/glycine gel (Novex) at 150 volts (constant voltage)and transferred to a PVDF membrane (Immobilon) at 100 volts for 1.5 hours. Following transfer, the membrane was blocked in M-Blotto overnight at 4° C. The membranes were briefly rinsed in PBS and reacted with either rabbit antibody R2929 (specific for C-terminal peptide, SNSSNIQ (SEQ ID NO.:1) from human CNAα) or rabbit antibody R2948 (specific for CNAβ residues 386–396, LMTEGEDEFDG (SEQ ID NO.:2)). Rabbit anti-peptide antiserum was diluted to 1:10,000. The membranes were washed and incubated for 1 hour at room temperature in TBST containing HRP-conjugated donkey-anti-rabbit secondary antibody (Amersham) diluted 1:10, 000. The membranes were washed in TBST and developed with the ECL Western blotting detection system (Amersham).

Calcineurin Phosphatase Assay

The phosphatase assay is a modified version of a previously described procedure (Manalan and Klee, 1983; Liu, 1991). The reaction mixture (total volume 60 µl) contained 50 mM MES (pH6.0), 100 mM NaCl, 6 mM Mg(OAc)$_2$, 100 mM CaCl$_2$, 100 mg/ml BSA (Fraction V), 1.25 mM okadaic acid (Calbiochem), 20 mM [$^{33}$P] RII peptide (600 cpm/pmole), and T cell or brain extract. The reaction mixture was incubated for 20 minutes at 30° C. The reaction was terminated by the addition of 100 ml of ice-cold 5% TCA/0.1 M potassium phosphate (pH 7.0). The precipitate was collected on a MultiScreen IP plate (Millipore). One-quarter (40 ml) of the terminated reaction mixture was applied per well, washed and counted in a Top-Count scintillation counter (Packard Instrument Co.).

The RII peptide (modified from (Manalan and Klee, 1983; Liu, 1991), DLDVPIPGRFDRRVSVAAE. (SEQ ID NO.:3) was phosphorylated at the serine residue with $^{33}$P as follows: The final reaction mixture contained 1.5 mg of the synthetic peptide substrate, 20 mM MOPS (pH 7.0), 2 mM Mg(OAc)$_2$, 1 mM γ-$^{33}$P-ATP (final specific activity 600 cpm/pmol), 13 mM DTT, and 250 units of the protein kinase subunit. 50 ml of 6 mg/ml DTTI was added to 250 units of the protein kinase subunit and, after 10 minute incubation, the DTT/protein kinase mixture was added to the other components to initiate the phosphorylation reaction which was performed at 30° C. for 50 minutes. The phosphorylated peptide was purified on a 1.0 ml Dowes AG-1 X8 column equilibrated in 30% acetic acid and concentrated as described. The final concentration of the labeled peptide would be between 300–400 pmol [$^{33}$P] peptide/ml.

Histology and Immunohistochemistry

Mice were anesthetized with 2.5% avertin and perfused intracardially with Tyrode's solution followed by 4% buffered paraformaldehyde. The brains were removed immediately and postfixed in 4% buffered paraformaldehyde at 4° C. overnight. They were then soaked in 4% buffered paraformaldehyde with 10% sucrose at 4° C. overnight. Two to three pm thick coronal sections of the cerebrum and sections perpendicular to the axis of the brain stem with attached cerebellum and the spinal cord were processed routinely and embedded in paraffin. Sections were stained with hematoxylin and eosin, Luxol fast blue, Bielchowsky silver and cresyl violet (Nissl) stains. To determine areas of representative brain sections, the two maximal dimensions of cerebrum at approximately the level of the optic chiasm and of the mid-pons/cerebellum were measured in the slides and areas calculated for each sample.

Paraffin sections were de-paraffinized and were immunostained using the ABC, and ABC-AP kits according to manufacturer's instructions (Vector, Burlingame, Calif.). To enhance the signal on fixed tissue, occasionally slides were treated with either 88%. formic acid for 10 min or 0.1 M citrate pH 6.0 for 10 min in the microwave (bringing the citrate to boil).

Morris Water Maze Task

Naive adult mice (10–37 weeks old) were utilized. The training apparatus for the spatial version of Morris water maze was a circular polypropylene pool 120 cm in diameter. The escape platform was 11.5 cm in diameter. The maze is divided into four equal quadrants and the escape platform was put at the center of one of the four quadrants. The water was maintained at 78° F. Nontoxic Crayola white powder paint was added to make the water opaque. The pool was located in a room that had a number of items on the walls and inside the room that could be seen by a mouse swimming in the pool. Prior to training, in order for the mice to get used to the water and the escape platform, each mice was allowed to stay on the platform for 30 seconds and to swim around for 1 minute and then to practice climbing the platform 5 times. The genotypes of the experimental subjects were blind to the experimenter.

Hidden-Platform Training

Acquisition: The top of the platform was 1 cm below the surface of the water, which is invisible to the animal swimming in the pool. The platform location varied among different animals, but always remained in the same place for any given mouse. Before each trial, a mouse was put on the platform for 30 seconds. A trial was started by placing an animal along the edge of the pool facing the wall. The start location alternated in 1 of 4 start locations, with each trial in the same day starting at a different start location. A subject was allowed 60 second to locate the platform, with its movement traced by a computer. The time taken to locate the escape platform (escape latency) was determined on each trial. Animals not finding the platform in 60 seconds were guided there by the experimenter and the escape latency was recorded as 61 seconds. After each trial, animals were allowed to remain on the platform for 3D seconds. Animals were given four trials a day for eight consecutive days. Each trial in one block of four trials was separated by 1 hour (distributed trial procedure).

Probe Trial

One hour after the last training trial, each animal was given a probe test. During the probe test, each subject was allowed to stayed on the platform for 30 seconds, then remove the platform from the pool without letting the mice noticing the action. Trial was initiated by placing the mouse slightly off-center opposite to where the platform used to be. Each animal was allowed 60 seconds to search the pool. Two measures of search behavior were determined. A quadrant search time measure was obtained by determining the amount of time spent in each quadrant. A platform crossing measure was obtained by counting the number of times a subject crossed the exact place in the training quadrant in which the platform was located during training. For comparison, the number of times a subject crossed the equivalent location in each of the other quadrants was determined.

Random Platform Test

The next day of the probe trial, mice were given one trial with the platform in its original location and three trials with the platform in one of the platform sites in other three quadrants. The average escape latency to the platform when it was in its original place was used as the trained platform escape latency of the mice, and the average time taken to locate the platform when it was in the three new locations was used as the other platform escape latency of the animals.

Visible-Platform Training

After the hidden-platform task, the same animals were subjected to the visible-platform training. In the visible platform task, the platform was still 1 cm below the water surface, but a flag was attached to the top of the platform to make it visible. The training procedure was the same as in the hidden-platform task, except that the platform position alternated among four possible positions within each block of four trials, and that the starting position was always opposite from the position of the platform. Each mouse was given 12 trials a day, in blocks of four trials for three consecutive days (massed-trial procedure). Each block of four trials was separated by 1 hour.

Fear Conditioning

Adult mice were housed individually for at least 1 week prior to behavioral testing. They were handled every day for 1 week prior to testing to reduce stress. Fear conditioning and context-dependent learning testing were conducted in a small rodent chamber (Coulbourn) containing a stainless steel rod floor (5 mm diameter, spaced 1 cm apart) through which scrambled foot shocks could be administered. The chamber is placed inside a sound-attenuating chest (Coulbourn) with a ventilation fan providing background noise. The chamber was cleaned with 1% acetic acid and dried completely before each animal was placed inside. Freezing was assessed by a time sampling procedure in which an observer blind to mouse genotypes scored each mouse every 2 s. Experiments were videotaped and freezing was assessed again by two observers blind to mouse genotypes.

Context-dependent Fear Conditioning

Some of the animals underwent Morris water maze training (6 wild type and 6 mutants) and some age-matched naive animals (3 wild type and 2 mutant) were subjected to the following context-dependent fear conditioning protocol. In the conditioning phase, animals were placed in the shocking chamber for 3 minutes and subsequently subjected to three foot shocks (0.5 mA intensity, 1 s duration, 1 minute apart). Mice were removed from the chamber 1 minute after the last foot shock. At 1 hour, 2 hours, or 24 hours after the training, animals were returned to the shocking chamber and freezing was monitored for 3 minutes without any foot shocks.

Tone-dependent Fear Conditioning

Naive adult animals (9–17 weeks old) (15 wild types and 14 mutants) were placed in the shocking chamber for 3 minutes and then presented with three 20-second loud tones (approximately 75 db, 1000 Hz, 3 minutes apart) through a speaker mounted on the chamber. A foot shock (0.5 mA intensity, 1 s duration) was presented at the offset of each tone. Mice were removed from the chamber 3 minutes after the last foot shock. At 1 hour, 2 hours, or 24 hours after the training, one group of mice (wild type n-6, mutant n-6) were tested for their tone-dependent learning. Mice were placed in an empty plastic cage different from the shocking chamber (to minimize freezing due to context-dependent conditioning) and freezing was scored for 3 min prior to the tone and subsequently for 3 min in the presence of the tone. Another group of mice (wild type n=9, mutant n-8) were returned to the shocking chamber twenty-four hours later, to test their context-dependent learning. The freezing was monitored for 3 minutes. This group of animals were also tested for their tone-dependent learning forty-eight hours after the training.

Pain Sensitivity Test

Mice were tested for their sensitivity to foot shocks. Animals were put into the conditioning chamber and were given foot shocks (1 s duration) of increasing intensities, from 0.05 mA to 0.40 mA, with 0.05 mA increments. The intensities causing the nociceptive responses, i.e. flinch, run/jump, and vocalization, were determined. All the animals were tested at the same intensity before increasing it, till they vocalized. Experimenter was blind to the genotypes of the subjects.

Electrophysiology

Hippocampal slices from 16–18 days old mice were prepared by standard methods. Experiments were conducted at 27–29° C. in normal ringer containing 2.5 mM calcium, 1.3 mM magnesium with no picrotoxin added. Two path experiment protocol was used to allow LTP and LTD to be recorded from the same slice, in which two stimulating electrodes were placed in the stratum radiatum in CA1 at either end with the recording electrode in between the two stimulating electrodes. LTD was induced by 1 Hz, 10 minutes stimulation. LTP was induced with 100 Hz, 1 second tetanus given twice with a 20 seconds inter stimulus interval.

Statistical Analysis

Data from hidden-platform Morris water maze task have a great portion of cercored measurements, thus an analysis of variance (ANOVA) applied to the original data is inappropriate. We treated the escape latency as a binary observation, then fit a generalized linear model for this binary data using statistical software GLIM or Splus. Data from visible-platform Morris water maze task were subjected to logarithm transformation before ANOVA was performed. Since the fear conditioning freezing data are binomial data, we first used a standard arc sine transformation on the data to stabilize the variance. ANOVA was performed on arcsine of the square root of percentage of freezing.

EXAMPLE 1

Generation of CNA$\alpha^{-/-}$ Mice

Calcineurin A$\alpha$ knockout mice (CNA$\alpha^{-/-}$) were produced by standard methods (Bradley, 1987)involving homologous recombination in embryonic stem (ES) cells. The gene targeting vector was constructed by inserting the neomycin phosphotransferase (neo) gene into an exon which encodes part of the calcineurin catalytic domain and by inserting the thymidine kinase gene (tk) outside the region of homology. Linearized construct DNA was transfected into J1 ES cells and colonies were selected for neomycin and FIAU resistance (Li, 1992; Mortensen , 1992). DNA from individual clones was analyzed by Southern blot analysis following digestion with MscI and hybridization with the 1.2 kb probe. A novel 7.5 kb fragment, as well as the 18 kb fragment found in wild-type ES cell DNA, were found in CNA$\alpha^{+/-}$ ES cell DNA. Heterozygous CNA$\alpha^{+/-}$ ES cells were then injected into C57BL/6 blastocysts and some of the resultant chimeric mice passed the mutated gene onto the next generation when mated with Black Swiss mice. CNA$\alpha^{-/-}$ mice were obtained by mating the heterozygous CNA$\alpha^{-/-}$ mice.

Generation of CNA$\alpha^{-/-}$-RAG-2$^{-/-}$ Chimeras

CNA$\alpha^{+/-}$ ES cells were grown in a high concentration of G418 to select for ES cells lacking both copies of functional CNA$\alpha$ genes (Mortensen , 1992). ES cell clones surviving in 1.5 mg/ml G418 were picked and analyzed by Southern analysis. The CNA$\alpha^{-/-}$ clone DNAs were identified because they lacked the endogenous 18 kb MscI fragment.

Double knockout ES cells were injected into RAG-2$^{-/-}$ blastocysts of either B6/129 or FvB background to generate somatic chimeras (Chen , 1993). In the RAG-2$^{-/-}$ mice, there are no mature T and P cells due to their inability to undergo gene rearrangement (Shinkai, 1992). Therefore, in the RAG-2$^{-/-}$ chimeras, all the mature T and B cells should come from the injected ES cells, which were CNA$\alpha^{-/-}$.

The functional disruption of the calcineurin A$\alpha$ gene was confirmed by lack of CNA$\alpha$ expression in double knockout ES cells. RNA from wild type, CNA$\alpha^{+/-}$, and CNA$\alpha^{-/-}$ ES cells were characterized by Northern blot analysis using the 5' end of CNA$\alpha$ cDNA (nucleotides 95–714) as probe. CNA$\alpha$ mRNA was detected in wild-type ES cells and in CNA$\alpha^{+/-}$ ES cells, but not in CNA$\alpha^{-/-}$ ES cells.

Calcineurin Activity in CNA$\alpha^{-/-}$ T Cells

The calcineurin activity in these cells was measured by Western blotting and enzyme activity assays. Wild-type and CNA$\alpha^{-/-}$ derived T cell extracts were fractionated on SDS-polyacrylamide gels, transferred to a membrane and the calcineurin A$\alpha$ and A: polypeptides identified using calcineurin A subunit $\alpha$-isoform or $\beta$-isoform specific antibodies. There was no detectable CNA$\alpha$ polypeptide in T cell extracts from the CNA$\alpha^{-/-}$ mice, while CNA$\alpha$ was readily detectable in wild type T cell extracts. CNA$\beta$ peptide was not detected in either wild type or mutant T cells with the $\beta$-isoform specific antibody, even though CNA$\beta$ peptide could be readily detected in the brain.

Residual calcineurin activity, (i.e., okadaic acid resistant and EGTA-sensitive phosphatase activity) was measured in the same CNA$\alpha^{-/-}$ T cell extracts (Martin and Wiederrecht, in press). Calcineurin's phosphatase activity in CNA$\alpha^{-/-}$ T cells extracts (169±32 pmols substrate/minute/mg protein) was 34% of the activity found in wild type T cell extracts (500±77 pmols substrate/minute/mg protein). The phosphatase activity in both the wild type and mutant T cells was 90–95% inhibited by FK506.

Normal Development of T and B Lineage Cells

CNA$\alpha^{-/-}$ T and B cells were phenotypically normal, and the composition and distribution of different subsets of T and B lineage cells were normal in the thymus, spleen, lymph nodes, and bone marrow in the CNA$\alpha^{-/-}$ mice, as indicated by staining with antibodies to TCR$\alpha\beta$, TCR$\gamma\delta$, CD3, CD4, CD8, MHC Class I and II, Thy-1, IL-2R$\alpha$, B220, IgM, IgG, IgD, IgA, IgE, CD23, S7 and Ly-1. Compared to the wild type littermates, CNA$\alpha^{-/-}$ mice have normal populations of double negative (CD4–CD8–), double positive (CD4+ CD8+), and single positive (CD4+CD8– or CD4–CDB+) thymocytes. Staining with different V$\beta$ antibodies (V$\beta$5, V$\beta$6, V$\beta$8, V$\beta$9, Vp$\beta$11, V$\beta$13, V$\beta$14) showed that these V$\beta$ representations in the mutant thymus were the same as the wild type control. These findings indicated that a functional CNA$\alpha$ gene is not required for the maturation of both T and B lymphocytes. CNA$\alpha^{-/-}$ T cells respond normally to mitogens in vitro and remain sensitive to CsA and FK506

We tested the responses of the wild type and mutant T cells to mitogenic stimulation with phorbol 12-myristate 13 acetate (PMA) plus ionomycin, concanavalin A (ConA), and anti-CD3$\epsilon$ antibodies. All three mitogens induced the CNA$\alpha^{-/-}$ T cells to proliferate as rapidly as the wild type T-cells. Further, stimulated mutant and wild type T cells produced the same amounts of IL-2 and IL-4 and expressed normal level of IL-2 receptor on the surface. Thus, CNA$\alpha^{-/-}$ T cells appeared to be functional when stimulated by mitogens in vitro.

Calcineurin, especially calcineurin containing the A$\alpha$ subunit, has been implicated as the target for immunosuppressive drugs CsA and FK506, which inhibit the TCR mediated proliferation and IL-2 production of normal T cells (O'Keefe , 1992; Clipstone and Crabtree, 1992; Frantz, 1994; Tsuboi , 1994). We tested the drug sensitivity of the CNA$\alpha^{-/-}$ T cells. When stimulated with PMA plus ionomycin, ConA, or $\alpha$CD3$\epsilon$ antibody, CNA$\alpha^{-/-}$ T cells and wild type T cells were both inhibited by CsA and FK506, as measured by proliferation and by IL-2 and IL-4 production. CNA$^{-/-}$ T cells were even more sensitive to these drugs than normal T cells, with a IC$_{50}$ of 2–7 fold lower than that of the wild type T cells.

Defective T Cell Responses to Protein Antigens

To determine if CNA$\alpha$ is required for a normal immune response, we measured the responses of wild-type and CNAα$^{-/-}$ mice to hapten-protein antigens. Wild type and CNAα$^{-/-}$ mice were immunized with TNP-KLH, or TNP-OVA via foot pad injection (Coligan, 1994). Ten days after immunization, the lymph node cells were harvested. The total number of cells in the lymph nodes were similar in the immunized wild type and mutant mice, which were much more than that in the lymph nodes of non-immunized animals. Also, the CD4$^+$:CD8$^+$ ratio was the same in lymph nodes from the two types of mice. We concluded that the wild type and mutant mice T cells were both primed during the 10 days of immunization. However, after re-stimulation in vitro with KLH or OVA, T cells from wild type mice proliferated much more rapidly than T cells from CNAα$^{-/-}$ mice.

Addition of normal antigen presenting cells or IL-2 to the in vitro cultures did not complement the proliferative defect of CNAα$^{-/-}$ T cells.

The defect in the antigen specific T cell response could be due to either a defect in CNAα$^{-/-}$ T cells or to a defect in other cells whose function is required for the priming of antigen specific T cells during the immunization process. To distinguish between the two possibilities, we immunized the RAG-2$^{-/-}$CNAα$^{-/-}$ chimeras with TNP-OVA and restimulated the lymph node cells with the immunogen after 10 days. CNAα$^{-/-}$ T cells in the RAG-2-CNAα$^{-/-}$ chimeras did not proliferate as well in response to the immunogen. In these RAG-2-CNAα$^{-/-}$ chimeras, the CNAα$^{-/-}$ ES cells comprised about 10 percent of the chimeric animals, as judged by coat color contributions. Only T and B cells in the chimeras were completely CNAα deficient since they were derived from the injected CNAα$^{-/-}$ ES cells, while up to 90% of other cell types were derived from the RAG-2$^{-/-}$ CNAα$^{+/+}$ background.

B cell function was assessed in CNAα$^{-/-}$ mice and in RAG-2$^{-/-}$-CNAα$^{-/-}$ chimeric mice immunized with TNP-KLH or TNP-OVA Similar serum titres of anti-TNP antibodies (IgG1 and IgG2a) were found in immunized wild-type, CNAα$^{-/-}$ mice and the immunized RAG-2$^{-/-}$-CNAα$^{-/-}$ chimeric mice.

Upon restimulation with the immunogens, the lymph node T cells from immunized CNAα$^{-/-}$ mice secreted significantly less IL-2, IL-4, and IFNγ than the lymph node T cells from immunized normal mice (Table 1 and data not shown). IFNγ was detected in the TNP-OVA immunized RAG-2 chimeras, at a level much higher than the mutant mice but lower than the wild type mice (data not shown), most likely because in the RAG-2 chimeras some IFNγ secreting cells, such as NK cells, were from the RAG-2$^{-/-}$ CNAα$^{+/-}$ background and were able to secret IFNγ.

TABLE 1

IL-2 and IFNγ secretion by wild type and CNAα$^{-/-}$ T cells.

| Mouse # | Genotype | IL-2 | IFNγ |
|---|---|---|---|
| 2741 | +/+ | nd | 799 |
| 2752 | +/+ | nd | 982 |
| 2768 | +/+ | 7.6 | 622 |
| 2769 | +/+ | 7.5 | 33 |
| 2802 | +/+ | >16 | 537 |
| 2838 | +/+ | 15.4 | 358 |
| 2841 | +/+ | >16 | 257 |
| 2740 | -/- | nd | 0 |
| 2751 | -/- | nd | 0 |
| 2736 | -/- | 0.7 | 164 |
| 2764 | -/- | 0.7 | 0 |
| 2806 | -/- | 4.2 | 0 |
| 2791 | -/- | 0.4 | 0 |

Table 1. Wild type and CNAα$^{-/-}$ mice were immunized with 300 μg of TNP-OVA. At day 10, lymph node cells were harvested and restimulated with 1 mg/ml OVA in vitro. Supernatants from 2×10$^5$ cells/200 μl/96-well were harvested after 24 hours. The IL-2 activity in the supernatants was measured by proliferation of HT-2 cells in the presence of αIL-4. antibody (11B11). At 24 hours, the HT-2 culture was pulsed with 1 μCi/well of $^3$H-thymidine for 6 hours. Supernatants from 6×10$^5$ cells/200 μl/96-well were harvested after 60 hours. The amounts of IFNγ in the supernatants were measured by ELISA. Lymph node cells cultured without antigen did not produce detectable lymphokines. (nd, not determined). CNAα$^{-/-}$ T cells secreted significantly less IL-2 (ave. wildtype=12.5 units of IL-2 activity vs ave. CNAα$^{-/-}$= 1.5; p<0.003) and IFNγ (ave. wild-type=513 units of IFNγ activity vs ave. CNAα$^{-/-}$=27; p<0.005) than the wild type T cells.

Discussion

We have generated a CNAα$^{-/-}$ mouse by structurally inactivating the CNAα gene, resulting in the disruption of CNAα expression. We demonstrate here that there was more than 65% reduction of calcineurin activity in the CNAα$^{-/-}$ T lymphocytes. B and T-cell development in these mice appears to proceed normally. The mutant mice have a normal B-cell response but a defective T-cell response in vivo. The immune response of RAG-2/CNAα$^{-/-}$ chimeric mice is also defective suggesting that T-cells per se are defective and not some other aspect of the immune response. Further, mutant T-cells remained sensitive to FK506 and CsA. These mice provide information about the physiologic roles of calcineurin Aα and Aβ and suggest that these two polypeptides have non-identical roles in T-cell development and function.

Previous studies and our own data showed that α is the predominant isoform of the two major calcineurin A subunit isoforms, α and β (Takaishi, 1991; Kuno, 1992; Guerini and Klee, 1991;). In T-cells, Aα accounted for at least 65% of calcineurin expression and activity in these cells. The residual calcineurin-like activity in the mutant T cells could be contributed by other calcineurin isoforms or by other related phosphatases. In the thymus, Aα is also the predominant isoform, because when we screened a murine thymocyte cDNA library under low stringency conditions with full length CNAα cDNA, we were not able to pull out any Aβ clones, while Aα clones were abundant (unpublished data). In the absence of the CNAα, CNAβ doesn't seem to be upregulated, arguing against the possibility that CNAβ is substituting CNAα's function in its absence.

CNAα is required for a normal in vivo antigen specific T cell response. The defect in proliferative T cell response is not due to lack of normal antigen presentation, because the addition of exogenous wild type antigen presenting cells at the time of in vitro restimulation could not complement the proliferation defect. Also, in the immunized RAG2 somatic chimeras, there was normal antigen presentation function, because only the mature T and B cells were derived only from the injected ES cells, which were CNAα deficient, while the other cell types, including antigen presenting cells, were mostly RAG-2$^{-/-}$ CNAα$^{+/+}$. The proliferative defect also existed in the immunized RAG-2 somatic chimeras, suggesting that the defect was in T cells per se instead of other cell types that might be important for the proper immunizations.

When restimulated with the immunogens in vitro, CNAα$^{-/-}$ T cells failed to secret IFNγ (Table 1). This is in agreement with the findings that CsA and FK506 inhibit IFNγ mRNA expression (Reem, 1983; Tocci, 1989), suggesting that CNAα is required for IFNγ production. Also, CNAα$^{-/-}$ T cells secreted significantly reduced amounts of IL-2 and IL-4 (Table 1 and data not shown), confirming the in vitro studies in which CsA and FK506 were shown to inhibit IL-2 and IL-4 production (Bierer, 1991; Bloemena, 1988; Bloemena, 1989; Dumont, 1990; Herold, 1986; Hess, 1982; Johansson and Moller, 1990; Kumagai, 1988; Lin, 1991; Mattila, 1990; Orosz, 1982; Reem, 1983; Sawada, 1987; Schreiber, 1992; Schreiber and Crabtree, 1992; Siekierka and Sigal, 1992; Sigal and Dumont, 1992; Tocci, 1989). The data suggested that in vivo, calcineurin α is required for the normal expression of IL-2, IL-4, and IFNγ.

Interestingly, CNAα$^{-/-}$ B cells responded normally to TNP-OVA and TNP-KLH, suggesting the T cell help for the antibody response was normal. Why the T cells having a defective antigen specific proliferation response still could provide normal help to B cells for antibody production is unclear. It is possible that even though the mutant T cells proliferated slower and produced reduced amount of lymphokines, the smaller amount of lymphokines and the smaller number of activated T cells present were sufficient enough to help the B cells to mount a normal antibody response.

The defective in vivo T cell response might have been due to defects in T cell development, because calcineurin is thought to play a role in T-cell development. It was shown that CsA inhibits the development of mature single positive (CD4$^+$8$^-$ or CD4$^-$8$^+$) TCR-αβ$^+$ thymocytes (Jenkins, 1988; Gao, 1988). CsA also interferes with the deletion of cells bearing self-reactive TCRs in the population of single positive thymocytes that do develop, possibly by inhibiting TCR-mediated activation-induced cell death (Jenkins, 1988; Shi, 1989). However, thymocyte development appeared normal in CNAα$^{-/-}$ mice, which have a normal composition of mature and immature T-cells in the thymus and normal Vβ usage. Furthermore, neither the CNAα$^{-/-}$ mice nor the RAG-2-CNAα$^{-/-}$ chimeras were associated with autoimmune reactions (our unpublished observations). CNAα is not absolutely required for the maturation of thymocytes and probably not required for mediating the effect of CsA on thymocyte development into single positives and on negative selection of autoreactive thymocytes. However, we cannot rule out the possibility that even though the mutant T cells are phenotypically normal, they are somehow anergized after thymic selection and thus cannot mount a normal in vivo T cell response.

Even though CNAα is required for in vivo T cell response, it is not required for a normal in vitro T cell response to mitogens. CNAα$^{-/-}$ T cells responded normally to in vitro mitogenic stimulation. This result appears to contradict previous findings which implicated CNAα in the TCR mediated proliferation and IL-2 production (O'Keefe, 1992; Clipstone and Crabtree, 1992; Frantz, 1994; Tsuboi, 1994). Perhaps calcineurin Aα is normally involved in transducing the TCR-mediated signals, but αCD3ε and ConA might provide much stronger signals than antigen. That is, these mitogens might engage other signaling pathways and thus obfuscate the loss of calcineurin Aα's function.

Proliferation and lymphokine production of CNAα$^{-/-}$ T cells were still fully inhibitable by both CsA and FK506, suggesting other proteins can mediate the drugs' immunosuppressive effect. One of these proteins could be the calcineurin Aβ subunit. When CNAβ is over expressed in Jurkat cells, it has the same biological activities as overexpressed Aα subunit (Dr. Stephen J. O'Keefe, unpublished results). Further, 90–95% of the residual calcineurin activity found in CNAα$^{-/-}$ T cells, which is most likely contributed by CNAβ, is FK506 sensitive. Both of these observations suggest that CNAα$^{-/-}$ can serve as an immunosuppressive drug target in the CNAα$^{-/-}$ T cells. Other proteins could also mediate CsA and FK506 inhibition, because the non-calcineurin mediated and activation-induced IL-2 production in T cell line 171 was inhibited by both CsA and FK506 (Metcalfe, 1994). However, CNAα$^{-/-}$ T cells had increased sensitivity to both CsA and FK506, suggesting that under normal conditions, i.e. in wild type T cells, CNAα is the primary target of the drug-immunophilin complex, probably due to the predominant presence of the CNAα protein in T cells.

The finding that CNAα$^{-/-}$ mice have a marked deficiency in T cell immunity suggests that calcineurin a may be a relevant isoform of calcineurin that mediates immunosuppression in transplantation patients who are treated with CsA or FK506. However, other targets for these drugs remains because CNAα$^{-/-}$ T cells are sensitive to FK506 and CsA. We imagine that calcineurin Aβ might replace some of the functions of CNAα. However, Aα subunit has unique physiological functions because the CNAα$^{-/-}$ mice have defects in T cell immunity and in other physiological processes.

EXAMPLE 2

Calcineurin Aα, A Target for CsA and Fk506, is a Key Signaling Molecule in Long Term Memory Formation Calcineurin Aα (CNAα) knockout mice were generated by standard homologous recombination technique and ES cell manipulations as described in Example 1. Homozygous mutants are not sterile, but are extremely poor breeders. Therefore, the homozygous mutants studied were generated by mating the heterozygous mutants, which are of Black Swiss/129 background. The wild type littermates from these heterozygote matings were used as the wild type controls in the studies presented here. (Hereafter, homozygous CNAα knockout mice are referred to as mutants, and the wild type littermate controls are referred to as wild type). Lacking of Calcineurin Aα Protein And Phosphatase Activity in The Mutant Brain Did Not affect its Development.

Insertion of a copy of neo gene into an exon of calcineurin Aα leads to structural disruption of the gene and of mRNA transcription. Western blot analysis of whole brain homogenates with a calcineurin Aα specific peptide antibody showed that there was no calcineurin Aα protein being expressed in the mutant brain, while calcineurin Aα was very abundant in the wild type brain. The same amount of homogenates were also probed with a calcineurin Aβ specific peptide antibody. There was similar amount of calcineurin Aβ present in the mutant and wild type brains. We also measured the calcineurin activity, i.e. the okadaic acid resistant and ECTA-sensitive phosphatase activity, in the brain. The calcineurin phosphatase activity was greatly reduced in the mutant brain. The residual calcineurin activity in the mutant brain might be contributed by calcineurin Aβ or other calcineurin isoforms.

As shown by other people and our own data, calcineurin Aα is the predominant isoform of calcineurin A subunit in the brain, consisting more than 85%. of total calcineurin protein and more than 85% of the calcineurin phosphatase activity (Takaishi, 1991; Kuno, 1992). In the absence of calcineurin Aα, the expression and activity of Aβ isoform were not upregulated, suggesting that Aα and Aβ have distinct physiological functions of their own, and that Aβ is very unlikely substituting Aα for its functions in the mutant brain.

The mutant brains are smaller than that of the wild types. The average wild type brain weighs 494.4 mg (n=5), while the average mutant brain weighs only 408.8 mg (n=4), 85.7 mg lighter in weight. The density of the mutant brains were higher than that of the wild type brains. After being fixed in 4% paraformaldehyde at 40° C. overnight and transferred to 10% sucrose in 4% paraformaldehyde, the mutant brains sunk to the bottom while the wild type brains floated (n=4 of each). Determined by very crude method, the volume of the mutant brains were about O.15ml smaller than the wild type's, while they were only 63 mg lighter in weight, resulting in 0.175 g/ml higher in density (after 4% paraformaldehyde fixation).

Histological studies revealed no gross malformations or other anomalies in the mutant brains (data not shown). There were no differences detected in general architecture, neuronal morphology, or neuronal numbers in the cerebral cortex, subcortical nuclei, including the amygdala, or spinal cords. No neurofibrillary tangles or other cytoplasmic abnormalities of neurons or of other cell populations were identified and myelination appeared to be normal throughout the central nervous system in both wild type and mutant mice. However, the mutant brains, particularly the cerebellums, appeared to be smaller than those of the wild type littermates. By measuring the cross-sectional areas ($mm^2$), the cerebral hemispheres in the mutants seemed to be slightly smaller than those in the wild type, but the differences were not statistically significant (wild type 53±4.8, n=5; mutant 50.3±4.8, n=5; p=0.43). In the cerebellums and brain stems, there were no specific differences among neuronal or other cell populations, but these structures appeared to be smaller overall (wild type 44.5 ±3.8, n=5; mutant 36.8±4.1, n=5; p=0.0012) and the density of the fiber tracts appeared to be less in the mutant mice compared to the controls (data not shown). Phenotypes of The Mutant Mice Resemble The Manifestations of CsA and FK506's Neurotoxicity Mutant mice were indistinguishable from the wild type or heterozygote littermates when weaned at three weeks old. They groom and feed normally. However, they showed some phenotypes similar to the manifestations of CsA and FK506's neurotoxicity previously described. The mutant mice had a motor coordination deficit (ataxia). There were severe tremors and errors in the metrics of movements in the mutants. This motor deficit was not affecting all the mutants to the same extend. Some mutants showed much more severe motor problem than others. This phenomenon also became more evident when the animals got older. Compare to the wild types, the mutant mice had abnormal gaits. They could not walk in a straight line and had uneven paces. Their hind limbs tend to be dragged behind on the ground and then moved almost simultaneously instead of alternating. Severe seizures were observed in the mutants. Many of the mutants also experienced weight loss.

During our characterization of the $CNA\alpha^{-/-}$ mice we recognized that these mice had a reduced life expectancy. When scored at three weeks old, there were significantly fewer (15%) homozygous $CNA\alpha^{-/-}$ offspring resulting from intercrosses between heterozygote parents ($CNA\alpha^{-/-} \times CNA\alpha^{-/-}$) than expected (25%, $p<10^{-30}$). Surviving $CNA\alpha^{-/-}$ mice underwent grossly normal development, however their life expectancy is dramatically shortened. These mice were bred in a virus free facility where other immunodeficient (RAG-2 deficient) mice had a normal life expectancy (our unpublished observation). Pathological studies revealed no evidence of consistent pattern of infection or auto-immune reactions (unpublished observations). Therefore, CNAα is playing a critical role in some physiological processes that are essential for extended survival although it is not absolutely required for development.

Defective Spatial Learning in The Morris Water Maze Task

Using the Morris water maze tasks (Morris, 1981; Brandeis, 1989), we tested the mutant mice for their spatial learning abilities, a form of learning which requires an intact hippocampus (Morris, 1982; Sutherland, 1982). In this task, animals are placed in a round pool of opaque water, and they learn to escape the water by swimming to a platform. In the spatial version of the Morris water maze task, the platform is submerged in the water, and the animals have to learn the location of the hidden platform relying on the spatial cues provided by distal visual objects surrounding the pool. During each trial, the animal is placed in the pool at one of the four start sites and the platform position for each individual mouse remains constant throughout training. In the non-spatial version of the Morris water maze task, the platform is made visible to the animals swimming in the pool by placing a flag on top of the platform. For each trial, animals were placed in the pool at one of the four start positions, while the platform was alternating in one of the four platform positions. In this task, animals need to learn to associate the flag with the position of the platform, and spatial information is irrelevant. The hidden-platform and visible-platform versions of the Morris water maze tasks are similar in terms of motivation and the requirements for vision and for swimming ability. There-fore, the visible platform task serves as an important control for the hidden-platform test.

We started by testing the wild type (n=11) and mutant (n=10) mice in the hidden-platform test with one block of four trials each day, with each trial separated by one hour. The training lasted for eight days. On the eighth day, one hour after the last training trial, each animal was given a probe test, in which the platform was removed from the pool and each animal was allowed 60 seconds to search for the platform. The next day of the probe trial, mice were given a random platform test, i.e. one trial with the platform in its original location and three trials with the platform in one of the platform sites in other three quadrants. Twenty-four hours later, these animals were subjected to visible-platform test with three blocks of four trials each day, nine blocks of training in total. Data was analyzed after all the training were finished.

In the visible-platform test, both the wild types and mutants split into two groups. One group (wild type n=10; mutant n=5) could locate the visible platform with a reasonable latency while the other (wild type n=1; mutant n=5) could not, most likely due to the lack of motivation to escape and, for the mutants only, the motor deficit. Both the wild type and mutant mice capable of performing the visible platform task should have similar motivation to escape, the vision to see, and the motor skill required to swim to the platform. So, only the data from those mice which could performed the visible-platform task were analyzed and the others were excluded.

There is no significant difference between the wild types (n=10) and mutants (n=5) in the performance of visible-platform task (p=0.248), even though at the beginning of the training, it took the mutants longer time to reach the platform. However, in the hidden-platform test, the overall performance of the wild types was significantly better than that of the mutants (p<0.00001). The mutants did not learn how to locate the submerged platform (p=0.956) after 32 training trials, while the wild types improved significantly by training (p<0.00001).

In the probe test, in which the platform was removed from the pool, the wild types spent significantly more time searching the target quadrant, where the platform had been, than that spent in the other three quadrants (p<0.001), while the mutants did not search preferentially the target quadrant (p=0.41). Also, in the probe test, the wild types crossed the target platform position significantly more times than the corresponding positions in the other three quadrants (p<0.03), while the mutants did not cross the target platform position more than the others (p=0.39). In the random platform test, the latencies to locate the platform at its original position (target) or at other three new locations (other) were determined. The wild type mice found the platform at its original position much faster than the other positions (p<0.001) while there was no difference for the mutants (p=0.47). All these tests confirmed that using our training protocol, the wild type controls learned and remembered to locate the platform using spatial cues, and the mutants did not.

Fear Conditioning Studies

Fear conditioning is a form of associative learning in which an emotionally neutral conditioned stimulus (CS), such as a tone, a light, or the distinct environment (context) in which the events happen, is paired with an aversive unconditioned stimulus (US), such as a foot shock. The CS, by virtue of its relationship with the US, acquires aversive properties and comes to elicit responses characteristically elicited by aversive stimuli, i.e. freezing, defecation, piloerection, etc. (Blanchard and Blanchard, 1969; Bolles and Fanselow, 1980). In the contextual fear conditioning, the CS is the context in which the animals were exposed to the US, and this type of learning is dependent on both hippocampal and amygdala functions (Kim, 1993; Phillips and LeDoux, 1992). In cue-dependent fear conditioning, the CS is a tone related to the US in a temporal fashion, and this type of learning is dependent on amygdala but not hippocampal functions (Kim, 1993; Phillips and LeDoux, 1992). We examined the performance of the mutant mice in both context- and tone-dependent fear conditioning tests.

Since changes in pain sensitivity were shown to affect freezing performance (Fanselow and Bolles, 1979; Fanselow and Bolles, 1979; Fanselow, 1986), it was important to determine if mutants had altered nociceptive responses to foot shocks, i.e. flinch, run/jump, and vocalization. There was no significant difference in the shock intensities causing the wild types and the mutants to flinch and vocalize (flinch, p=0.71; vocalization, p=0.94). Actually, the intensity causing the mutants to run/jump was lower than that for the wild types (p=0.012). This suggested that the pain sensitivity of the mutants were normal, if not slightly more sensitive than the wild type controls. Thus, their lack of freezing in the fear conditioning tests could not be caused by changes in pain sensitivity.

Learning and Memory in Tone-dependent Fear Conditioning

In the tone-dependent fear conditioning, wild type and mutant animals were placed in the shocking chamber for three minutes and then presented with three 20-second loud tones (CS) (3 minutes apart) and a foot shock (US) at the offset of each tone. One hour, two hours, or twenty-four hours after the initial training, animals were tested in a different chamber to minimize the confounding effect of contextual conditioning. They were allowed to stay in the novel chamber for three minutes before the onset of tone, which lasted for three more minutes. Freezing was monitored by a time sampling method.

The wild type and mutant mice behaved similarly during and immediately after the training (p=0.396), and the training effect was strong for both groups (p<0.000001), suggesting there is no difference between the wild types and mutants in their associative learning ability and short-term memory. When tested at one hour after training, compared to the first three minutes without the tone, the wild types had significantly increased freezing at the onset of tone (p=0.0011), indicating the presence of tone-dependent memory. The mutants also showed some tone-dependent memory as evidenced by an increase in freezing at the onset of tone (p=0.0034), but this should be regarded as marginally significant since the statistics is inaccurate when their percentages of freezing were very small. At one hour after the training, there was a significant decrease in tone-dependent memory for the mutants when compared to the wild types (p=0.0025).

When tested at two hours or twenty-four hours after the training, the wild type also showed significantly increased freezing at the onset of the tone (p=0.026 and p=0.011 respectively), while the mutant did not (p=0.731 and p=0.888), suggesting the little tone-dependent memory present in the mutants at one hour after training was totally lost by two hours after training. Compared to the wild types, the mutants showed a defective tone-dependent memory at both two and twenty-four hours after training (p=0.0043 and p<0.00001, respectively).

At two hours, the wild types showed significantly more tone-dependent freezing than that at one hour, suggesting the consolidation of memory (Rozin, 1976; Squire, 1984; Zerbolio, 1969; Rudy and Morledge, 1994; Kim, 1992). There was no difference between their performances at two and twenty-four hours after training. There was no significant difference of mutants' performance between either one and two hours or two and twenty-four hours (p=0.183 and p=0.473, respectively).

Learning And Memory in Contextual-dependent Fear Conditioning

In the context-dependent fear conditioning, wild type and mutant animals were placed in the shocking chamber (CS) for three minutes and then presented with three foot shocks (US) (1 minute apart). At one, two, and twenty-four hours after training, mice were returned to the shocking chamber to test their context-dependent memory for four minutes.

Both the wild type and mutant mice showed context-dependent learning with the three-foot-shock protocol (wild type p=0.015, mutant p=0.013). Overall, there was no significant difference between the wild type and mutant mice in their performance during the training (for the learning curves, p=0.497; for the freezing responses in the three minutes after the onset of the first foot shock, p=0.158). However, even though the mutant and wild type showed no significant differences in freezing at the 4th and 5th minute (p=0.38 and p=0.43, respectively), the mutant mice froze less than the wild type at the 6th minute (marginally significant, p=0.050), suggesting a very mild deficit in contextual learning in the mutant.

When tested at one hour after the training, there was no significant difference in the freezing to the context between the wild type and mutant mice (p=0.109), suggesting similar retention of the context-dependent memory in both groups. However, there seemed to be a mild trend for the mutants to freeze less than the wild types, Which may due to the mutants' mild deficit in learning. When tested at two and twenty-four hours, the mutants showed significantly less freezing than the wild types (p=0.011 and p=0.0043, respectively). However, there was no decrease in the freezing response for the mutants between one and two hours after training (p=0.78). Therefore, the significant difference between wild type and mutant at two hours might be caused by the slight increase in wild type's response (p=0.08), due to memory consolidation process (Rozin, 1976; Squire, 1984; Zerbolio, 1969; Rudy and Morledge, 1994; Kim, 1992). There was a significant decrease in the freezing response for the mutants between two and twenty-four hours (p=0.023), while the wild types' responses remained similar (p=0.29). This suggested that the mutants started to lose their memory between two and, twenty-four hours, mostly likely due to their inability to consolidate information into long-term memory.

Discussion

CNAα is Mediating CsA and FK506's Neurotoxicity

CsA and FK506 have been used successfully to prevent graft rejections in tissue transplantations (Schreiber and Crabtree, 1992; Siekierka and Sigal, 1992). These drugs bind to their perspective binding proteins, cyclophilins and FK506 binding proteins (FKBPs), collectively called immunophilins. The drug-immunophilin complex binds to calcineurin and inhibit calcineurin's phosphatase activity (Liu, 1991), thus asserting their immunosuppressive effects. However, the use of these drugs also associated with severe side effects, primarily neuro- and renal-toxicity (Siekierka and Sigal, 1992). It is very important to determine whether the immunosuppressive functions of these drugs and their side effects are mechanistically linked. The information would be useful for treating transplantation patients with immunosuppressive drugs and for the design of better immunosuppressive drugs with less side effects.

The CNAα deficient mice showed symptoms similar to CsA and FK506 induced neurotoxicity, including changes in brain density, severe tremor, seizures, cerebellar ataxia, behavioral disorders, weight loss, and increased mortality (Miach, 1986; Wilson, 1988; Labar, 1986; Atkinson, 1984; Menegaux, 1994; Rodriguez, 1992; Appleton, 1989; Lane, 1988; Reece, 1991; Truwit, 1991). We suggest that CNAα is a mediator of the drugs' neurotoxicity. We also have demonstrated previously that CNAα was a relevant isoform in mediating the drugs immunosuppressive effect on T cells. Thus, CsA and FK506's immunosuppressive functions and neurotoxicity are mechanistically linked, i.e. by inhibiting CNAα's phosphatase activity.

It was suggested that the neurotoxic effects of CsA were mediated by metabolites, through an effect on the blood-brain barrier (Lane, 1988). But CsA was found in every mouse organ assayed, including the brain, after subcutaneous administration of the drug, in a dose-dependent fashion (Boland, 1984). This suggested the drug was capable to cross the blood-brain barrier, depending on its serum concentrations. In the brain, FKBP12 (a twelve kilodalton FK506 binding protein) and cyclophilins were found abundant and colocalizing with calcineurin (Steiner, 1992; Dawson, 1994; Snyder and Sabatini, 1995). The colocalization of FKBP12 and cyclophilin with calcineurin would enable them to bind to the drugs entered the brain and to mediate their inhibition of calcineurin, thus causing the neurotoxicity. FKBP12 localizations are almost exclusively neuronal with marked regional variations resembling those of calcineurin, while even though cyclophilin localizations are also quite similar to that of calcineurin, there are some brain areas enriched in cyclophilin that lack calcineurin (Steiner, 1992; Dawson, 1994; Snyder and Sabatini, 1995). The difference between FKBP12 and cyclophilin localization would predict that FK506 has more severe side effects. FK506 indeed has more severe neurotoxicity than CsA (Anonymous, 1994; Mueller, 1994). These findings support our own that CNAα mediates CsA and FK506's neurotoxicity.

It was previously suggested that the emulsifier for CsA in clinical i.v. formulations, Cremophor EL, accounted for nearly all the neurotoxicity of clinically formulated CsA, in terms of effects on elaboration of neurites by N1 E.115 neuroblastoma cells (Brat, 1992). In the clinical sense, it is worth emphasizing that even though the emulsifier may also contribute to the neurotoxicity, the actions of CsA and FK506 themselves, i.e. inhibition of CNAα activity, can cause severe neuronal side effects.

When various blood and serum parameters, including ALT, bilirubin, urea, creatinine, and glucose, were analyzed alone or in multivariate fashion, they correlated significantly with the incidence and severity of early postoperative neurotoxicity, suggesting that neurotoxicity following liver transplantations may be caused by various factors and is not exclusively a drug-specific side effect of immunosuppression (Mueller, 1994). Even though our data demonstrated that lacking CNAα itself is sufficient to cause the neurotoxicity, suggesting this side effect is drug-specific, we cannot rule out the possibility that malfunction of other organs due to the lack of CNAα is also contributing to the symptom. Further studies are needed to address this question.

CNAα deficient mice have increased mortality rate, which was reported in CsA and FK506 treated child and adult patients (Menegaux, 1994), and mice (Boespflug, 1989). In rats, CsA lowers seizure threshold and probably increase susceptibility to seizure, and 20 mg/kg/day i.p. of CsA caused significant EEG abnormalities and mortality (Racusen, 1990). Why these mice die is unclear to us. CNAα deficient mice can serve as an animal model for study CsA and FK506 immunosuppressive action and side effects.

CNAα is Involved in Hippocampus-dependent Spatial Learning and Play a Critical Role in Long-term Memory Formation Calcineurin Aα deficient mice have a motor deficit, which is affecting the mutants to different degrees. However, this motor deficit is not responsible for the defective spatial learning in the Morris water maze task, because these mutants can find the visible platform as fast as the wild types, suggesting the mutant mice have the motor skill required to swim at a similar speed as the wild type mice. This motor deficit is not responsible for the mild deficit in contextual learning and the defective fear response when testing for their long-term memory in the fear conditioning studies, because the mutant mice are capable of holding the freezing posture and showing a freezing response over an extended period of time.

These mice are not blind either, because they can see the visible platform. But we cannot rule out the possibility that these mice are somehow near-sighted so that they cannot see the more distal spatial cues as clearly, even though near-sightedness of mice has not been reported in the literature. Also, the shocking chamber for the fear conditioning studies is a very small chamber. The mutant mice should be able to see the context inside the chamber, and yet they have a mild deficit in contextual dependent learning, suggesting eyesight is a not a determining factor in our studies.

CNAα deficient mice seem to have normal associative learning ability, since they could perform the visible platform Morris water maze task and had fear responses to foot shocks. However, their hippocampus-dependent learning seem to be affected. The mutant mice have a dramatic deficit in spatial learning in the hidden-platform Morris water maze task, but only a mild deficit in contextual fear conditioning. Both tasks have been shown to be hippocampus dependent (Morris, 1982; Sutherland, 1983; Kim, 1993; Phillips and LeDoux, 1992).

It was suggested that in order to condition to the context, an animal had to construct a unitary configural representation of the context (Nadel, 1985; Fanselow, 1990; Rudy, 1993). So it is possible that the construction of such a configural representation by the hippocampus requires calcineurin a function. In the contextual fear conditioning, due to the mild deficit in spatial information processing, the mutant mice showed a mild deficit in learning. In the hidden-platform Morris water maze task, the spatial cues are much further away and more complexed than the shocking chamber, so that the construction of the "spatial map" is more difficult. The greater difficulty of this task makes it harder to learn and thus the learning deficit in the mutant mice was more severe. Another possibility is that in the Morris water maze task, long term memory may be critical for learning in a distributed trial procedure. So the lack of long term memory formation (as discussed below)in the mutant mice would contribute to the lack of learning during eight days of training. Mass training procedure should be able to compensate for the lack of long-term memory. This argument is supported by the finding that the CREB deficient mice, which have defective long-term memory, learned poorly with a distributed training procedure but their performance was similar to that of the wild type controls during a mass training procedure (Bourtchuladze, 1994). These two possibilities do not conflict with each other, with both may contributing to the severe learning deficit of the mutant mice in the hidden-platform task. This is consistent with the previous findings that memory impairment is exacerbated-by increasing the retention delay or the amount of material to be learned (Mishkin, 1978; ZolaMorgan and Squire, 1985; Squire and Zola-Morgan, 1991).

It was previously shown that there are two temporally distinct forms of associative fear memory, short-term and long-term, that activate the freezing response that emerges shortly after foot shock (Zerbolio, 1969; Kim, 1992; Rudy and Morledge, 1994; Bourtchuladze, 1994). The freezing response measured immediately after the foot shocks are the result of associative learning and short-term memory (Blanchard, 1976; Fanselow, 1986; Kim, 1992; Kim, 1993; Phillips and LeDoux, 1992; Rudy and Morledge, 1994; Bourtchuladze, 1994). The CNAα mutant mice displayed a normal fear response in cued fear conditioning, and an overall normal response in the contextual fear conditioning, even though in the 6th minute the mutants' freezing was marginally significant less. Also, when tested one hour after the contextual training, there was no significant difference between the wild type and mutant mice. All this suggest that their short-term memory is normal.

The formation of long-term and stabilized fear memory requires a time-dependent consolidation process (Rozin, 1976; Squire, 1984; Zerbolio, 1969; Rudy and Morledge, 1994; Kim, 1992). The time window for the consolidation process was shown to be between 10 minutes to 24 hours after the training in rat (Rudy and Morledge, 1994) and between 15 minutes to 2 hours in mice (Zerbolio, 1969). In our studies, the wild type controls underwent memory consolidation between one and two hours after training, while the mutant mice did not, thus causing the gradually loss of fear memory in the mutants. So, as Rudy and Morledge concluded from their study of infantile amnesia (Rudy and Morledge, 1994), our study show that CNAα deficient mice have a defective long-term memory due to a deficiency in memory consolidation. The retention period for the tone-dependent or the context-dependent short-term memory seems to be different, with that of the tone-dependent much shorter. This is in agreement with the previous findings that the time course of amnesia differs for different tasks involving different neuroanatomical structures (Kim and Fanselow, 1992; Kim, 1993; Phillips and LeDoux, 1992; Bourtchuladze, 1994).

Why the lack of CNAα can cause deficit in long-term memory formations is not clear. We would like to postulate that CNAα is a key signaling molecule in such processes. However, even though the medial temporal lobe is important for memory formation (Squire and ZolaMorgan, 1991), evidence also suggests that cerebellum is involved in higher cognitive functions (Middleton and Strick, 1994). Thus, the smaller cerebellum in the mutant mice might affect its function. More studies are needed to further assess CNAα's role in neuronal activities.

Conclusions

We conclude from our study of the CNAα deficient mice that CNAα is mediating CsA and FK506's neurotoxicity and that CNAα is playing a role in the processing of spatial information and the formation long-term memory. Huang, Li, and Kandel had postulated that both NMDA-dependent and NMDA-independent pathways shared a common late phase LTP, which is mRNA and protein synthesis dependent, in which cAMP-dependent kinase is involved, and which leads to memory consolidation (Huang, 1994). It is likely that calcineurin is a key signaling molecule in such a process, the activation of which would lead to the transcription and translation of proteins that are required for the common memory consolidation process.

EXAMPLE 3

Tau and Neurofilament in Calcineurin Aα Deficient Mice

We studied the role of calcineurin Aα in the regulation of phosphorylation status of cytoskeleton proteins in the brain. In mice lacking the a isoform of calcineurin A subunit (CNAα), there is more hyperphosphorylated form of tau protein, which is the major component of paired helical filaments (PHF) found in Alzheimer's disease. The hyperphosphorylation of tau is most profound in the hippocampal mossy fiber region of the mutant mice. In addition, the mossy fiber axons of the CNAα$^{-/-}$ mice contained less neurofilament protein than the wild type. Electromicroscopic studies of mossy fiber revealed a higher microtubule/neurofilament ratio in the mutant brain than in the wild type brain. Our findings indicate that the CNAα regulates the phosphorylations of cytoskeleton proteins, either directly or indirectly. The altered phosphorylation status of tau might have functional consequences that are relevant to Alzheimer's disease.

Alzheimer's disease is a degenerative disease of the central nervous system that results in deficits in memory and cognition. The pathological hallmarks of the disease include neuritic plaques containing the amyloid Aβ protein together with several pathological chaperones, and neurofibrillary tangles (NFT) of paired helical filaments (PHF). Antibodies raised against purified PHF were found to recognize hyperphosphorylated forms of the microtubule-associated protein tau, which were then shown to be the main constituents of PHF. Normally, tau is believed to be involved in the maintenance and development of axonal morphology (Goedert, 1993).

Calcineurin has been shown to have a close association with the cytoskeleton formation or function. In vitro, calcineurin dephosphorylates microtubule-associated protein 2 (MAP2) and tau which are phosphorylated by PKA and CaM-kinase, and tubulin which is phosphorylated by CaM-kinase (Goto, 1985; Drewes, 1993; Gong, 1994). Calcineurin was identified and isolated from adrenal cell cytoskeleton and was able to dephosphorylate cytoskelatal proteins (Papadopoulos, 1990; Papadopoulos, 1989). It is also enriched with the cytoskeleton in the growth cones of developing cerebellar neurons (Ferreira, 1993). In CsA injected rat brain, the inhibition of calcineurin phosphatase activity correlated with the accumulation of phosphorylated neurofilament and probably tau (Tanaka, 1993).

Because of calcineurin's potential role in regulating the phosphorylation status and function of cytoskelatal proteins, we have examined its function in vivo by analyzing the phosphorylation of these proteins in mice deficient for the α isoform of calcineurin A subunit (CNAα). Mutant mice display a large increase in the degree of tau phosphorylation as detected by anti PHF antibodies. The level of PHF immunoreactivity in the mutant mice was highest in the messy fibers of the hippocampus. In the same area, there was decreased neurofilament immunoreactivity in the mutant hippocampus. These results are the first documentation of a role for calcineurin in tau phosphorylation in vivo and suggest that proper cytoskeleton formation depends on the correct balance in phosphorylation of tau and perhaps other proteins.

We have used phosphorylation-dependent or -independent antibodies to investigate the neuropathological effects of lacking CNAα function. Of particular interest was the PHF-1 monoclonal antibody that was raised against PHF purified from Alzheimer's disease brain (Greenberg, 1992). The antigen most clearly recognized by PHF-1 has been shown to be a phosphorylated form of the microtubule-associated protein tau. The dependence of PHF-1 antibody on the phosphorylation state of tau is demonstrated by the fact that immunostaining with PHF-1 is abolished when the PHF tau is dephosphorylated with calcineurin (Gong, 1994). Another antibody used in our study is τ-1 (Binder, 1985) which recognizes dephosphorylated tau but not phosphorylated tau, allowing the specific detection of non-PHF tau. Two other antibodies that are believed to be phosphorylation independent, tau-2 and 5E2, were also tested (Kosik, 1988).

Brain homogenates were prepared from 2–4 months old age matched wild-type and mutant mice, and the phosphorylation state of the proteins were probed with different antibodies. Western analysis showed a consistent increase (up to 7 fold)in PHF-1 immunoreactivity in mutant mice. The mutant mice had either the same or occasionally slightly lower amount of dephosphorylated tau, as shown by τ-1 antibody staining. When the blots were immunostained with the phosphorylation-independent antibodies tau-2 and 5E2 there was a slightly stronger reaction with the mutant mice than the wild type (data not shown). This indicated that the increased staining with PHF-1 in the mutant mice reflected a specific increase in the PHF form (hyperphosphorylated) of tau rather than a general increase in all forms of tau. Thus, the absence of CNAα function caused a shift in tau phosphorylation state, and perhaps also a slight increase in total tau expression.

We next tried to determine the brain regions that were affected by hyperphosphorylation of tau, and whether there were neurofibrillary tangles in the mutant brain. Immunohistochemistry was performed on hippocampal sections with anti-PHF antibodies. Increased immunoreactivity was consistently observed in the hippocampi of mutant mice when compared to that of wild type mice. The most intense immunoreactivity was in the stratum lucidum of the CA3 region, and some staining was also observed in the hilus of the dentate gyrus. In some of the mutant mice, staining was observed in both infrapyramidal and suprapyramidal layers. The PHF staining in the mutants did not correspond to cell bodies of granule or pyramidal cells. The location and orientation of the staining is most consistent with the mossy fiber axons projecting from dentate gyrus into CA3 region. We could not identify plaques or tangles using Congo Red or Bielchowsky's silver staining. The absence of silver staining plaques and tangles is not unexpected since in Alzheimer's disease, positive immunostaining with anti-PHF antibodies long precedes any positive silver staining tangles (Braak, 1994).

Neurofilaments are phosphorylated to different degrees depending on their location and maturation. They have been suggested to convey on axon thickness and stability, and to modulate the axonal caliber (de Waegh, 1992; Hoffman and Cleveland, 1988). Immunostaining with an antibody (SMI32) that recognizes non-phosphorylated neurofilaments revealed no significant difference between wild type and mutant mice (data not shown). Immunostaining with antibodies directed against phosphorylated neurofilament, including SMI34 and SMI310, which stain intracellular and extracellular neurofibrillary tangles respectively, showed a slightly stronger reaction in the wild type than that in the mutant mice. These data suggested that there was no difference in the phosphorylation status of neurofilaments between the wild type and mutant brains.

Interestingly, we observed that processes which showed strong Bielchowsky silver staining in the CA3 region in wild type mice, did not stain in mutant mice. Bielchowsky's silver stain normally labels axons, and a loss of such argyrophilic staining has been observed in degenerating axons in ischemia. The silver staining pattern of the wild type mossy fibers was reminiscent of the anti-PHF staining pattern of the mutant mossy fibers, suggesting that the mossy fibers that stained positively with PHF-1 in mutant mice are not staining with silver. This result could reflect either a reduction in the number of mossy fiber axons or an-alteration in their cytoskeleton, since this silver stain is believed to recognize cytoskelatal elements, particularly neurofilaments.

The possibility that the neurofilaments are altered in mossy fibers in the mutant mice was tested directly by staining sections with an antibody against the 68 kD subunit of neurofilament in a phosphorylation independent manner. We observed a much stronger NF staining in the mossy fibers of wild type mice than that of mutant mice.

We also examined the consequences of these alterations on the ultrastructure of these axons at the electron microscope (EM) level. Half brains from perfused animals were postfixed and processed for EM. The mossy fibers were traced from the pyramidal neurons of CA3. EM studies showed that the neurofilament/microtubule ratio was decreased in the mutant mossy fiber region. The wild type mossy fibers had many regions with abundant neurofilaments, while in the mutant mossy fibers, the neurofilament-rich regions were less frequent. This finding confirmed our observations with immunostaining the Bielchowsky silver staining.

Discussion

Tau is a microtubule-associated protein that is localized primarily in the axons; it has been proposed to form crossbridges between microtubules and between microtubules and neurofilaments (Hirokawa, 1988). Moreover, tau has been shown to stabilize microtubules and promote their assembly, a property that is probably regulated by the phosphorylation state of tau. When tau is phosphorylated, its ability to promote microtubule assembly is diminished (Brandt, 1994) (Drechsel, 1992; Lindwall and Cole, 1984). Recently, it was shown that abnormally phosphorylated tau from Alzheimer's brain inhibited microtubule assembly, and that its ability to promote microtubule assembly was restored upon dephosphorylation (Alonso, 1994). It is conceivable that a shift in tau phosphorylation might perturb cytoskeleton function.

Tau gained special attention when it was shown that the neurofibrillary tangles that accumulate in Alzheimer's disease are composed predominantly of hyperphosphorylated tau. Using antibodies against hyperphosphorylated tau, changes were detected much earlier than the development of argyrophilic staining and before the appearance of any neurofibrillary tangles or amyloid plaques (Braak, 1994; Braak, 1994). In CNAα deficient mice, we were unable to detect any neurofibrillary tangles. It is possible that we are looking at an early stage of the disease onset and that the tangles might form as the mice become older. Alternatively, inasmuch as neurofibrillary tangles have not been observed in mice, the properties of mouse tau protein could preclude PHF formation. Finally, it is possible that other components are needed for the formation of the tangles, just as pathological chaperones appear to be required for the Alzheimer β-protein to polymerize into amyloid filaments (Ma, 1994), while in CNAα mutant mice such components are not affected.

The hippocampal mossy fibers which are projected from granule cells into CA3 are believed to be involved in memory and learning. Granule cells exhibit post-natal neurogenesis and have been proposed to be very plastic in terms of their ability to form new synapses. Such plasticity is normally observed in developing neurons, but persists in adult hippocampus, presumably because of the need for constant synaptic remodeling during memory formation and processing. Mossy fibers have a smaller diameter than many axons, and small axons have been reported to contain greater amount of tau relative to other microtubule associated proteins than the large diameter axons (Harada, 1994). This might result in the prominent PHF staining in the mossy fiber region.

The lack of staining in the mutant mossy fiber area by anti-neurofilament antibodies and by Bielchowsky silver suggests that neurofilaments in mutant mossy fiber axons are down-regulated. This finding was confirmed by the EM examination of the mossy fibers. Tau has been shown to bind to both neurofilaments and microtubules (Miyata, 1986). Since hyperphosphorylation affects tau's ability to bind and stabilize microtubules, it is likely that hyperphosphorylation could also reduce tau binding to NF. The interactions between tau and neurofilaments and microtubules are likely to be important for axonal transport of neurofilaments. Overphosphorylation of tau might perturb these interactions and result in fewer neurofilaments to be transported to the mossy fibers. However, it is possible that overphosphorylation of tau and lack of neurofilament staining in the mutant mossy fibers are two independent phenomena due to lack of CNAα function.

The regional specificity of the PHF-1 immunostaining observed is reminiscent of that affected in some seizures and their animal experimental models. In children with severe epilepsy, there is an increase in Timm's silver deposits (indicating sprouting) in CA3 (Represa, 1989). After kindling or kainic acid treatment of rats (models of epilepsy), mossy fibers exhibited increased Timm's zinc staining in CA3 region, while the CA1 region was not affected (Frotscher, 1983; Sutula, 1988; Represa, 1989). Kainic acid treatment also induced a transient increase in PHF tau immunoreactivity (detect by the Alz50 antibody) in the CA3 neurons (Elliot, 1993). Perhaps CNAα is regulating some key component of the CA3 neural circuit which might be common to the neurological disorders, such as Alzheimer's disease and epilepsy.

In conclusion, we have shown that in CNAα deficient mice, there was an increased level of PHF immunoreactivity in specific regions of the hippocampus. This provided the first link between calcineurin activity to the accumulation of PHF tau in vivo. It is likely that the observed changes in tau phosphorylation and the axonal cytoskeleton underlie a perturbation in neuronal function in mutant mice. Elucidating the specific functional changes especially in the hippocampus might prove to be beneficial in understanding the normal physiology as well as the pathology in neurodegenerative diseases.

REFERENCES

Abeliovich, A., Chen, C., Goda, Y., Silva, A. J., Stevens, C. F., and Tonegawa, S. (1993). Modified hippocampal long-term potentiation in PKC gamma-mutant mice. Cell 75, 1253–62.

Abeliovich, A., Paylor, R., Chen, C., Kim, J. J., Wehner, J. M., and Tonegawa, S. (1993). PKC gamma mutant mice exhibit mild deficits in spatial and contextual learning. Cell 75, 1263–71.

Aitken, A., Cohen, P., Santikarn, S., Williams, D. H., Calder, A. G., Smith, A., and Klee, C. B. (1982). Identification of the NH2-terminal blocking group of calcineurin B as myristic acid. FEBS Letters 150, 314–8.

Aitken, A., Klee, C. B., and Cohen, P. (1984). The structure of the B subunit of calcineurin. European Journal of Biochemistry 139, 663–71.

Albers, M. W., Williams, R. T., Brown, E. J., Tanaka, A., Hall, F. L., and Schreiber, S. L. (1993). FKBP-rapamycin inhibits a cyclin-dependent kinase activity and a cyclin D1-Cdk association in early G1 of an osteosarcoma cell line. Journal of Biological Chemistry 268, 22825–9.

Alonso, A. D. C., Zaidi, T., Grundke-lqbal, I., and lqbal, K. (1994). Role of abnormally phosphorylated tau in the breakdown of microtubule in Alzheimer's disease. Proc. Natl. Acad. Sci. USA 91, 5562–5566.

Anderson, S. K., Gallinger, S., Roder, J., Frey, J., Young, H. A., and Ortaldo, J. R. (1993). A cyclophilin-related protein involved in the function of natural killer cells. Proc. Natl. Acad. Sci. (USA) 90.

Anonymous (1994). A comparison of tacrolimus (FK 506) and cyclosporine for immunosuppression in liver transplantation. The U.S. Multicenter FK506 Liver Study Group [see comments]. New England Journal of Medicine 331, 1110–5.

Appleton, R. E., Farrell, K., Teal, P., Hashimoto, S. A., and Wong, P. K. (1989). Complex partial status epilepticus associated with cyclosporin A therapy. Journal of Neurology, Neurosurgery & Psychiatry 52, 1068–71.

Arber, S., Krause, K. H., and Caroni, P. (1992). s-cyclophilin is retained intracellularly via a unique COOH-terminal sequence and colocalize with the calcium storage protein calreticulin. Journal of Cell Biology 116, 113–25.

Armstrong, D. L. (1989). Calcium channel regulation by calcineurin, a Ca2+activated phosphatase in mammalian brain. Trends in Neurosciences 12, 11722.

Atkinson, K., Biggs, J., Darveniza, P., Boland, J., Concannon, A., and Dodds, A. (1984). Cyclosporin-associated central nervous system toxicity after allogeneic bone marrow transplantation. Transplantation 38, 34–7.

Ausubel, F. M., Brent, R., Kingston, R. E., Moore, D. D., eidman, J. G., Smith, J. A., and Struhl, K. (1994). Current Protocols in Molecular Biology (Brooklyn: Greene Publishing).

Banerji, S. S., Parsons, J. N., and Tocci, M. J. (1991). The immunosuppressant FK-506 specifically inhibits mitogen-induced activation of the interleukin-2 promoter and the isolated enhancer elements NFIL-2A and NF-AT1. Molecular & Cellular Biology 11, 4074–87.

Bergsma, D. J., Eder, C., Gross, M., Kersten, H., Sylvester, D., Appelbaum, E., Cusimano, D., Livi, G. P., McLaughlin, M. M., Kasyan, K., and (1991). The cyclophilin multigene family of peptidyl-prolyl isomerases. Characterization of three separate human isoforms. Journal of Biological Chemistry 266, 23204–14.

Bialojan, C., and Takai, A. (1988). Inhibitory effect of a marine-sponge toxin, okadaic acid, on protein phosphatases. Specificity and kinetics. Biochemical Journal 256, 283–90.

Bierer, B. E., Hollander, G., Fruman, D., and Burakoff, S. J. (1993). Cyclosporin A and FK506: molecular mechanisms of immunosuppression and probes for transplantation biology. Current Opinion in Immunology 5, 763–73.

Bierer, B. E., Mattila, P. S., Standaert, R. F., Herzenberg, L. A., Burakoff, S. J., Crabtree, G., and Schreiber, S. L. (1990). Two distinct signal transmission pathways in T lymphocytes are inhibited by complexes formed between an immunophilin and either FK506 or rapamycin. Proceedings of the National Academy of Sciences of the United States of America 87, 9231–5.

Bierer, B. E., Schreiber, S. L., and Burakoff, S. J. (1991). The effect of the immunosuppressant FK-506 on alternate pathways of T cell activation. European Journal of Immunology 21, 439–45.

Bierer, B. E., Somers, P. K., Wandless, T. J., Burakoff, S. J., and Schreiber, S. L. (1990). Probing immunosuppressant action with a nonnatural immunophilin ligand. Science 250, 556–9.

Binder, L. I., Frankfurter, A., and Rebhun, L. I. (1985). The distribution of tau in the mammalian central nervous system. Journal of Biological Chemistry 101, 1371–1378.

Blanchard, R. J., and Blanchard, D. C. (1969). Crouching as an index of fear. Journal of Comparative and Physiological Psychology 67, 370–375.

Blanchard, R. J., Fukunaga, K. K., and Blanchard, D. C. (1976). Environmental control of defensive reactions to footshock. Bulletin of the Psychonomic Society 8.

Bliss, T. V. P., and Coilingridge, G. L. (1993). A synaptic model of memory: long-term potentiation in the hippocampus. Nature 361.

Bloemena, E., Van Oers, M. H., Weinreich, S., and Schellekens, P. T. (1988). Cyclosporin A and prednisolone do not inhibit the expression of high-affinity receptors for interleukin 2. Clinical & Experimental Immunology 71, 308–13.

Bloemena, E., Van Oers, R. H., Weinreich, S., Stilma-Meinesz, A. P., Schellekens, P. T., and Van Lier, R. A. (1989). The influence of cyclosporin A on the alternative pathways of human T cell activation in vitro. European Journal of Immunology 19, 943–6.

Boespflug, O., Godfraind, C., and Tardieu, M. (1989). Effect of cyclosporin A on an experimental chronic viral infection of the central nervous system. Journal of Neuroimmunology 21, 49–57.

Boland, J., Atkinson, K., Britton, K., Darveniza, P., Johnson, S., and Biggs, J. (1984). Tissue distribution and toxicity of cyclosporin A in the mouse. Pathology 16, 117–23.

Bolles, R. C., and Fanselow, M. S. (1980). A perceptual-defense-recuperative model of fear and pain. Behavioral and Brain Sciences 3.

Borel, J. F., Feurer, C., Gubler, H. U., and Stahelin, H. (1976). Biological effects of cyclosporin A: a new anti-lymphocytic agent. Agents & Actions 6, 468–75.

Borel, J. F., Feurer, C., Magnee, C., and Stahelin, H. (1977). Effects of the new anti-lymphocytic peptide cyclosporin A in animals. Immunology 32, 1017–25.

Bourtchuladze, R., Frenguelli, B., Blendy, J., Cioffi, D., Schutz, G., and Silva, A. J. (1994). Deficient long-term memory in mice with a targeted mutation of the cAMP-responsive element-binding protein. Cell 79, 59–68.

Braak, E., Braak, H., and Mandelkow, E.-M. (1994). A sequence of cytoskeleton changes related to the formation of neurofibrillary tangles and neuropil threads. Acta Neuropathologica 87, 554–567.

Braak, H., Braak, E., and Strothjohann, M. (1994). Abnormally phosphorylated tau protein related to the formation of neurofibrillary tangles and neuropil threads in the cerebral cortex of sheep and goat. Neuroscience Letters 171, 1–4.

Brabletz, T., Pietrowski, I., and Serfling, E. (1991). The immunosuppressives FK 506 and cyclosporin A inhibit the generation of protein factors binding to the two purine boxes of the interleukin 2 enhancer. Nucleic Acids Research 19, 61–7.

Bradley, A. (1987). Production and analysis of chimeric mice. In Terotocarcinomas and Embryonic Stem Cells: A Practical Approach, E. J. Robertson, ed. (Oxford: IRL press), pp. 113–151.

Bram, R. J., and Crabtree, G. R. (1994). Calcium signalling in T cells stimulated by a cyclophilin B-binding protein. Nature 371, 355–8.

Bram, R. J., Hung, D. T., Martin, P. K., Schreiber, S. L., and Crabtree, G. R. (1993). Identification of the immunophilins capable of mediating inhibition of signal transduction by cyclosporin A and FK506: roles of calcineurin binding and cellular location. Molecular & Cellular Biology 13, 4760–9.

Brandeis, R., Brandys, Y., and Yehuda, S. (1989). The use of the Morris water maze in the study of memory and learning. Int. J. Neurosci. 48, 29–69., Brandt, R., Lee, G., Teplow, D. B., Shalloway, D., and Abdel-Ghany, M. (1994). Differential effect of phosphorylation and substrate modulation on tau's ability to promote microtubule growth and nucleation. Journal of Biological Chemistry 269, 11776–11782.

Brat, D. J., Windebank, A. J., and Brimijoin, S. (1992). Emulsifier for intravenous cyclosporin inhibits. Journal of Pharmacology & Experimental Therapeutics 261, 803–10.

Brillantes, A. B., Ondrias, K., Scott, A., Kobrinsky, E., Ondriasova, E., Moschella, M. C., Jayaraman, T., Landers, M., Ehrlich, B. E., and Marks, A. R. (1994). Stabilization of calcium release channel (ryanodine receptor) function by FK506-binding protein. Cell 77, 513–23.

Buttini, M., Limonta, S., Luyten, M., and Boddeke, H4. (1993). Differential distribution of calcineurin A alpha isoenzyme mRNA's in rat brain. NaunynSchmiedebergs Archives of Pharmacology 348, 679–83.

Chen, J., Lansford, R., Stewart, V., Young, F., and Alt, F. W. (1993). RAG-2deficient blastocyst complementation: An assay of gene function in lymphocyte development. Proc. Natl. Acad. Sci. USA 90, 4528–4532.

Chung, J., Kuo, C. J., Crabtree, G. R., and Blenis, J. (1992). Rapamycin-FKBP specifically blocks growth-dependent activation of and signaling by the 70 kd $6 protein kinases. Cell 69, 1227–36.

Clipstone, N. A., and Crabtree, G. R. (1992). Identification of calcineurin as a key signalling enzyme in T-lymphocyte activation. Nature 357, 695–7.

Cohen, P. (1989). The structure and regulation of protein phosphatases. Annu. Rev. Biochem. 58, 453–508.

Coligan, J. E., Kruisbeek, A. M., Margulies, D. H., Shevach, E. M., and Strober, W. (1994). Current protocols in Immunology, R. Coico, ed. (Brooklyn: Greene Publishing).

Crabtree, G. R. (1989). Contingent genetic regulatory events in T lymphocyte activation. Science 243, 355–361.

Crabtree, G. R., and Clipstone, N. A. (1994). Signal transmission between the plasma membrane and nucleus of T lymphocyte. Annu. Rev. Biochem. 63, 1045–1083.

da Cruz e Silva, E. F., and Cohen, P. T. (1989). Isolation of a cDNA likely to encode a novel Ca2+-dependent/calmodulin-stimulated protein phosphatase. Biochimica et Biophysica Acta 1009, 293–296.

Davis, E. S., Becker, A., Heitman, J., Hall, M. N., and Brennan, M. B. (1992). A yeast cyclophilin gene essential for lactate metabolism at high temperature. Proceedings of the National Academy of Sciences of the United States of America 89, 11169–73.

Davis, H. P., and Squire, L. R. (1984). Protein synthesis and memory. Psychol. Bull. 96, 518–559.

Dawson, T. M., Steiner, J. P., Dawson, V. L., Dinerman, J. L., Uhl, G. R., and Snyder, S. H. (1993). Immunosuppressant FK5(]6 enhances phosphorylation of nitric oxide synthase and protects against glutamate neurotoxicity [see comments]. Proceedings of the National Academy of Sciences of the United States of America 90, 9808–12.

Dawson, T. M., Steiner, J. P., Lyons, W. E., Fotuhi, M., Blue, M., and Snyder, S. H. (1994). The immunophilins, FK506 binding protein and cyclophilin, are discretely localized in the brain: relationship to calcineurin. Neuroscience 62, 569–580.

de Paulis, A., Cirillo, R., Ciccarelli, A., Condorelli, M., and MaRone, G. (1991). FK-506, a potent novel inhibitor of the release of proinflammatory mediators from human FcεRI+ cells. J. Immunology 146, 2374–2381.

de Waegh, S. M., Lee, V. M.-Y., and Brady, S. (1992). Local modulation of neurofilament phosphorylation, axonal caliber, and slow axonal transport by myelinating Schwann cells. 68, 451–463.

Dickinson, A., and Mackintosh, N. J. (1978). Classical conditioning in animals. Annu. Rev. Psychol. 29, 587–612.

Drechsel, D. N., Hyman, A. A., Cobb, M. H., and Kirschner, M. W. (1992). Modulation of the dynamic instability of tubulin assembly by the microtubuleassociated protein tau. Molecular Biology of the Cell 3, 1141–1154.

Drewes, G., Mandelkow, E.-M., Baumann, K., Goris, J., Merlevede, W., and Mandelkow, E. (1993). Dephosphorylation of tau protein and Alzheimer paired helical filaments by calcineurin and phosphatase-2A. FEBS Letters 336, 425432.

Drewes, G., Mandelkow, E.-M., Baumann, K., Goris, J., Merlevede, W., and Mandelkow, E. (1993). Dephosphorylation of tau protein and Alzheimer paired helical filaments by calcineurin and phosphatase-2A. FEBS Letters 336, 425432.

Drewes, G., Mandelkow, E. M., Baumann, K., Goris, J., Merlevede, W., and Mandelkow, E. (1993). Dephosphorylation of tau protein and Alzheimer paired helical filaments by calcineurin and phosphatase-2A. FEBS Letters 336, 42532.

Dumont, F. J., Melino, M. R., Staruch, M. J., Koprak, S. L., Fischer, P. A., and Sigal, N. H. (1990). The immunosuppressive macrolides FK-506 and rapamycin act as reciprocal antagonists in murine T cells. Journal of Immunology 144, 1418–24.

Dumont, F. J., Melino, M. R., Staruch, M. J., Koprak, S. L., Fischer, P. A., and Sigal, IN. H (1990). The immunosuppressive macrolides FK-506 and rapamycin act as reciprocal antagonists in murine T cells. Journal of Immunology 144, 1418–24.

Dumont, F. J., Staruch, M. J., Koprak, S. L., Melino, M. 'R., and Sigal, N. H. (1990). Distinct mechanisms ef suppression of murine T cell activation by the related macrolides FK-506 and rapamycin. Journal of Immunology 144, 251–8.

Dumont, F. J., Staruch, M. J., Koprak, S. L., Melino, M. R., and Sigal, N. H. (1990). Distinct mechanisms of suppression of murine T cell activation by the related macrolides FK-506 and rapamycin. Journal of Immunology 144, 251–8.

Dumont, F. J., Staruch, M. J., Koprak, S. L., Siekerka, J. J., Lin, C. S., Harrison, R., Sewell, T., Kindt, V. M., Beattie, T. R., Wyvratt, M., and Sigal, N. H. (1992). The immunosuppressive and toxic effects of FK-506 are mechanistically related: pharmacology of a novel antagonist of FK-506 and rapamycin. J. Exp. Med. 176,751–760.

Eichenbaum, H., Cohen, N. J., Otto, T., and Wible, C. (1991). Memory representation in the hippocampus: functional domain and functional organization. In Memory: Organization and Locus of Change, L. R. Squire, N. M. Weinberger, G. Lynch and J. L. McGaugh, eds. (New York: Oxford University Press), pp. 163–204.

Eichenbaum, H., Otto, T., and Cohen, N. J. (1992). The Hippocampus: What does it do? Behav. Neural Bio. 57, 2–36.

Elliot, E. M., M. P. Mattson, P. Vanderklish, G. Lynch, I. Chang, and R. M. Sapolsky (1993). Corticosterone excacerbates kainate-induced alterations in hippocampal tau immunoreactivity and spectrin proteolysis in vivo. Journal of Neurochemistry 61, 57–67.

Emmel, E. A., Verweij, C. L., Durand, D. B., Higgins, K. M., Lacy, E., and Crabtree, G. R. (1989). Cyclosporin A specifically inhibits function of nuclear proteins involved in T cell activation. Science 246, 1617–20.

Fanselow, M. S. (1986). Associative versus topographical accounts of the immediate shock-freezing deficit in rats: implications for the response selection rules governing species-specific defensive reactions. Learning and Motivation 17, 16–39.

Fanselow, M. S. (1986). Conditioned fear-induced opiate analgesia: a competing motivational state theory of stress analgesia. Annals of the New York Academy of Sciences 467, 40–54.

Fanselow, M. S. (1990). Factors governing one trial context conditioning. Animal learning and Behavior 18, 264–270.

Fanselow, M. S., and Bolles, R. C. (1979). Naloxone and shock-elicited freezing in the rat. Journal of Comparative & Physiological Psychology 93, 736–744.

Fanselow, M. S., and Bolles, R. C. (1979). Triggering the endorphin analgesic reaction by a cue previously associates with shock: reversal by naloxone. Bull. Psychbn. Soc. 14, 88–90.

Ferreira, A., Kincaid, R., and Kosik, K. S. (1993). Calcineurin is associated with the cytoskeleton of cultured neurons and has a role in the acquisition of polarity. Molecular Biology of the Cell 4, 1225–38.

Fischer, G., Bang, H., and Mech, C. (1984). Determination of enzymatic catalysis for the cis-trans-isomerization of peptide binding in proline-containing peptides. Biomed. Biochem. Acta. 43, 1101–1111.

Fischer, G., Wittmann-Liebold, B., Lang, K., Kiefhaber, T., and Schmid, F. X. (1989). Cyclophilin and peptidyl-prolyl cis-trans isomerase are probably identical proteins [see comments]. Nature 337, 476–8.

Flanagan, W. M., Corthesy, B., Bram, R. J., and Crabtree, G. R. (1991). Nuclear association of a T-cell transcription factor blocked by FK-506 and cyclesporin A [see comments]. Nature 352, 803–7.

Foor, F., Parent, S. A., Morin, N., Dahl, A. M., Ramadan, N., Chrebet, G., Bostian, K. A., and Nielsen, J. B. (1992). Calcineurin mediates inhibition by FK506 and cyclosporin of recovery from alpha-factor arrest in yeast. Nature 360, 682–4.

Forrest, M. J., Jewell, M. E., Koo, G. C., and Sigal, N. H. (1991). FK-506 and cyclosporin A: selective inhibition of calcium ionophore-induced polymorphonuclear leukocyte degranulation. Biochemical Pharmacology 42, 1221–8.

Franke, E. K., Yuan, H. E. H., and Luban, J. (1994). Specific incorporation of cyclosporin A into HIV-1 virions. Nature 372, 359–362.

Frantz, B., Nordby, E. C., Bren, G., Steffan, N., Paya, C. V., Kincaid, R. L., Tocci, M. J., O'Keefe, S. J., and O'Neill, E. A. (1994). Calcineurin acts in synergy with PMA to inactivate I kappa B/MAD3, an inhibitor of NF-kappa B. EMBO Journal 13, 861–70.

Freskgard, P. O., Bergenham, N., Jonsson, B. H., Svensson, M., and Carlsson, U. (1992). Isomerase and chaperone activity of prolyl isomerase in the folding of carbonic anhydras. Science 258.

Frey, U., Huang, Y.-Y., and Kandel, E. R. (1993). Effects of cAMP simulate a late stage of LTP in hippocampal CA1 neurons. Science 260, 1661–1664.

Friedman, J., and Weissman, I. (1991). Two cytoplasmic candidates for immunophilin action are revealed by affinity for a new cyclophilin: one in the presence and one in the absence of CsA. Cell 66, 799–806.

Frotscher, M., and J. Zimmer (1983). Lesion-induced mossy fibers to the molecular layer of the rat fascia dentata: identification of postsynaptic granule cells by the golgi E-M technique. Journal of Comparative Neurology, 299–311.

Fruman, D. A., Klee, C. B., Bierer, B. E., and Burakoff, S. J. (1992). CalCineurin phosphatase activity in T lymphocytes is inhibited by FK 506 and cyciosporin A. Proceedings of the National Academy of Sciences of the United States of America 89, 3686–90.

Galat, A., Lane, W. S., Standaert, R. F., and Schreiber, S. L. (1992). A rapamycin-selective 25-kDa immunophilin. Biochemistry 31, 2427–34.

Gao, E. K., Lo, D., Cheney, R., Kanagawa, O., and Sprent, J. (1988). Abnormal differentiation of thymocytes in mice treated with cyclosporin A. Nature 336, 176–179.

Goedert, M. (1993). Tau protein and the neurofibrillary pathology of Alzheimer's disease. Trends in the Neurosciences 16, 460–465.

Goldman, J., and Cote, L. (1991). Aging of the Brain: Dementia of the Alzheimer's Type. In Principles of neural science, E. K. Kandel, J. H. Schwartz and T. M. Jessell, eds. (East Norwalk, Conn.: Appleton & Lange), pp. 976–981.

Gong, C. X., Singh, T. J., Grundke-Iqbal, I., and Iqbal, K. (1994). Alzheimer's disease abnormally phosphorylated $\tau$ is dephosphorylated by protein phosphatase-2B (caslcineurin). Journal of Neurochemistry 62, 803–806.

Goto, S., Nagahiro, S., Korematsu, K., Ushio, Y., Fukunaga, K., Miyamoto, E., and Hofer, W. (1993). Cellular colocalization of calcium/calmodulin-dependent protein kinase II and calcineurin in the rat cerebral cortex and hippocampus. Neuroscience Letters 149, 189–92.

Goto, S., Yamamoto, H., Fukunaga, K., lwasa, T., Matsukado, Y., and Miyamoto, E. (1985). Dephosphorylation of microtubule-associated protein 2, tau factor, and tubulin by calcineurin. Journal of Neurochemistry 45, 276–83.

Greenberg, S. G., Davies, P., Schein, J. D., and Binder, L. I. (1992). Hydrofluoric acid-treated X PHF proteins display the same biochemical properties as normal T. Journal of Biological Chemistry 267, 564–569.

Guerini, D., and Klee, C. B. (1989). Cloning of human calcineurin A: evidence for two isozymes and identification of a polyproline structural domain. Proceedings of the National Academy of Sciences of the United States of America 86, 9183–7.

Guerini, D., and Klee, C. B. (1991). Structural diversity of calcineurin, a $Ca^{2+}$ and calmodulin-stimulated protein phosphatase. Adv. pro. Phosphatases 6, 391–410.

Guerini, D., Krinks, M. H., Sikela, J. M., Hahn, W. E., and Klee, C. B. (1989). Isolation and sequence of a cDNA clone for human calcineurin B, the Ca2+-binding subunit of the Ca2+/calmodulin-stimulated protein phosphatase. Dna 8, 675–82.

Gupta, R. C., Khandelwal, R. L., and Sulakhe, P. V. (1986). Interaction amongst calcineurin subunits. Stimulatory and inhibitory effects of subunit B on calmodulin stimulation of subunit A phosphatase activity depend on Mn2+ exposure of the holoenzyme prior to its dissociation by urea. FEBS Letters 196, 39–43.

Haddy, A., Swanson, S. K., Born, T. L., and Rusnak, F. (1992). Inhibition of calcineurin by cyclosporin A-cyclophilin requires calcineurin B. FEBS Letters 314, 37–40.

Haendler, B., Keller, R., Hiestand, P. C., Kocher, H. P., Wegmann, G., and Movva, N. R. (1989). Yeast cyclophilin: isolation and characterization of the protein, cDNA and gene. Gene 83, 39–46.

Halpain, S., Girault, J. A., and Greengard, P. (1990). Activation of NMDA receptors induces dephosphorylation of DARPP-32 in rat striatal slices. Nature 343, 369–72.

Halpain, S., and Greengard, P. (1990). Activation of NMDA receptors induces rapid dephosphorylation of the cytoskeletal protein MAP2. Neuron 5, 237–46.

Handschumacher, R. E., Harding, M. W., Rice, J., Drugge, R. J., and Speicher, D. W. (1984). Cyclophilin: a specific cytosolic binding protein for cyclosporin A. Science 226, 544–7.

Harada, A., Oguchi, K., Okabe, S., Kuno, J., Terada, S., Ohshima, T., SatoYoshitake, R., Takei, Y., Noda, T., and Hirokawa, N. (1994). Altered microtubule organization in small-calibre axons of mice lacking tau', protein. 369, 488–491.

Harding, M. W., Galat, A., Uehling, D. E., and Schreiber, S. L. (1989). A receptor for the immunosuppressant FK506 is a cis-trans peptidyl-prolyl isomerase. Nature 341, 758–60.

Harding, M. W., Handschumacher, R. E., and Speicher, D. W. (1986). Isolation and amino acid sequence of cyclophilin. Journal of Biological Chemistry 261, 8547–55.

Harris, K. A., Oyler, G. A., Doolittle, G. M., Vincent, I., Lehman, R. A., Kincaid, R. L., and Billingsley, M. L. (1993). Okadaic acid induces hyperphosphorylated forms of tau protein in human brain slices. Annals of Neurology 33, 77–87.

Hasel, K. W., Glass, J. R., Godbout, M., and Sutcliffe, J. G. (1991). An endoplasmic reticulum-specific cyclophilin. Molecular & Cellular Biology 11, 3484–91.

Hashimoto, Y., King, M. M., and Soderling, T. R. (1988). Regulatory interactions of calmodulin-binding proteins: phosphorylation of calcineurin by autophosphorylated $Ca2+$/calmodulin-dependent protein kinase II. Proceedings of the National Academy of Sciences of the United States of America 85, 70015.

Hashimoto, Y., Perrino, B. A., and Soderling, T. R. (1990). Identification of an autoinhibitory domain in calcineurin. Journal of Biological Chemistry 265, 19247.

Hashimoto, Y., and Soderling, T. R. (1989). Regulation of calcineurin by phosphorylation. Identification of the regulatory site phosphorylated by $Ca2+$/calmodulin-dependent protein kinase II and protein kinase C. Journal of Biological Chemistry 264, 16524–9.

Heitman, J., Movva, N. R., Hiestand, P. C., and Hall, M. N. (1991). FK 506-binding protein proline rotamase is a target for the immunosuppressive agent FK 506 in Saccharomyces cerevisiae. Proceedings of the National Academy of Sciences of the United States of America 88, 1948–52.

Herold, K. C., Lancki, D. W., Moldwin, R. L., and Fitch, F. W. (1986). Immunosuppressive effects of cyclosporin A on cloned T cells. Journal of Immunology 136, 1315–21.

Hess, A. D., Tutschka, P. J., Pu, Z., and Santos, G. W. (1982). Effect of cyclosporin A on human lymphocyte responses in vitro. IV. Production of T cell stimulatory growth factors and development of responsiveness to these growth factors in CsA-treated primary MLR cultures. Journal of Immunology 128, 360–7.

Hirokawa, N., Shiomura, Y., and Okabe, S. (1988). Tau proteins: the molecular structure and mode of binding on microtubules. Journal-of Cell Biology 107, 1449–1459.

Hirsh, R. (1974). The hippocampus and contextual retrieval of information from memory: a theory. Behav. Biol. 12, 421–444.

Ho, A. K., Ling, Q. L., Duffield, R., Lam, P. H., and Wang, J. H. (1987). Phosphorylation of brain muscarinic receptor: evidence of receptor regulation. Biochemical & Biophysical Research Communications 142, 911–8.

Hoffman, P. N., and Cleveland, D. W. (1988). Neurofilament and tubulin expression recapitulates the developmental pattern during axonal regeneration: induction of a specific 13-tubulin isotype. Proc. Natl. Acad. Sci. USA 85, 4530–4533.

Hosey, M. M., Borsotto, M., and Lazdunski, M. (1986). Phosphorylation and dephosphO'rylation of dihydropyridine-sensitive voltage-dependent $Ca2+$ channel in skeletal muscle membranes by cAMP- and $Ca2+$-dependent processes. Proceedings of the National Academy of Sciences of the United States of America 83, 3733–7.

Huang, Y.-Y., and Kandel, E. R. (1994). Recruitment of long-lasting and protein kinase A-dependent long-term potentiation in the CA1 region of hippocampus requires repeated tetanization. Learning Memory 1, 74–82.

Huang, Y.-Y., Li, X.-C., and Kandel, E. R. (1994). cAMP contributes to Mossy Fiber LTP by initiating both a covalently mediated early phase and macromolecular synthesis-dependent late phase. Cell 79, 69–79.

Hubbard, M. J., and Klee, C. B. (1989). Functional domain structure of calcineurin A: mapping by limited proteolysis. Biochemistry 28, 1868–74.

Hultsch, T., Albers, M. W., Schreiber, S. L., and Hohman, R. J. (1991). Immunophilin ligands demonstrate common features of signal transduction leading to exocytosis or transcription. Proceedings of the National Academy of Sciences of the United States of America 88, 6229–33.

Hultsch, T., Rodriguez, J. L., Kaliner, M. A., and Hohman, R. J. (1990). Cyclosporin A inhibits degranulation of rat basophilic leukemia cells and human basophils. Inhibition of mediator release without affecting PI hydrolysis or $Ca2+$fluxes. Journal of Immunology 144, 2659–64.

Ito, A., Hashimoto, T., Hirai, M., Takeda, T., Shuntoh, H., Kuno, T., and Tanaka, C. (1989). The complete primary structure of calcineurin A, a calmodulin binding protein homologous with protein phosphatases 1 and 2A. Biochemical & Biophysical Research Communications 163, 1492–7.

Jahr, C. E., and Lester, R. A. (1992). Synaptic excitation mediated by glutamate gated ion channels. Current Opinion in Neurobiology 2, 270–4.

Jain, J., McCaffrey, P. G., Miner, Z., Kerppola, T. K., Lambert, J. N., Verdine, G. L., Curran, T., and Rao, A. (1993). The T-cell transcription factor NFATp is a substrate for calcineurin and interacts with Fos and Jun. Nature 365, 352–5.

Jain, J., McCaffrey, P. G., Miner, Z., Kerppola, T. K., Lambert, J. N., Verdine, G. L., Curran, T., and Rao, A. (1993). The T-cell transcription factor NFATp is a substrate for calcineurin and interacts with Fos and Jun. Nature 365, 352–5.

Jarrard, L. E. (1993). On the role of the hippocampus in learning and memory in rat. Behav. Neural Biol. 60, 9–26.

Jayaraman, T., Brillantes, A. M., Timerman, A. P., Fleischer, S., Erdjument-Bromage, H., Tempst, P., and Marks, A. R. (1992). FK506 binding protein associated with the calcium release channel (ryanodine receptor). Journal of Biological Chemistry 267, 9474–7.

Jayaraman, T., and Marks, A. R. (1993). Rapamycin-FKBP12 blocks proliferation, induces differentiation, and inhibits cdc2 kinase activity in a myogenic cell line. Journal of Biological Chemistry 268, 25385–8.

Jenkins, M. K., Schwarts, R. H., and Pardoil, D. M. (1988). Effects of cyclosporine A on T cell development and clonal deletion. Science 24 1, 16551658.

Jin, Y. J., Albers, M. W., Lane, W. S., Bierer, B. E., Schreiber, S. L., and Burakoff, S. J. (1991). Molecular cloning of a membrane-associated human FK5D6- and rapamycin-binding protein, FKBP-13. Proceedings of the National Academy of Sciences of the United States of America 88, 6677–81.

Jin, Y. J., and Burakoff, S. J. (1993). The 25-kDa FK506-binding protein is localized in the nucleus and associates with casein kinase II and nucleolin. Proceedings of the National Academy of Sciences of the United States of America 90, 7769–73.

Jin, Y. J., Burakoff, S. J., and Bierer, B. E. (1992). Molecular cloning of a 25-kDa high affinity' rapamycin binding protein, FKBP25. Journal of Biological Chemistry 267, 10942–5.

Johansson, A., and Moller, E. (1990). Evidence that the immunosuppressive effects of FK506 and cyclosporine are identical. Transplantation 50, 1001–7. June, C. H., Ledbetter, J. A., Gillespie, M. M., Lindsten, T., and Thompson, C. B. (1987). T-cell proliferation involving the CD28 pathway is associated with cyclosporin-resistant interleukin 2 gene expression. Mol Cell Biol 7, 4472–4481.

Kandel, E. R. (1991). Cellular mechanisms of learning and the biological basis of individuality. In Principles of neural science, E. R. Kandel, J. H. Schwartz and T. M. Jessell, eds. (East Norwalk, Conn.: Appleton & Lange), pp. 1010–1026.

Kaye, R. E., Fruman, D. A., Bierer, B. E., Albers, M. W., Zydowsky, L. D., Ho, S. I., Jin, Y. J., Castells, M. C., Schreiber, S. L., Walsh, C. T., and (1992). Effects of cyclosporin A and FK506 on Fc epsilon receptor type 1-initiated increases in cytokine mRNA in mouse bone marrow-derived progenitor mast cells: resistance to FK506 is associated with a deficiency in FK506-binding protein FKBP12. Proceedings of the National Academy of Sciences of the United States of America 89, 8542–6.

Kern, D., Drakenberg, T., Wikstrom, M., Forsen, S., Bang, H., and Fischer, G. (1993). The cis/trans interconversion of the calcium regulating hormone calcitonin is catalyzed by cyclophilin. FEBS Letters 323, 198–202.

Kieffer, L. J., Seng, T. W., Li, W., Osterman, D. G., Handschumacher, R. E., and Bayney, R. M. (1993). Cyclophilin-40, a protein with homology to the P59 component of the steroid receptor complex. Cloning of the cDNA and further characterization. Journal of Biological Chemistry 268, 12303–10.

Kieffer, L. J., Thaihammer, T., and Handschumacher, R. E. (1992). Isolation and characterization of a 40-kDa cyclophilin-related protein. Journal of Biological Chemistry 267, 5503–7.

Kim, J. J.; and Fanselow, M. S. (1992). Modality-specific retrograde amnesia of fear. Science 256, 675–7.

Kim, J. J., Fanselow, M. S., DeCola, J. P., and Landeira-Fernandez, J. (1992). Selective impairment of long-term but not short-term conditional fear by the N-methyl-D-aspartate antagonist APV. Behavioral Neuroscience 106, 591–6.

Kim, J. J., Rison, R. A., and Fanselow, M. S. (1993). Effects of amygdala, hippocampus, and periaqueductal gray lesions on short- and long-term contextual fear. Behavioral Neuroscience 107, 1093–8.

Kincaid, R. L., Giri, P. R., Higuchi, S., Tamura, J., Dixon, S. C., Marietta, C. A., Amorese, D. A., and Martin, B. M. (1990). Cloning and characterization of molecular isoforms of the catalytic subunit of calcineurin using nonisotopic methods. Journal of Biological Chemistry 265, 11312–9.

Kincaid, R. L., Takayama, H., Billingsley, M. L., and Sitkovsky, M. V. (1987). Differential expression of calmodulin-binding proteins in B, T lymphocytes and thymocytes. Nature 330, 176–8.

Klee, C. B. (1991). Concerted regulation of protein phosphorylation and dephosphorylation by calmodulin. Neurochemical Research 16, 1059–65.

Klee, C. B., Crouch, T. H., and Krinks, M. H. (1979). Calcineurin: a calcium- and calmodulin-binding protein of the nervous system. Proceedings of the National Academy of Sciences of the United States of America 76, 6270–3.

Klee, C. B., Krinks, M. H., Manalan, A. S., Cohen, P., and Stewart, A. A. (1983). Isolation and characterization of bovine brain calcineurin: a calmodulinstimulated protein phosphatase. Methods in Enzymology 102, 227–44.

Koletsky, A. J., Harding, M. W., and Handschumacher, R. E. (1986). Cyclophilin: distribution and variant properties in normal and neoplastic tissues. Journal of Immunology 137, 1054–9.

Koltin, Y., Faucette, L., Bergsma, D. J., Levy, M. A., Cafferkey, R., Koser, P. L., Johnson, R~K., and Livi, G. P. (1991). Rapamycin sensitivity in Saccharomyces cerevisiae is mediated by a peptidyl-prolyl cis-trans isomerase related to human FK506-binding protein. Molecular & Cellular Biology 11, 1718–23.

Koser, P. L., Bergsma, D. J., Cafferkey, R., Eng, W. K., McLaughlin, M. M., Ferrara, A., Silverman, C., Kasyan, K., Bossard, M. J., Johnson, R. K., and (1991). The CYP2 gene of Saccharomyces cerevisiae encodes a cyclosporin A-sensitive peptidyl-prolyl cis-trans isomerase with an N-terminal signal sequence. Gene 108, 73–80.

Kosik, K. S., Orecchio, L. D., Binder, L., Trojanowski, J. Q., Lee, V. M. -Y., and Lee, G. (1988). Epitopes that span the tau molecule are shared with paired helical filaments. Neuron 1, 817–825.

Kubo, M., Kincaid, R. L., and Ransom, J. T. (1994). Activation of the interleukin-4 gene is controlled by the unique calcineurin-dependent transcriptional factor NF(P). Journal of Biological Chemistry 269, 19441–6.

Kumagai, N., Benedict, S. H., Mills, G. B., and Gelland, E. W. (1988). Cyclosporin A inhibits initiation but not progression of human T cell proliferation triggered by phorbol esters and calcium ionophores. Journal of Immunology 141, 3747–52.

Kuno, T., Mukai, H., Ito, A., Chang, C. D., Kishima, K., Saito, N., and Tanaka, C. (1992). Distinct cellular expression of calcineurin A alpha and A beta in rat brain. Journal of Neurochemistry 58, 1643–51.

Kuno, T., Takeda, T., Hirai, M., Ito, A., Mukai, H., and Tanaka, C. (1989). Evidence for a second isoform of the catalytic subunit of calmodulin-dependent protein phosphatase (calcineurin A). Biochemical & Biophysical Research Communications 165, 1352–8.

Kuo, C. J., Chung, J., Fiorentino, D. F., Flanagan, W. M., Blenis, J., and Crabtree, G. R. (1992). Rapamycin selectively inhibits interleukin-2 activation of p70 $6 kinase. Nature 358, 70–3.

Kupfermann, I. (1991). Learning and memory. In Principles of neural science, E. R. Kandel, J. H. Schwartz and T. M. Jessell, eds. (East Norwalk, Conn.: Appleton & Lange), pp. 999–1003.

Labar, B., Bogdanic, V., Plavsic, F., Francetic, I., Dobric, I., Kastelan, A., Grgicevic, D., Vrtar, M., Grgic-Markulin, L., Balabanic-Kamauf, B., and (1986). Cyclosporin neurotoxicity in patients treated with allogeneic bone marrow transplantation. Biomedicine & Pharmacotherapy 40, 148–50.

Lalonde, R., and Cote, C. (1993). Behavioral effects of non-NMDA glutamate receptor antagonists. Neuroscience & Biobehavioral Reviews 17, 79–84.

Lane, R. J., Roche, S. W., Leung, A. A., Greco, A., and Lange, L. S. (1988). Cyclosporin neurotoxicity in cardiac transplant recipients. Journal of Neurology, Neurosurgery & Psychiatry 51, 1434–7.

Lebeau, M. C., Myagkikh, I., Rouviere-Fourmy, N., Baulieu, E. E., and Klee, C. B. (1994). Rabbit FKBP-59/HBI does not inhibit calcineurin activity in vitro. Biochemical & Biophysical Research Communications 203, 750–5.

Lester, R. A., and Jahr, C. E. (1992). NMDA channel behavior depends on agonist affinity. Journal of Neuroscience 12, 635–43.

Li, E., Bestor, T. H., and Jaenisch, R. (1992). Targeted mutation of the DNA methyltransferase gene results in embryonic lethality. Cell 69, 915–926.

Liang, K. C., Hon, W., and Davis, M. (1994). Pre- and post-training infusion of Nmethyl-D-aspartate receptor antagonists into the amygdala impair memory in an inhibitory avoidance task. Behavioral Neuroscience 108, 241–53.

Lieberman, D. N., and Mody, I. (1994). Regulation of NMDA channel function by endogenous Ca(2+)-dependent phosphatase. Nature 369, 235–9.

Lin, C. S. Boltz, R. C., Siekierka, J. J., and Sigal, N. H. (1991). FK-506 and cyclosporin A inhibit highly similar signal transduction pathways in human T lymphocytes. Cellular Immunology 133, 269–84.

Lindwall, G., and Cole, R. D. (1984). Phosphorylation affects the ability of tau protein to promote microtubule assembly. Journal of Biological Chemistry 8, 5301–5305.

Liu, J., Albers, M. W., Wandless, T. J., Luan, S., Alberg, D. G., Belshaw, P. J., Cohen, P., MacKintosh, C., Klee, C. B., and Schreiber, S. L. (1992). Inhibition of T cell signaling by immunophilin-ligand complexes correlates with loss of calcineurin phosphatase activity. Biochemistry 31, 3896–901.

Liu, J., Farmer, J. D., Jr., Lane, W. S., Friedman, J., Weissman, I., and Schreiber, S. L. (1991). Calcineurin is a common target of cyclophilin-cyclosporin A and FKBP-FK506 complexes. Cell 66, 807–15.

Liu, J. P., Sim, A. T., and Robinson, P. J. (1994). Calcineurin inhibition of dynamin I GTPase activity coupled to nerve terminal depolarization. Science 265, 970–3.

Liu, Y. C., and Storm, D. R. (1989). Dephosphorylation of neuromodulin by calcineurin. Journal of Biological Chemistry 264, 12800–4.

Lodish, H. F., and Kong, N. (1991). Cyclosporin A inhibits an initial step in folding of transferrin within the endoplasmic reticulum. Journal of Biological Chemistry 266, 14835–8.

Luban, J., Bossolt, K. L., Franke, E. K., Kalpana, G. V., and Golf, S. P. (1993). Human immunodeficiency virus type 1 Gag protein binds to cyclophilins A and B. Cell 73, 1067–78.

Ma, J., Yee, A., Brewer, H. B., Das, S., and Potter, H. (1994). Amyloid-associated proteins $\alpha_1$-antichymotrypsin and apolipoprotein E promote assembly of Alzheimer 13-protein into filaments. Nature 372, 92–94.

Maki, N., Sekiguchi, F., Nishimaki, J., Miwa, K., Hayano, T., Takahashi, N., and Suzuki, M. (1990). Complementary DNA encoding the!human T-cell FK506 binding protein, a peptidylprolyl cis-trans isomerase distinct from cyclophilin. Proceedings of the National Academy of Sciences of the United States of America 87, 5440–3.

Malenka, R. C. (1994). Synaptic plasticity in the hippocampus: LTP and LTD. Cell 78, 535–538.

Manalan, A. S., and Klee, C. B. (1983). Activation of calcineurin by limited proteolysis. Proceedings of the National Academy of Sciences of the United States of America 80, 4291–5.

Mansour, S. L., Thomas, K. R., and Capecchi, M. R. (1988). Disruption of the proto-oncogene int-2 in mouse embryo-derived stem cells: a general strategy for targeting mutations to non-selectable genes. Nature 336, 348–352.

Martensen, T. M., Martin, B. M., and Kincaid, R. L. (1989). Identification of the site on calcineurin phosphorylated by Ca2+iCaM-dependent kinase II: modification of the CaM-binding domain. Biochemistry 28, 9243–7.

Martin, M., and Wiederrecht, G. A filter-based, 96-well microtiter plate calcineurin phosphatase assay. Immunol. Methods.

Massol, N., Lebeau, M. C., Renoir, J. M., Faber, L. E., and Baulieu, E. E. (1992). Rabbit FKBP59-heat shock protein binding immunophilin (HBI) is a calmodulin binding protein. Biochem. Biophys. Res. Comm. 187, 1330–1333.

Mathis, D. J., Benoist, C., Williams, V. E. n., Kanter, M., and McDevitt, H. O. (1983). Several mechanisms can account for defective E alpha gene expression in different mouse haplotypes. Proceedings of the National Academy of Sciences of the United States of America 80, 273–7.

Matthies, H., and Reymann, K. G. (1993). Protein kinase A inhibitors prevent the maintenance of hippocampal long-term potentiation. NeuroReport 4, 712–714.

Mattila, P. S., Ullman, K. S., Fiering, S., Emmel, E. A., McCutcheon, M., Crabtree, G. R., and Herzenberg, L. A. (1990). The actions of cyclosporin A and FK506 suggest a novel step in the activation of T lymphocytes. EMBO Journal 9, 4425–33.

McCaffrey, P. G., Luo, C., Kerppola, T. K., Jain, J., Badalian, T. M., Ho, A. M., Burgeon, E., Lane, W. S., Lambert, J. N., Curran, T., and (1993). Isolation of the cyclosporin-sensitive T cell transcription factor NFATp. Science 262, 750–4.

McCaffrey, P. G., Perrino, B. A., Soderling, T. R., and Rao, A. (1993). NF-ATp, a T lymphocyte DNA-binding protein that is a target for calcineurin and immunosuppressive drugs. Journal of Biological Chemistry 268, 3747–52.

McKeon, F. (1991). When worlds collide: immunosuppressants meet protein phosphatases. [Review]. Cell 66, 823–6.

McPartlin, A. E., Barker, H. M., and Cohen, P. T. W. (1991). Identification of a third alternatively spliced cDNA encoding the catalytic subunit of protein phosphatase 2B. Biochem. Biophys. Act. 1088, 308–31 0.

Menegaux, F., Keeffe, E. B., Andrews, B. T., Egawa, H., Monge, H., Concepcion, W., So, S. K., and Esquivel, C. O. (1994). Neurological complications of liver transplantation in adult versus pediatric patients. Transplantation 58, 447–50.

Metcalfe, S., Alexander, D., and Turner, J. (1994). FK506 and cyclosporin A each inhibit antigen-specific signaling in the T cell line 171 in the absence of a calcium signal. Cellular Immunology 158, 46–58.

Miach, P. J. (1986). Cyclosporin A in organ transplantation. Medical Journal of Australia 145, 146–50.

Middleton, F. A., and Strick, P. L. (1994). Anatomical evidence for cerebellar and basal ganglia involvement in higher cognitive function. Science 266, 458461.

Milan, D., Griffith, J., Su, M., Price, E. R., and McKeon, F. (1994). The latch region of calcineurin B is involved in both immunosuppressant-immunophilin complex docking and phosphatase activation. Cell 79, 437–47.

Miller, N. E., and Weiss, J. M. (1969). Effects of the somatic orvisceral responses to punishment. In Punishment and Aversive Behavior, B. A. Campbell and R. M. Church, eds. (New York: Appleton-Century-Crofts). Mishkin, M. (1978). Memory in monkeys severely impaired by combined but not by separate removal of amygdala and hippocampus. Nature 273, 297–8.

Miyata, Y., M. Hoshi, E. Nishida, Y. Minami, and H. Sakai (1986). Binding of reassembled from neurofilament 70 KDa subunit protein. Journal of Biological Chemistry 261, 13026–13030.

Montoro, R. J., Diaz-Nido, J., Avila, J., and Lopez-Barneo, J. (1993). N-methyl-Daspartate stimulates the dephosphorylation of the microtubule-associated protein 2 and potentiates excitatory synaptic pathways in the rat hippocampus. Neuroscience 54, 859–71.

Morice, W. G., Brunn, G. J., Wiederrecht, G., Siekierka, J. J., and Abraham, R. T. (1993). Rapamycin-induced inhibition of p34cdc2 kinase activation is associated with G1/S-phase growth arrest in T lymphocytes. Journal of Biological Chemistry 268, 3734–8.

Morice, W. G., Wiederrecht, G., Brunn, G. J., Siekierka, J. J., and Abraham, R. T. (1993). Rapamycin inhibition of interleukin-2-dependent p33$^{cdk2}$ and p34$^{cdc2}$ kinase activation in T lymphocytes. J. Biol. Chem. 268.

Morris, R: G. M. (1981). Spatial localization does not require the presence of local cues. Learning Motiv. 12.

Morris, R. G. M., Garrud, P., Rawlins, J. N. P., and O'Keefe, J. (1982). Place navigation impaired in rats with hippocampal lesions. Nature 297, 681–683.

Mortensen, R. M., Conner, D. A., Chao, S., Geisterfer-Lowrance, A. A. T., and Seidman, J. G. (1992). Production of homozygous mutant ES cells with a single targeting construct. Mol. Cell. Biol. 12, 2391–2395.

Mueller, A. R., Platz, K. P., Bechstein, W. O., Schattenfroh, N., StoltenburgDidinger, G., Blumhardt, G., Christe, W., and Neuhaus, P. (1994). Neurotoxicity after orthotopic liver transplantation. A comparison between cyclosporine and FK506. Transplantation 58, 155–70.

Mukai, H., Chang, C. D., Tanaka, H., Ito, A., Kuno, T., and Tanaka, C. (1991). cDNA cloning of a novel testis-specific calcineurin B-like protein. Biochemical & Biophysical Research Communications 179, 1325–30.

Mulkey, R. M., Endo, S., Shenolikar, S., and Malenka, R. C. (1994). Involvement of a calcineurin/inhibitor-1 phosphatase cascade in hippocampal long-term depression. Nature 369, 486–8.

Muramatsu, T., Giri, P. R., Higuchi, S., and Kincaid, R. L. (1992). Molecular cloning of a calmodulin-dependent phosphatase from murine testis: Identification of a developmentally expressed nonneural isozyme. Proc. Natl. Acad. Sci. USA 89, 529–533.

Murphy, B. J., Rossie, S., De Jongh, K. S., and Catterall, W. A. (1993). Identification of the sites of selective phosphorylation and dephosphorylation of the rat brain Na+ channel alpha subunit by cAMP-dependent protein kinase and phosphoprotein phosphatases. Journal of Biological Chemistry 268, 27355–62.

Nadel, L., Willner, J., and Kurtz, E. (1985). Cognitive maps and environmental context. In Context and learning, P. D. Balsam and A. Tomie, eds. (Hillsdale, N.J.: Erlbaum), pp. 385–406.

Nakamura, T., Liu, Y., Hirata, D., Namba, H., Harada, S., Hirokawa, T., and Miyakawa, T. (1993). Protein phosphatase type 2B (calcineurin)-mediated, FK506-sensitive regulation of intracellular ions in yeast is an important determinant for adaptation to high salt stress conditions. EMBO Journal 12, 4063–71.

Nelson, P. A., Akselband, Y., Kawamura, A., Su, M., Tung, R. D., Rich, D. H., Kishore, V., Rosborough, S. L., DeCenzo, M. T., Livingston, D. J., and (1993). Immunosuppressive activity of [MeBm2t]1-, D-diaminobutyryl-8-, and D-diaminopropyl-8-cyclosporin analogues correlates with inhibition of calcineurin phosphatase activity. Journal of Immunology 150, 2139–47.

Nichols, R. A., Suplick, G. R., and Brown, J. M. (1994). Calcineurin-mediated protein dephosphorylation in brain nerve terminals regulates the release of glutamate. Journal of Biological Chemistry 269, 23817–23.

Nielsen, J. B., Foor, F., Siekierka, J. J., Hsu, M. J., Ramadan, N., Morin, N., Shafiee, A., Dahl, A. M., Brizuela, L., Chrebet, G., and (1992). Yeast FKBP13 is a membrane-associated FK506-binding protein encoded by the nonessential gene FKB2. Proceedings of the National Academy of Sciences of the United States of America 89, 7471–5.

Nigam, S. K., Jin, Y. J., Jin, M. J., Bush, K. T., Bierer, B. E., and Burakoff, S. J. (1993). Localization of the FK506-binding protein, FKBP 13, to the lumen of the endoplasmic reticulum. Biochemical Journal 294, 511–5.

Northrop, J. P., Ullman, K. S., and Crabtree, G. R. (1993). Characterization of the nuclear and cytoplasmic components of the lymphoid-specific nuclear factor of activated, TCells (NF-AT). The Journal of Biological Chemistry 268, 2917–2923.

O'Keefe, J., and Nadel, L. (1978). The Hippocampus as a Cognitive Map (Oxford: Oxford University Press).

O'Keefe, S. J., Tamura, J., Kincaid, R. L., Tocci, M. J., and O'Neill, E. A. (1992). FK-506- and CsA-sensitive activation of the interleukin-2 promoter by calcineurin. Nature 357, 692–4.

Ochiai, T., Nakajima, K., Nagata, M., Hori, S., Asano, T., and Isono, K. (1987). Studies of the induction and maintenance of long-term graft acceptance by treatment with FK506 in heterotopic cardiac allotransplantation in rats. Transplantation 44, 734–8.

Ochiai, T., Sakamoto, K., Nagata, M., Nakajima, K., Goto, T., Hori, S., Kenmochi, T., Nakagori, T., Asano, T., and Isono, K. (1988). Studies on FK506 in experimental organ transplantation. Transplantation Proceedings 20, 209–14.

Orosz, C. G., Fidelus, R. K., Roopenian, D. C., Widmer, M. B., Ferguson, R. M., and Bach, F. H. (1982). Analysis of cloned T cell function. I. Dissection of cloned T cell proliferative responses using cyclosporin A. Journal of Immunology 129, 1865–8.

Paliogianni, F., Kincaid, R. L., and Boumpas, D. T. (1993). Prostaglandin E2 and other cyclic AMP elevating agents inhibit interleukin 2 gene transcription by counteracting calcineurin-dependent pathways. Journal of Experimental Medicine 178, 1813–7.

Papadopoulos, V., Brown, A. S., and Hall, P. F. (1990). Calcium-calmodulindependent phosphorylation of cytoskeletal proteins from adrenal cells. Molecular & Cellular Endocrinology 74, 109–23.

Papadopoulos, V., Brown, A. S., and Hall, P. F. (1989). Isolation and characterization of calcineurin from adrenal cell cytoskeleton: identification of substrates for Ca2+-calmodulin-dependent phosphatase activity. Molecular & Cellular Endocrinology 63, 23–38.

Partaledis, J. A., and Berlin, V. (1993). The FKB2 gene of Saccharomyces cerevisiae, encoding the immunosuppressant-binding protein FKBP-13, is regulated in response to accumulation of unfolded proteins in the endoplasmic reticulum. Proceedings of the National Academy of Sciences of the United States of America 90, 5450–4.

Phillips, R. G., and LeDoux, J. E. (1992). Differential contribution of amygdala and hippocampus to cued and contextual fear conditioning. Behavioral Neuroscience 106, 274–85.

Price, E. R., Zydowsky, L. D., Jin, M. J., Baker, C. H., McKeon, F. D., and Walsh, C. T. (1991). Human cyclophilin B: a second cyclophilin gone encodes a peptidyl-prolyl isomerase with a signal sequence. Proceedings of the National Academy of Sciences of the United States of America 88, 1903–7.

Racusen, L. C., McCrindle, B. W., Christenson, M., Fivush, B., and Fisher, R. S. (1990). Cyclosporine lowers seizure threshold in an experimental model of electroshock-induced seizures in Munich-Wistar rats. Life Sciences 46, 1021–6.

Randak, C., Brabletz, T., Hergenrother, M., Sobotta, I., and Serfling, E. (1990). Cyclosporin A suppresses the expression of the interleukin 2 gone by inhibiting the binding of lymphocyte-specific factors to the IL-2 enhancer. EMBO Journal 9, 2529–36.

Rao, A. (1994). NF-ATp: a transcription factor required for the co-ordinate induction of several cytokine genes. Immunology Today 15, 274–81.

Reece, D. E., Frei-Lahr, D. A., Shepherd, J. D., Dorovini-Zis, K., Gascoyne, R. D., Graeb, D. A., Spinelii, J. J., Barnett, M. J., Klingemann, H. G., Herzig, G. P., and (1991'). Neurologic complications in allogeneic bone marrow transplant patients receiving cyclosporin. Bone Marrow Transplantation 8, 393–401.

Room, G. H., Cook, L. A., and Vilcek, J. (1983). Gamma interferon synthesis by human thymocytes and T lymphocytes inhibited by cyclosporin A. Science 221, 63–5.

Represa, A., G. Le Gal La Saile, Y. Ben-Ari (1989). Hippocampal plasticity in the kindling model of epilepsy in rats. Neuroscience Letters 99, 345–350. Rodriguez, E., Delucchi, A., and Cano, F. (1992). [Neurotoxicity caused by cyclosporin A in renal transplantation in children]. Revista Medica de Chile 120, 300–3.

Rosen, M. K., Standaert, R. F., Galat, A., Nakatsuka, M., and Schreiber, S. L. (1990). Inhibition of FKBP rotamase activity by immunosuppressant FK506: twisted amide surrogate. Science 248, 863–6.

Rosenbaum, L. C., Malencik, D. A., Anderson, S. R., Tota, M. R., and Schimerlik, M. I. (1987). Phosphorylation of the porcine atrial muscarinic acetylcholine receptor by cyclic AMP dependent protein kinase. Biochemistry 26, 8183–8.

Rossie, S., and Catterall, W. A. (1987). Cyclic-AMP-dependent phosphorylation of voltage-sensitive sodium channels in primary cultures of rat brain neurons. Journal of Biological Chemistry 262, 12735–44. Rozin, P. (1976). The psychobiological approach to human memory. In Neural mechanisms of learning and memory, M. R. Rosensweig and E. L. Bennett, eds. (Cambridge, Mass.: MIT Press), pp. 3–46.

Rudy, J. W. (1993). Contextual conditioning and auditory cue conditioning dissociate during development. Behavioral Neuroscience 107, 887–91.

Rudy, J. W., and Morledge, P. (1994). Ontogeny of contextual fear conditioning in rats: implications for consolidation, infantile amnesia, and hippocampal system function. Behavioral Neuroscience 108, 227–34.

Sabatini, D. M., Erdjument-Bromage, H., Lui, M., Tempst, P., and Snyder, S. H. (1994). RAFT1:a mammalian protein that binds to FKBP12 in a rapamyc-independent fashion and is homologous to yeast TORs. Cell 78, 35–43.

Sah, P., Hestrin, S., and Nicoll, R. A. (1989). Tonic activation of NMDA receptors by ambient glutamate excitability of neurons. Science 246, 815–8.

Sawada, S., Suzuki, G., Kawase, Y., and Takaku, F. (1987). Novel immunosuppressive agent, FK506. In vitro effects on the cloned T cell activation. Journal of Immunology 139, 1797–803.

Sawada, S., Suzuki, G., Kawase, Y., and Takaku, F. (1987). Novel immunosuppressive agent, FK506. In vitro effects on the cloned T cell activation. Journal of Immunology 139, 1797–803.

Schneuwly, S., Shortridge, R. D., Larrivee, D. C., Ono, T., Ozaki, M., and Pak, W. L. (1989). Proc. Natl. Acad. Sci. (USA) 86, 5390–5394.

Schonbrunner, E. R., Mayer, S., Tropschug, M., Fischer, G., Takahashi, N., and Schmid, F. X. (1991). Catalysis of protein folding by cyclophilins from different species. Journal of Biological Chemistry 266, 3630–5.

Schreiber, S. L. (1991). Chemistry and biology of the immunophilins and their immunosuppressive ligands. Science 251, 283–287.

Schreiber, S. L. (1992). Immunophilin-sensitive protein phosphatase action in cell signaling pathways. Cell 70, 365–368.

Schreiber, S. L., and Crabtree, G. R. (1992). The mechanism of action of cyclosporin A and FK506. Immunology Today 13, 136–42.

Schwaninger, M., Blume, R., Oetjen, E., and Knepel, W. (1993). The immunosuppressive drugs cyclosporin A and FK506 inhibit calcineurin phosphatase activity and gene transcription mediated through the cAMPresponsive element in a nonimmune cell line. Naunyn-Schmiedebergs Archives of Pharmacology 348, 541–5.

Schwaninger, M., Blume, R., Oetjen, E., Lux, G., and Knepel, W. (1993). Inhibition of cAMP-responsive element-mediated gene transcription by cyclosporin A and FK506 after membrane depolarization. Journal of Biological Chemistry 268, 23111–5.

Sewell, T. J., Lam, E., Martin, M. M., Leszyk, J., Weidner, J., Calaycay, J., Griffin, P., Williams, H., Hung, S., Cryan, J., and (1994). Inhibition of calcineurin by a novel FK-506-binding protein. Journal of Biological Chemistry 269, 21094–102.

Sewell, T. J., Lam, E., Martin, M. M., Leszyk, J., Weidner, J., Calaycay, J., Griffin, P., Williams, H., Hung, S., Cryan, J., and (1994). Inhibition of calcineurin by a novel FK-506-binding protein. Journal of Biological Chemistry 269, 21094–102.

Sharma, R. K., and Wang, J. H. (1986). Calmodulin and Ca2+-dependent phosphorylation and dephosphorylation of 63-kDa subunit-containing bovine brain calmodulin-stimulated cyclic nucleotide phosphodiesterase isozyme. Journal of Biological Chemistry 261, 1322–8.

Sharma, R. K., and Wang, J. H. (1986). Regulation of cAMP concentration by calmodulin-dependent cyclic nucleotide phosphodiesterase. Biochemistry & Cell Biology 64, 1072–80.

Shaw, J.-P., Utz, P. J., Durand, D. B., Toole, J. J., Emmel, E. A., and Crabtree, G. R. (1988). Identification of a putative regulator of early T cell activation genes. Science 241, 202–205.

Shi, Y., Sahai, B. M., and Green, D. R. (1989). Cyclosporin A inhibits activationinduced ceil death in T-cell hybridomas and thymocytes. Nature 339, 625–626.

Shieh, B. H., Stamnes, M. A., Seavello, S., Harris, G. L., and Zuker, C. S. (1989). Nature 338, 67–70.

Shinkai, Y., Rathbun, G., Lam, K., Oltz, E. M., Stewart, V., Mendelsohn, M., Charron, J., Datta, M., Young, F., Stall, A. M., and Alt, F. W. (1992). RAG-2deficient mice lack mature lymphocytes owing to inability to initiate V(D)J rearrangement. Cell 68, 855–867.

Siekierka, J. J., Hung, S. H., Poe, M., Lin, C. S., and Sigal, N. H. (1989). A cytosolic binding protein for the immunosuppressant FK506 has peptidyl-prolyl isomerase activity but is distinct from cyclophilin. Nature 341, 755–7.

Siekierka, J. J., and Sigal, N. H. (1992). FK-506 and cyclosporin A: immunosuppressive mechanism of action and beyond. Current Opinion in Immunology 4, 548–52.

Sigal, N. H., Dumont, F., Durette, P., Siekierka, J. J., Peterson, L., Rich, D. H., Dunlap, B. E., Staruch, M. J., Melino, M. R., Koprak, S. L., and (1991). Is cyclophilin involved in the immunosuppressive and nephrotoxic mechanism of action of cyclosporin A? Journal of Experimental Medicine 173, 619–2.

Sigal, N. H., and Dumont, F. J. (1992). Cyclosporin A, FK-506, and rapamycin: pharmacologic. Annual Review of Immunology 10, 519–60.

Silva, A. J., Paylor, R., Wehner, J. M., and Tonegawa, S. (1992). Impaired spatial learning in alpha-calcium-calmodulin kinase II mutant mice [see comments]. Science 257, 206–11.

Silva, A. J., Stevens, C. F., Tonegawa, S., and Wang, Y. (1992). Deficient hippocampal long-term potentiation in alpha-calcium-calmodulin kinase II mutant mice [see comments]. Science 257, 201–6.

Singh, T. J, and Wang, J. H. (1987). Phosphorylation of calcineurin by glycogen synthase (casein) kinase-1. Biochemistry & Cell Biology 65, 917–21.

Snyder, S. H., and Sabatini, D. M. (1995). Immunophilins and the nervous system. Nature Medicine 1, 32–37.

Spik, G., Haendler, B., Delmas, O., Mariller, C., Chamoux, M., Maes, P., Tartar, A., Montreuil, J., Stedman, K., Kocher, H. P., and (1991). A novel secreted cyclophilin-like protein (SCYLP). Journal of Biological Chemistry 266, 10735–8.

Squire, L., Cohen, N., and Nadel, L. (1984). The medial temporal region and memory consolidation: A new hypothesis. In Memory consolidation, H. Wingartner and E. Parker, eds. (Hillsdale, N.J.: Erlbaum), pp. 185–210.

Squire, L. R. (1987). Memory and Brain (New York: Oxford University Press). Squire, L. R. (1992). Memory and the hippocampus: a synthesis from findings with rats, monkeys, and humans. Psych. Rev. 99, 195–231.

Squire, L. R., and Zola-Morgan, S. (1991). The medial temporal lobe memory system. Science 253, 1380–1386.

Standaert, R. F., Galat, A., Verdine, G. L., and Schreiber, S. L. (1990). Molecular cloning and overexpression of the human FK506-binding protein FKBP. Nature 346, 671–4.

Steiner, J. P., Dawson, T. M., Fotuhi, M., Glatt, C. E., Snowman, A. M., Cohen, N., and Snyder, S. H. (1992). High brain densities of the immunophilin FKBP colocalized with calcineurin. Nature 358, 584–7.

Steinmann, B., Bruckner, P., and Superti-Furga, A. (1991). Cyclosporin A slows collagen triple-helix formation in vivo: indirect evidence for a physiologic role of peptidyl-prolyl cis-trans-isomerase. Journal of Biological Chemistry 266, 1299303.

Stemmer, P. M., and Klee, C. B. (1994). Dual calcium ion regulation of calcineurin by calmodulin and calcineurin B. Biochemistry 33, 6859–66.

Stewart, A. A., Ingebritsen, T. S., Manalan, A., Klee, C. B., and Cohen, P. (1982). Discovery of a Ca2+– and calmodulin-dependent protein phosphatase: probable identity with calcineurin (CaM-BP80). FEBS Letters 137, 80–4.

Sutherland, R. J., and Rudy, J. W. (1989). Configural association theory: the role of the hippocampus formation in learning, memory and amnesia. Psychobiol. 17, 129–144.

Sutherland, R. J., Whishaw, I. Q., and Kolb, B. (1983). A behavioural analysis of spatial localization following electrolytic, kainate- or colchicine-induced damage to the hippocampal formation in the rat. Behavioural Brain Research 7, 133–153.

Sutula, T., X. X. He, J. Cavazos, and G. Scott (1988). Synaptic reorganization in the hippocampus induced by abnormal functional activity. Science 239, 1147–1150.

Swanson, S. K., Born, T., Zydowsky, L. D., Cho, H., Chang, H. Y., Walsh, C. T., and Rusnak, F. (1992). Cyclosporin-mediated inhibition of bovine calcineurin by cyclophilins A and B. Proceedings of the National Academy of Sciences of the United States of America 89, 3741–5.

Sykes, K., Gething, M. J., and Sambrook, J. (1993). Proline isomerases function during heat shock. Proceedings of the National Academy of Sciences of the United States of America 90, 5853–7.

Takahashi, N., Hayano, T., and Suzuki, M. (1989). Peptidyl-prolyl cis-trans isomerase is the cyclosporin A-binding protein cyclophilin. Nature 337, 473–5.

Takaishi, T., Saito, N., Kuno, T., and Tanaka, C. (1991 Differential distribution of the mRNA encoding two isoforms of the catalytic subunit of calcineurin in the rat brain. Biochemical & Biophysical Research Communications 174, 393–8.

Tallant, E, A., Brumley, L. M., and Wallace, R. W. (1988). Activation of a calmodulin-dependent phosphatase by a Ca2+– dependent protease. Biochemistry 27, 2205–11.

Tanaka, T., Takeda, M., Niigawa, H., Hariguchi, S., and Nishimura, T. (1993). Phosphorylated neurofilament accumulation in neuronal perikarya by cyclosporin A injection in rat brain. Methods & Findings in Experimental & Clinical Pharmacology 15, 77–87.

Thaii, M., Bukovsky, A., Kondo, E., Rosenwirth, B., Walsh, C. T., Sodroski, J., and Gottlinger, H. G. (1994). Functional association of cyclophilin A with HIV-1 virions [see comments]. Nature 372, 363–5.

Thomas, K. R., and Capecchi, M. R. (1987). Site-directed mutagenesis by gene targeting in mouse embryo-derived stem cells. Cell 65, 503–512.

EXAMPLE 4

Assessment of Alzheimer's PHF Tau in Mice Lacking Calcineurin

References cited in Example 4 are those included in the subject application immediately following Example 4. Mice lacking calcineurin were produced as described above.
Protein Processing and Assay:

Brains were homogenized in 50 mM tris/0.2 mM EDTA, with five passes (up and down) in a ground glass homogenizer. Homogenates were assayed for protein in Bradford's Coomassie Blue binding assay (Bradford , 1976) according to the manufacturer's (Bio-Rad; Richmond, Calif.) instructions. Protein assays were performed in duplicate. Following mixing of the sample with the dye reagent, the absorbance was read at 600 nm.
Sodium Dodecyl Sulphate-polyacrylamide Gel Electrophoresis (SDS-PAGE)

The protein fractions were subjected to SDS-PAGE in 4–2020% gradient gels using Laemmli discontinuous buffer system (Laemmli, et al., 1970). Twenty $\mu$g of the boiled samples and of protein standards (Amersham, Arlington Heights, Ill.) were loaded in each well and run at a constant current of 20 mA/gel. The gels were stained with Coomassie Blue R-250 or silver (Bio-Rad; Richmond, Calif.).
Western Blotting and Immunostaining Duplicate SDS-PAGE gels were used immediately for electrophoretic transfer. The transfer was carried out using 0.025 M Tris, 0.192 M glycine, 15% methanol, pH 8.3 (Towbin et al., 1979). The proteins were transferred overnight in the cold room at a constant voltage of 30 volts to Immobilon-P membranes (Millipore, Bedford, Mass.). Upon the termination of the transfer, the membranes were blocked by incubating with either 5% (w/v) bovine serum albumin or 5% non-fat milk in 10 mM tris-buffered saline pH 7.4, 0.1% Tween-20 (TBST) for 1 hour. After blocking non-specific binding sites, the membranes were incubated for 1–2 hours with the primary antibody solution at a titer recommended by the manufacturer or determine empirically in the laboratory. The membranes were then washed 1×15 and 2×5 minutes with TBST. After washing, the secondary antibody solution, horseradish peroxidase-conjugated anti mouse IgG, (Pierce, Rockford, Ill.) was added and incubated for 1 hour. Then, the membranes were washed again 1×15 and 4×5 minutes as before. The membranes were stained with the chemiluminescent substrate solution ECL (Amersham, Arlington Heights, Ill.) according to manufacturers instructions, and exposed on Kodak XAR-5 film for 1–60 min depending on intensity of bands observed. For quantitation of bands the films were scanned and the stained peaks integrated using an LKB Ultroscan XL densitometer (Pharmacia, Piscataway, N.J.).

Histochemistry and Immunocytochemistry

Mice were anesthetized with ketamine.HCl/xylazine, and perfused transcardially with Ames solution containing procaine and heparin, followed by 1% glutaraldehyde, 1% formaldehyde. Next the brains were dissected out, and placed in 4% formaldehyde. The samples were embedded in paraffin and sections were cut for histochemistry and immunocytochemistry. Sections were dre-paraffinized and some were stained with Hematoxylin and Eosin, Bielchowsky silver, Luxol Fast Blue, or Congo red as described by AFPI manual (Prophet et al., 1992). Other slides were immunostained using the ABC, and ABC-AP kits according to manufacturer's instructions (Vector, Burlingame, Calif.). To enhance the signal on fixed tissue, occasionally slides were treated with either 88% formic acid for 10 min or 0.1 M citrate pH 6.0 for 10 min in the microwave (bringing the citrate to boil).

Results

Phosphorylation-dependent antibodies were used to investigate the neuropathological effects of deleting the a isoform of the catalytic subunit (A) of calcineurin. Of particular interest was the PHF-1 monoclonal antibody that was raised against PHF purified from Alzheimer's disease brain (Greenberg et al., 1992). The antigen most clearly recognized by PHF-1 has been shown to be a phosphorylated form of the microtubule-associated protein tau. The dependent of PHF-1 antibody on the phosphorylation state of tau is demonstrated by the fact that immunostaining with PHF-1 is abolished when the PHF tau is dephosphorylated with calcineurin (Gong et al., 1994). Another antibody used in the study is τ-1 (Binder et al., 1985), which recognized dephosphorylated tau but not phosphorylated tau, allowing the specific detection of non-PHF tau. Two other antibodies that are believed to be phosphorylation independent, tau-2 and 5E2, were also tested (Kosik et al., 1988).

In the first set of experiments brain homogenates were prepared from 2–4 months old wild type mice and mice in which the expression of calcineurin was knocked out (Cn⁻), and the phosphorylation state of the proteins were probed with different antibodies. First, the expression of calcineurin was examined using a monoclonal antibody against calcineurin (Transduction Laboratories, Lexington, Ky.) and shown to be significantly suppressed in the calcineurin knock-out mice. The residual staining is probably due to calcineurin β which is expressed at lower levels in the rat brain (Kuno et al., 1992). When Western blots were immunostained with PHF-1, bands with molecular weights corresponding to tau consistently showed an increase (up to 7 fold) in the level of PHF-1 immunoreactivity in Cn⁻ samples as compared to wild type samples from age-matched litter mates. When these samples were run in parallel and stained with antibody to dephosphorylated tau (τ-1), the Cn⁻ mice had either the same or occasionally slightly lower tau staining. The fact that τ-1 immunostaining was not increased in Cn⁻ mice indicates that the increased staining with PHF-1 in the Cn⁻ mice reflects a specific increase in the PHF form of tau rather than a general increase in all forms of tau. When the blots were immunostained with the phosphorylation-independent antibodies tau-2 and 5E2 there was a slightly stronger reaction with the knock-out mice than the wild type. From these data, we conclude that the predominant effect on tau of knocking out calcineurin is a shift in its phosphorylation state, with perhaps also a slight increase in absolute tau levels.

To investigate the effect of calcineurin deletion on the phosphorylation of other cytoskeletal proteins, we probed the Western blots with various phosphorylation-dependent and independent antibodies. Normally, neurofilaments are phosphorylated to different degrees depending on their location and maturation. Their function is believed to involve modulating the axonal caliber, and the degree of neurofilament phosphorylation is believed to regulate the spacing between them (de Waegh et al., 1992). Immunostaining with an antibody (SMI32, Sternberger Monoclonals, Baltimore, Md.) that recognized non-phosphorylated neurofilaments (NF) showed that the levels-of NF proteins were not significantly different between wild type and Cn⁻ mice, although in some Cn⁻ samples there was a stronger staining of a band of ~50 KDa that might represent a cross-reactive form of tau. Immunostaining with antibodies directed against phosphorylated NF, including SMI34 and SMI310 (Sternberger Monoclonals, Baltimore, Md.), which strain intracellular and extracellular neurofibrillary tangles (NFT) respectively, showed a slightly stronger reaction with the wild type than the Cn⁻ samples, indicating that the increase in phosphorylated tau is specific and does not reflect a general increase in the phosphorylation of cytoskeletal proteins. The reduced staining of phosphorylated NF in the Cn⁻ knock-out mice could be due to a general reduction in expression of neurofilaments. Neurofilaments, which are believed to convey on axons thickness and stability, are down-regulated in regenerating neurites, which thus have a concomitant increase in the microtubule/neurofilament ratio (Hoffman et al., 1988). Finally, several other antibodies against different cytoskeletal proteins have been tested to check for different proteins and no consistent differences in immunoreactivity were observed.

Upon finding that the Cn⁻ mouse brains had a higher level of PHF immunoreactivity, we wished to determine whether some areas of the brain were more affected than others, and whether the PHF immunoreactivity is accompanied by the formation of neurofibrillary tangles. In the second set of experiments wild type and Cn⁻ mice were perfused with fixative and paraffin sections were prepared from their brains. When the seconds were stained with anti PHF antibodies, increased immunoreactivity were consistently observed in the hippocampi of Cn⁻ mice when compared to wild type. The most intense immunoreactivity was observed in the stratum lucidum of the observed region; some staining was also observed in the hilus of the dentate gyrus. In some of the Cn⁻ mice, staining was observed in both infrapyramidal and suprapyramidal layers. The PHF staining in the Cn⁻ mice did not correspond to cell bodies of granule or pyramidal cells, but based on the location and orientation is most consistent with the labeling of mossy fiber axons projecting from dentate gyrus into CA3.

The finding of PHF tau in the mossy fibers of the Cn⁻ mice prompted a parallel analysis of the localization of calcineurin. Sections labeled with anti calcineurin antibodies revealed strong staining in the hippocampus and striatum in the wild type but not in the Cn⁻ knock-outs, as expected. The difference in calcineurin levels between wild type and Cn⁻ mice was particularly large in the mossy fibers-the area strongly labeled with anti PHF antibodies in the knock-out mice, demonstrating that calcineurin is depleted in regions that exhibit increased anti PHF staining. Other regions in the hippocampus, such as CA1, showed some weak staining in the Cn⁻ mice, which could be due to the β isoform of calcineurin. More importantly, the anti calcineurin staining in wild type mice in CA1 was localized in the dendrites unlike CA3 where it was localized in mossy fiber axons. Since tau is predominantly localized in axons, it is therefore not surprising that we found no anti PHF staining in the CA1 region in the Cn⁻ mice.

Several histochemical stains were used to analyze the Cn⁻ brains for potential pathology. Staining of sections with Eosin-Hematoxylin did not reveal significant differences between the Cn⁻ and wild type. We could not identify plaques or tangles using Congo Red or Bielchowsky's silver staining, nor did we observe gross changes in myelination of neurons in these mice by staining with Luxol Fast Blue. The absence of silver staining plaques and tangles is not unexpected since in Alzheimer's disease, positive immunostaining with anti PHF antibodies long precedes any positive silver staining tangles (Braak et al, 1994). Interestingly, we observed that processes which showed strong silver staining in the CA3 region in wild type mice, did not stain in Cn⁻ mice. Bielchowsky's silver stain normally labels axons, and a loss of such argyrophilic staining has been observed in degenerating axons in ischemia. The silver staining pattern of the WT mossy fibers was reminiscent of the anti PHF staining pattern of the Cn⁻ mossy fibers, suggesting that the mossy fibers that stained positively with PHF-1 in Cn⁻ mice are not staining with silver. This result could reflect either a reduction in the number of mossy fiber axons or an alteration in their cytoskeleton, since this silver stain is believed to recognize cytoskeletal elements, particularly neurofilaments (NF).

The possibility that the neurofilaments are altered in the Cn mice was tested directly by staining sections with an anti NF antibody that recognizes the 68 KDa subunit in a phosphorylation independent manner (Zymed Laboratories, San Francisco, Calif.) We observed a much stronger NF staining in the mossy fibers of wild type mice than of Cn⁻ mice, suggesting decreased production or increased degradation of neurofilament proteins. In sum, a series of immuno- and histochemical labeling experiments indicate a reduced level of neurofilaments in the mossy fibers of the Cn⁻ mice coupled with an increase in the degree of phosphorylation of a key microtubule-associated protein, tau.

After observing the drastic alteration in cytoskeletal elements biochemically and localizing the alterations to the mossy fiber region, we wished to examine the consequences of these alterations on the ultrastructure of these axons at the electron microscope (EM) level. Half brains from perfused animals were postfixed and processed for EM. The mossy fibers were traced from the pyramidal neurons of CA3. The wild type mossy fibers had many regions with abundant neurofilaments and very little microtubules. On the other hand, in the mossy fibers of the Cn⁻ mice, there was almost a complete absence of neurofilament-rich regions coupled with an abundance of microtubules. These findings confirm our observation with immunostaining with anti neurofilament antibodies and the Bielchowsky silver staining.

Discussion

The function of the phosphatase calcineurin in the brain is not fully understood. Several roles have been proposed including regulation of the neuronal cytoskeleton through dephosphorylation of proteins such as neurofilament proteins and tau. Another proposed role is in the regulation of long term depression (LTD) through dephosphorylation of phosphatase I inhibitor and activation of the phosphatase I cascade (Mulkey et al., 1994). In addition calcineurin has been proposed to control synaptic vesicle recycling through its action on dynamin (Liu et al., 1994). These functions have been inferred either from in vitro studies or from in vivo studies in which calcineurin activity was blocked with inhibitors such as cyclosporin. One limitation to inhibition experiments is that the inhibitors used act indirectly through immunophilins, and different inhibitors bind different immunophilins. Also immunophilins have proline isomerase activities which might affect proteins other than calcineurin. By using knock-out mice in which a specific isotype of calcineurin is eliminated completely, we can directly assess the consequence of its depletion of specific end points.

The first end point we have examined is the phosphorylation of cytoskeletal proteins such as tau. Tau is a microtubule-associated protein that is localized primarily in the axons; it has been proposed to form cross-bridges between microtubules and between microtubules and neurofilaments (Hirokawa et al., 1988). Moreover, tau has been shown to stabilize microtubules and promote their assembly, a property that is likely regulated by the phosphorylation state of tau. Specifically, when tau is phosphorylated, its ability to promote microtubule assembly is diminished (Brandt et al., 1994; Dreschsel et al., 1992; Lindwall et al., 1984). Recently, it was shown that abnormally phosphorylated tau from Alzheimer's brain inhibited microtubule assembly, and that is ability to promote microtubule assembly was restored upon dephosphorylation (Alonso et al., 1994).

Tau gained special attention when it was shown that the neurofibrillary tangles that accumulate in Alzheimer's disease are composed predominantly of tau that is abnormally phosphorylated. Using antibodies against hyperphosphorylated tau, changes were detected much earlier than the development of argyrophilic staining and before the appearance of any NFT or amyloid plaques (Braak et al., 1994; Braak et al., 1994). Indeed, phosphorylation of tau has also been shown to alter its structure by making it longer and stiffer (Hagestedt et al., 1989). These findings prompted research into possible mechanisms by which tau could become hyperphosphorylated. As mentioned above, several kinases will phosphorylate tau to generate PHF-like immunoreactive isoforms and several phosphatases, including calcineurin will return PHF tau to a more normal state of phosphorylation. Calcineurin has been further implicated recently, with other phosphatases, in the formation of PHF tau by studies on biopsied human brain tissue, in which it was demonstrated that tau is normally phosphorylated but becomes dephosphorylated during tissue processing and preparation by calcineurin and other phosphatases present in normal but not Alzheimer's brains (Matsuo et al., 1994). These findings were taken to indicate that in Alzheimer's disease deficits in phosphatases such as calcineurin might underlie the accumulation of hyperphosphorylated tau. Another study that examined the levels of calcineurin in Alzheimer's and normal cerebellum and neocortex immunocytochemically found no differences in protein level between the two groups. However, calcineurin was located around some neurofibrillary tangles, and the study did not compare levels of calcineurin enzyme activity (Billingsley et al., 1994).

Our experiments reveal a clear and specific effect of deleting the major isoform of calcineurin in the mouse brain.

The most prominent effect observed was an increase in the PHF-type tau. This observation is consistent with the ability of calcineurin to convert PHF tau into normal tau in vitro (Drewes et al., 1993; Gong et al., 1994), and is the first in vivo evidence that calcineurin plays a role in the normal phosphorylation/dephosphorylation of tau. It also suggests that lowered amounts of calcineurin activity may underlie the accumulation of the PHF-(phosphorylated) form of tau in Alzheimer's disease. The fact that increased anti PHF reactivity was observed using two independent methods, Western Blotting and immuno-cytochemistry on perfused and fixed tissue, argues against the increased phosphorylation being an artifact of tissue processing where phosphatases and kinases can become activated. Although we were unable to observe NFT in the $Cn^-$ mice, we cannot rule out the possibility that they will form as the mice become older. This possibility is supported by the fact that studies that attempted to stage Alzheimer's disease have concluded that hyperphosphorylation of tau is the earliest change observed in affected brain regions (Braak et al., 1994). Alternatively, inasmuch as NFT have not been observed in mice during any neurological disease, the properties of mouse tau could preclude PHF formation. Finally, it is possible that other components are needed for the formation of the tangles, just as pathological chaperones appear to be required for the Alzheimer β-protein to polymerize into amyloid filaments (Ma et al., 1994).

The hippocampal mossy fibers which are projected from granule cells into CA3 are believed to be involved in memory and learning. Granule cells exhibit post-natal neurogenesis and have been proposed to be very plastic in terms of their ability to form new synapses. Such plasticity is normally observed in developing neurons, but persists in adjust hippocampus, presumably because of the need for constant synaptic remodeling during memory formation and processing. The plasticity of the CA3 region can be partly regulated by calcineurin and calcium. The staining of sections with an antibody against calcineurin revealed intense staining in wild type mice in the hippocampus, including the mossy fibers, where we observed the PHF immunostaining in $Cn^-$ mice. Mossy fibers have a smaller diameter than many axons, and small axons have been reported to contain a greater amount of tau relative to other MAPs as compared to large diameter axons (Harada et al., 1994). The fact might help explain the prominence of PHF staining in that region. Some regions such as CA1 exhibited anti calcineurin immunoreactivity in wild type mice but no PHF immunoreactivity in $Cn^-$ mice, presumably because calcineurin in CA1, was localized in the dendrites which normally do not contain tau. This is an interesting observation indicating that a specific phosphatase can have a predominantly axonal localization in one synapse (mossy fiber-CA-3) and a dendritic localization in another (CA3-CA1). These two major synapses of the hippocampus have been shown to differ in terms of their electrophysiological behavior and neurotransmitter modulation when studying learning paradigms such as LTP. The different calcineurin distribution between axons and dendrites suggests a possible mechanism by which these two synapses can be differently modulated-either calcineurin may be involved in synaptic plasticity-pre-synaptically or post-synaptically. It is not clear how calcineurin might effect such mechanisms, but its actions on cytoskeletal proteins such as tau and dynamin are clear candidates for altering synaptic function. Finally, it is worth mentioning that a hallmark of Alzheimer's disease is the appearance of PHF tau in the cell bodies and dendrites of CNS neurons, while normal tau is restricted to axons. The cells of the CA1 region of the hippocampus are particularly prone to developing PHF. Now that we have shown that calcineurin is the somas and dendrites of this region, rechanneling of tau to the dendrites, coupled with reduced calcineurin activity should lead to hyperphosphorylation of tau and accumulation of PHF similar to that seen in Alzheimer's disease.

The straining of mossy fibers in wild type mice by anti neurofilament antibodies and silver and the absence of such staining in $Cn^-$ mice, suggests that neurofilaments in $Cn^-$ mossy fiber axons are either absent or down-regulated. These findings were confirmed by the EM examination of the mossy fibers. There are several possible scenarios that might explain the reduction of neurofilaments in the mossy fibers. First, calcineurin might have a direct effect on neurofilaments by dephosphorylating the head region of NF. Since, inhibition of phosphatases by okadaic acid disrupts the neurofilament network, it is plausible that deleting calcineurin might result in a similar effect (Sacher et al., 1992). Second, the interaction between neurofilaments and microtubules has been shown to be stronger when the neurofilaments are dephosphorylated at the projection domain of the largest subunit (Miyasaka et al., 1993). Thus it is possible that in the granule cells of $Cn^-$ mice from which mossy fibers originate, hyperphosphorylation of neurofilaments weakens their interaction with microtubules and hence their axonal transport. Third, since tau has been shown to bind to neurofilaments as well as microtubules (Miyata et al., 1986), and that hyperphosphorylation affects tau's ability to bind and stabilize microtubules, it seems likely that hyperphosphorylation could also reduce tau binding to NF. Finally, the interactions between tau and neurofilaments and microtubules are likely to be important for axonal transport of neurofilaments which, if perturbed, would result in fewer neurofilaments to be transported and delivered to the mossy fibers. In sum, there are several means by which a phosphorylated state of tau might regulate the plasticity and stability of axons by affecting the interaction of microtubules with neuro-filaments and result in the staining and immunolabeling changes we have observed in the $Cn^-$ hippocampus.

The most intense staining for PHF we observed was in the hippocampus which has also been shown to contain the highest levels of calcineurin in the brain (Goto et al., 1986; Goto et al., 1993; Polli et al., 1991). The hippocampus is affected in a number of neurodegenerative and neurological disorders which may include alteration in protein phosphorylation. For example, as already mentioned Alzheimer's disease results in alterations in the phosphorylations of tau and particularly affects the hippocampus. The regional specificity of the PHF-1 immunostaining that was observed is also very reminiscent of the area affected in some seizures and their animal experimental models. For instance, in children with severe epilepsy there is an increase in Timm's deposits (indicating sprouting), in CA3 (Represa et al., 1989). Also, after kindling or kainic acid treatment of rats (models of epilepsy), it was observed that mossy fibers exhibit increased Timm's zinc staining in CA3 region (indicating sprouting), while the CA1 region remained unchanged (Frotscher et al., 1983; Represa et al., 1989, Sutula et al., 1988). Moreover, it has been reported that kainic acid treatment induced a transient increase in CA3 neurons staining by the Alz50 antibody which, like PHF-1, recognizes PHF tau (Elliot et al., 1993). Perhaps the specific isotype of calcineurin that has been deleted in our knock-out mice is also affected in other neurological disorders such as epilepsy.

In conclusion, we have shown that in mice in which calcineurin was knocked out, there is an increased level of PHF immunoreactivity in specific regions of the hippocampus. These findings provide the first link between calcineurin activity to PHF in vivo and are consistent with previous in vitro observations that calcineurin can convert PHF tau into normal tau by dephosphorylation. It is likely that the observed changes in tau phosphorylation and the axonal cytoskeleton underlie a perturbation in neuronal function in Cn⁻ mice. Elucidating the specific functional changes especially in the hippocampus might prove to be beneficial in understanding the normal physiology as well as the pathological manifestations in diseases such as Alzheimer's disease and epilepsy.

References:

Alonso, A. O. C., T. Zaldi, I. Grundke-lqbal, and K. lqbal (1994). Role of abnormally phosphorylated tau in the breakdown of microtubule in Alzheimer's disease. Proc. Natl, Acad. Sci. USA 91, 5562–5566.

Baumann, K., E.-M. Mandlkow, J.Biemat, H. Pwnica-Worms, and E. Mandelkow (1993). Abnormal Azholmer-like phosphorylation of tau-protein by cyclin-dependent ldin'ses cdk2 and cdk5. FESS Letters 336, 417–424.

Billingsley, M. L., O. Ellis, R. L. Kncaid, J. Martin, M. L Schmidt, V. M.-Y. Lee, andi J. O. TroJanowsid (1994). Calcineurin reactivity in Alzheimer'e disease. Experimental Neurology 126, 178–184.

Binder, L. I., A. Frankfurter, and L. I. Rabhun (1985). The distribution of tau in the mammalian central nervous system. Journal of Biological Chemistry 101, 1371–1378.

Braak, E., H. Braak, and E.-M. Mandelkow (1994). A sequence of cytoskeleton changes related to the formation of neurofibrillary tangles and neuropil threads, Acta Neuropathologica 87, 554–567.

Braak, H., E. Braak, and M. Strothjohann (1994). Abnormally phosphorylated tau protein related to the formation of nourofibrllary tangles and neuropil threads in the cerebral cortex of sheep and goat Neuroscisnce Letters 171, 1–4.

Bradford, M. M. (1976). A rapid and sensitive method for the quantitation of microgram quantities of protein utilizing the principle of protein-dye binding. Analytical Biochemistry 72, 248–254.

Brandt, R., G. Lee, D. B. Teplow, D. Shalloway, and M. Abdel-Ghany (1994). Differential effect of phosphorylation and substrate modulatlon on tau's ability to promote microtubule growth and nucleation. Journal of Biological Chemistry 269, 11776–11782.

de Waegh, S. M., V. M-Y. Lee, and S. Brady. (1992). Local modulation of neurofilament phosphorylation, axonal caliber, and slow axonal transport by myeilnating Schwann cells. 68, 451–463.

Drechsel, D. N., A. A. Hyman, M. H. Cobb, and M. W. Kirschner (1992). Modulaton of the dynamic instability of tubulin assembly by the microtubule-associated protein tau. Molecular Biology of the Cell 3, 1141–1164.

Drewes, G., E.-M. Mandelkow, K. Baumann, J. Gons, W. Merieveds, and E. Mandelkow (1993). Dephosphorylation of tau protein and Alzheimer paired helical filaments by calcineurin and phosphatase-2A FESS Letters 336, 425–432.

Elliot, E. M., M. P. Mattson, P. Vanderklish, G. Lynch, I. Chang, and R. M. Sapoisky (1993). Cortioosterone excaoerbates kainate-induced alterations in hippocampal tau immunoreactivity and spectrin protsolysis in vivo. Journal of Neurochemistry 61, 57–67.

Frotscher, M., and J. Zimmer (1983). Leslon-induced mossy fibers to the molecular layers of the rat fascia dentata: Identification of postsynaptic granule cells by the golgi E-M technique. Journal of Comparatve Neurology, 299–311.

Goedert, M. (1993). Tau protein and the neurofibrillary pathology of Alzhelmer's disease. Trends In the Neurosciences 16, 460–465.

Gong, C. X., T. J. Singh, I. Grundke-lqbal, and K. Iqbal (1994). Alzheimer's disease abnormally phosphorylated τ is dephosphorylated by protein phosphalase-2B (caslcineurin). Jourmal of Neurochemistry 62, 803–806.

Goto, S., Y. Matsukado, Y. Mihara, N. Inuoe, and E. Miyamoto (1986). Calcineurin In human brain and Its relation to. extrapyramldal system. Acta Neuropathologica 72, 150–156.

Goto, S., S. Nagahiro, K. Korematsu, Y. Ushlo, K. Fukunaga, E. Miyamoto, and W. Hofer (1993). Cellular colocalization of calclum/calmodulin-dependent protein kinase II and calcineurin in the rat cerebral cortex and hippocampus. Neuroscience Letters 149, 189–192.

Greenberg, S. G., P. Davies, J. D. Schein, and L. I. Binder (1992). Hydrofluoric acid τ treated PHF proteins display the same biochemical properties as normal τ. Journal of Biological Chemistry 267, 564–569.

Greenberg, S. M., E. H. Koo, D. J. Selkoe, W. Q. Qui, and K. S. Kosik (1994). Secreted␣-amyloid precursor protein stimulates mitogen-activated protein kinase and enhances τ phosphorylation. Proc. Natl. Acad. Sci. USA 91, 7104–7108.

Greenwood, J. A., C. W. Scott, R. C. Spreen, C. B. Caputo, and G. W. Johnson (1994). Casein kinase II preferentially phosphorylates human tau Isoforms containing an amino-terminal insert. Identification of threonine-39 as the primary phosphate acceptor. Journal of Biological Chemistry 269, 43734380.

Hagestedt, T., B. Lichtenberg, H. Wille, H. Mandelkow, and E. Mandelkow (1989). Tau protein becomes long and stiff upon phosphorylation: correlaton between paracrystalline structure and degree of phosphorylation. Journal of Cell Biology 709, 1643–1651.

Hanger, D. P., K. Hughes, J. R. Woodgett, J-P. Brion, and B. H. Anderton (1992). Glycogen synthase kinase-3 induces Alzheimer's disease-like phosphorylation of tau: generation of paired heilical filament epitopes and neuronal localisaton of the kinase. Neuroscience Letters 147, 58–62.

Harada, A., K. Oguchl, S. Okabe, J. Kuno, S. Terada, T. Ohshlma, R. Sato-Yoshitake, Y. Takei, T. Noda, and N. Hirokawa. (1994). Altered microtubule organization In small-calibre axons of mice lacking tau protein. 369, 488–491.

Hirokawa, N., Y. Shiomura, and S. Okabe (1988). Tau proteins: the molecular structure and mode of binding on microtubules. Journal of Cell Biology 107, 1449–1459.

Hoffman, P. N., and D. W. Cleveland (1988). Neurofilament and tubulin expression recapitulates the developmental pattern during axonal regeneration: Induction of a specific β-tubulin Isotype. Proc. Natl. Acad. Sci. USA 65, 4530–4533.

Koslk, K. S., L. D. Oreochio, L. Binder, J. Q. Trojanowski, V. M.-Y. Lee, and G. Lee (1988). Epftopes that span the tau molecule are shared with paired helical filaments. Neuron 1, 817–825.

Kuno, T., H. Mukal, A. Ito, C-D. Chang, K. Kishima, N. Salto, and C. Tanaka. (1992). Distinct cellular expression of calcineurin Aα and Aβ In rat brain. Journal of Neurochemistry 58, 1643–1651.

Laemml, U. K. (1970). Cleavage of structural proteins during the assembly of the head of bacteriophage T4. Nature 227, 680–85.

Lindwall, G., and R. D. Cole (1984). Phosphorylation affects the ability of tau protein to promote microtubule assembly. Journal of Biological Chemistry 8, 5301–5305.

Llu, J.-P., A. T. R. Sim, and P. J. Robinson (1994). Calcinsurin inhibition of dynamin I GTPase activity coupled to nerve terminal depolarization. Science 265, 979–973.

Ma, J., A. Yee, H. B. Brewer, S. Das, and H. Potter (1994). Amyloid-associated proteins $\alpha_1$-antichymotrypsin and apolipoprotein E promote assembly of Alzhelmer β-protein into filaments. Nature 372, 92–94.

Matsuo, E. S., R-W Shin, M. L. Billingsley, A. Van deVoorde, M. O'Connor, J. Q. Trojanowski, And M.-Y. Lee (1994). Biopsy-derived adult human brain tau is phosphorylated at many of the same sites as Alzheimer's disease paired helical filament tau. Neuron 13, 989–1002.

Mlyasaka, H., S. Okabe, K. Ishiguro, T. Uchida, and N. Hirokawa (1993). Interaction of the tall domain of high molecular weight subunits of neurofilaments with the COOH-terminal region of tubulin and Its regulation by τ protein kinase II. Journal of Biological Chemistry 268, 22695–22702.

Miyata, Y., M. Hoshi, E. Nishida, Y. Minami, and H. Sakai (1986). Binding of microtubule-associated protein 2 and tau to the intermediate filament reassembled from neurofilament 70 KDa subunit protein. Journal of Biological Chemistry 261, 13026–13030.

Mulkey, R. M., S. Endo, S. Shenolikat, and R. C. Malenka (1994). Involvement of calcineurinlnhibitor-1 phosphatase cascade In hippocampal long-term depression. Nature 369, 486488.

Polli, J. W., M. L. Billingsley, and R. L. Kincaid (1991). Expression of the calcium-dependent protein phosphatase, calcineurin, In rat brain: developmental patterns and the role of nigrostriatal innovation. Developmental Brain Research 63, 105–119.

Prophet, E. D., B. Mills, J. B. Arrington, and L. H. Sobin. (1992). Laboratory Methods in Histotechnology (Washington, D.C.: Armed Forces Institute of Pathology).

Represa, A., O. Robain, E. Tremblay, Y, Ben-Ari (1989). Hippocampal plasticity in childhood epilepsy. Neuroscience Letters 99, 351–355.

Represa, A., G. Le Gal La Salle, Y. Ben-Ari (1989). Hippocampal plasticity in the kindling model of epilepsy In rats. Neuroscience Letters 99, 345–350.

Robertson, J., T. L. F. Loving, M. Goedert, R. Jakes, K. J. Murray, B. H. Anderton, and D. P. Hanger. (1993). Phosphorylation of tau by cyclic-AMP-dependent protein kinase. Dementia 4, 256–263.

Sacher, M. G., E. S. Athlan, and W. E. Mushynski. (1992). Okadaic acid Induces the rapid and reversible disruption of the neurofilament network In rat dorsal root ganglion neurons. 186, 524–530.

Steiner, B., E.-M. Mandelkow, J. Biernat, N. Gustke, H. E. Meyer, B. Schmldt, G. Mieskes, H. D. Sollng, D. Drechsel, M. W. Kirschner, M. Goedert, and E. Mandelkow. (1990). Phosphorylation of microtubule-associated protein tau: Identification of the site for $Ca^{2+}$-calmodulin dependent kinase and relationship with tau phosphorylation In Alzheimer tangles. The EMBO Journal 9, 3539–3544.

Sutula, T., X. X. He, J. Cavazos, and G. Scott (1988). Synaptic reorganization in the hippocampus induced by abnormal functional activity. Science 239, 1147–1150.

Towbin, H., T. Stashein, and J. Gordon. (1979). Electrophoretic transfer of proteins from polyacryiamide gels to nitrocellulose sheets: procedure and some applications. Proc. Natl. Acad, Sci. USA 76, 4350–4354.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of identifying an agent that reduces the phosphorylation of tau protein in the nervous system of a mammal, comprising the steps of:
   a) administering to a transgenic mouse whose genome comprises a genetically engineered homozygous disruption of the endogenous calcineurin A α isoform (CNAα) gene, wherein no functional CNAα is produced by said mouse, and wherein said mouse exhibits a phenotype of defects in Y cell immunity, ataxia, seizures, weight loss, reduced life expectancy and accumulation of endogenous phosphorylated tau protein an agent to be assessed for its ability to reduce phosphorylation of tau protein;
   b) determining the extent to which phosphorylation of tau protein occurs in the nervous system of the transgenic mouse to which the agent is administered; and
   c) comparing the extent determined in b) to the extent to which phosphorylation occurs in the nervous system of an appropriate control,
wherein if phosphorylation occurs to a lesser extent in the nervous system of the transgenic mouse to which the agent is administered than in the nervous system of the control, the agent reduces phosphorylation of tau protein.

2. A method of claim 1 wherein in step b) the extent to which phosphorylation occurs is determined by:
   a) obtaining brain cells from said transgenic mouse;
   b) treating said brain cells so as to render the tau protein in said brain cells available for binding with anti-paired helical fragment antibodies; and p1 c) detecting binding of the antibodies to tau protein, wherein less binding as compared to the control indicates a reduction in the phosphorylation of tau protein.

3. A Transgenic mouse whose genome comprises a genetically engineered homozygous disruption of the endogenous calcineurin A α isoform (CNAα) gene, wherein no functional CNAα is produced by said mouse, and wherein said mouse exhibits a phenotype of defects in Y cell immunity, ataxia, seizures, weight loss, reduced life expectancy and accumulation of endogenous phosphorylated tau protein.

4. A method of making a transgenic mouse whose genome comprises a genetically engineered homozygous disruption of the endogenous calcineurin A α isoform (CNAα) gene, wherein no functional CNAα is produced by said mouse, and wherein said mouse exhibits a phenotype of defects in Y cell immunity, ataxia, seizures, weight loss, reduced life expectancy and accumulation of endogenous phosphorylated tau protein comprising, p1 a) introducing a targeting vector into embryonic stem cells thereby producing a transgenic embryonic stem cell comprising a disrupted CNAα gene, p1 b) introducing said embryonic stem cell into a blastocyst; p1 c) introducing said blastocyst into the uterus of a pseudopregnant mouse; p1 d) allowing the pseudopregnant mouse to give birth; p1 e) detecting transgenic progeny; p1 f) breeding the transgenic progeny to produce a transgenic mouse whose genome comprises a genetically engineered homozygous disruption of the endogenous calcineurin A α isoform (CNAα) gene, wherein no functional CNAα is produced by said mouse, and wherein said mouse exhibits a phenotype of defects in Y cell immunity, ataxia, seizures, weight loss, reduced life expectancy and accumulation of endogenous phosphorylated tau protein.

5. A transgenic mouse produced by the method of claim 4.

* * * * *

UNITED STATES PATENT AND TRADEMARK OFFICE
CERTIFICATE OF CORRECTION

PATENT NO. : 6,444,870 B1
DATED : September 3, 2002
INVENTOR(S) : Wei Zhang, Jonathan G. Seidman, Usamah S. Kayyali and Huntington Potter It is certified that error appears in the above-identified patent and that said Letters Patent is hereby corrected as shown below:

Title page,
Item [54], after the word "CALCINEURIN", add the word -- IN --, thereby correcting the title to read -- METHODS FOR ASSESSING THE ROLE OF CALCINEURIN IN IMMUNOSUPPRESSION AND NEUROTOXICITY --;

Item [75], Inventors, the third inventor's last name, delete "Kagyali" and insert therefor -- Kayyali --;

Column 59,
Line 25, after the words "phenotype of defects in", delete "Y cell immunity" and insert therefor -- T cell immunity --;
Line 45, after the word "and", delete " p1" and move "c)" to the next line, aligned directly under "b)";

Column 60,
Line 16, after the word "A", delete "Transgenic" and insert therefor -- transgenic --;
Line 20, after the words "defects in", delete "Y cell immunity" and insert therefor -- T cell immunity --;
Line 28, delete "Y cell immunity" and insert therefor -- T cell immunity --;
Line 30, after the word "comprising,", delete "p1" and move "a)" to the next line, indented and aligned under "4.";
Line 33, after the word "gene,", delete "p1" and move "b)" to the next line, indented and aligned under "4.";
Line 34, after the word "blastocyst;", delete "p1" and move "c)" to the next line indented and aligned under "4.";
Line 35, after the word "mouse;", delete "p1" and move "d)" to the next line, indented and aligned under "4.";

UNITED STATES PATENT AND TRADEMARK OFFICE
CERTIFICATE OF CORRECTION

PATENT NO.    : 6,444,870 B1
DATED         : September 3, 2002
INVENTOR(S)   : Wei Zhang, Jonathan G. Seidman, Usamah S. Kayyali and Huntington Potter It is certified that error appears in the above-identified patent and that said Letters Patent is hereby corrected as shown below:

<u>Column 60 cont'd,</u>
Line 36, after the word "birth;", delete "p1" and move "e)" to the next line, indented and aligned under "4.";
Line 37, delete the first word, "p1"; indent "f)" and align it under "4."; and
Line 42, after the words "defects in", delete "Y cell immunity" and insert therefor -- T cell immunity --.

Signed and Sealed this

Seventeenth Day of December, 2002

JAMES E. ROGAN
*Director of the United States Patent and Trademark Office*

SEQUENCE LISTING

```
<160> NUMBER OF SEQ ID NOS: 3

<210> SEQ ID NO 1
<211> LENGTH: 7
<212> TYPE: PRT
<213> ORGANISM: Unknown
<220> FEATURE:
<223> OTHER INFORMATION: C-terminal peptide from human CNAalpha

<400> SEQUENCE: 1

Ser Asn Ser Ser Asn Ile Gln
1               5

<210> SEQ ID NO 2
<211> LENGTH: 11
<212> TYPE: PRT
<213> ORGANISM: Unknown
<220> FEATURE:
<223> OTHER INFORMATION: Residues 386-396 of CNAbeta

<400> SEQUENCE: 2

Leu Met Thr Glu Gly Glu Asp Glu Phe Asp Gly
1               5                   10
```

```
<210> SEQ ID NO 3
<211> LENGTH: 19
<212> TYPE: PRT
<213> ORGANISM: Unknown
<220> FEATURE:
<223> OTHER INFORMATION: RII peptide

<400> SEQUENCE: 3

Asp Leu Asp Val Pro Ile Pro Gly Arg Phe Asp Arg Arg Val Ser Val
1               5                   10                  15
Ala Ala Glu
```